(12) United States Patent
Burd et al.

(10) Patent No.: US 11,143,647 B2
(45) Date of Patent: *Oct. 12, 2021

(54) MODULAR POINT-OF-CARE DEVICES, SYSTEMS, AND USES THEREOF

(71) Applicant: Labrador Diagnostics LLC, Wilmington, DE (US)

(72) Inventors: Tammy Burd, Palo Alto, CA (US); Ian Gibbons; Elizabeth A. Holmes, Palo Alto, CA (US); Gary Frenzel, Palo Alto, CA (US); Anthony Joseph Nugent, Palo Alto, CA (US)

(73) Assignee: Labrador Diagnostics, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/160,491

(22) Filed: May 20, 2016

(65) Prior Publication Data

US 2016/0266108 A1    Sep. 15, 2016

Related U.S. Application Data

(63) Continuation of application No. 15/007,585, filed on Jan. 27, 2016, now Pat. No. 9,588,109, which is a
(Continued)

(51) Int. Cl.
*G01N 33/53* (2006.01)
*G01N 33/543* (2006.01)
*B01J 19/00* (2006.01)
*B01L 3/02* (2006.01)
*B01L 3/00* (2006.01)
(Continued)

(52) U.S. Cl.
CPC .......... *G01N 33/5304* (2013.01); *A61B 5/15* (2013.01); *A61B 5/151* (2013.01); *A61B 5/150755* (2013.01); *B01J 19/0046* (2013.01); *B01L 3/0262* (2013.01); *B01L 3/5025* (2013.01); *B01L 3/527* (2013.01); *B01L 7/52* (2013.01); *B01L 9/543* (2013.01); *G01N 1/38* (2013.01); *G01N 33/5302* (2013.01); *G01N 33/54326* (2013.01); *G01N 33/54366* (2013.01); *G01N 33/54386* (2013.01); *G01N 33/56966* (2013.01); *G01N 33/57484* (2013.01); *G01N 33/6803* (2013.01); *G01N 33/94* (2013.01); *G01N 35/00732* (2013.01); *G01N 35/00871* (2013.01); *G01N 35/028* (2013.01); *G01N 35/10* (2013.01); *G01N 35/1065* (2013.01); *G01N 35/1074* (2013.01); *G16H 10/40* (2018.01); *A61B 10/007* (2013.01); *A61B 10/0038* (2013.01); *A61B 10/0045* (2013.01); *A61B 10/0051* (2013.01); *A61B 10/0058* (2013.01); *A61B 10/02* (2013.01); *A61B 2010/0074* (2013.01); *A61B 2010/0077* (2013.01); *B01J 2219/005* (2013.01); *B01J 2219/00283* (2013.01); *B01J 2219/00292* (2013.01); *B01J 2219/00315* (2013.01); *B01J 2219/00369* (2013.01); *B01J 2219/00371* (2013.01); *B01J 2219/00385* (2013.01); *B01J 2219/00466* (2013.01); *B01J 2219/00495* (2013.01); *B01J 2219/00693* (2013.01); *B01J 2219/00702* (2013.01); *B01L 3/021* (2013.01); *B01L 7/5255* (2013.01); *B01L 2200/04* (2013.01); *B01L 2200/0689* (2013.01); *B01L 2200/141* (2013.01); *B01L 2200/148* (2013.01); *B01L 2300/0654* (2013.01); *B01L 2300/0829* (2013.01); *B01L 2300/1805* (2013.01); *B01L 2400/043* (2013.01); *G01N 2035/0097* (2013.01); *G01N 2035/00237* (2013.01); *G01N 2035/00851* (2013.01); *G01N 2035/00881* (2013.01); *G01N 2035/1032* (2013.01); *G01N 2035/1034* (2013.01); *G01N 2035/1048* (2013.01); *G01N 2333/475* (2013.01); *G01N 2333/4737* (2013.01); *G01N 2333/71* (2013.01); *G01N 2333/912* (2013.01); *G01N 2333/9129* (2013.01); *G01N 2333/91205* (2013.01); *G01N 2800/26* (2013.01); *G01N 2800/60* (2013.01);
(Continued)

(58) Field of Classification Search
CPC combination set(s) only.
See application file for complete search history.

(56) References Cited

U.S. PATENT DOCUMENTS 2,398,234 A    4/1946  Long
3,600,900 A    8/1971  Lee
(Continued)

FOREIGN PATENT DOCUMENTS

CN    1146017 A    3/1997
CN    1173776 A    2/1998
(Continued)

OTHER PUBLICATIONS

Notice of Allowance dated Jun. 22, 2016 for U.S. Appl. No. 13/326,023.
(Continued)

*Primary Examiner* — Ann Y Lam
(74) *Attorney, Agent, or Firm* — Sterne, Kessler, Goldstein & Fox P.L.L.C.

(57) ABSTRACT

The present invention provides devices and systems for use at the point of care. The methods devices of the invention are directed toward automatic detection of analytes in a bodily fluid. The components of the device are modular to allow for flexibility and robustness of use with the disclosed methods for a variety of medical applications.

27 Claims, 21 Drawing Sheets

Related U.S. Application Data continuation of application No. 14/670,200, filed on Mar. 26, 2015, now Pat. No. 9,285,366, which is a continuation of application No. 13/893,258, filed on May 13, 2013, now Pat. No. 9,121,851, which is a continuation of application No. 13/889,674, filed on May 8, 2013, now Pat. No. 8,822,167, which is a continuation of application No. 13/326,023, filed on Dec. 14, 2011, now Pat. No. 9,435,793, which is a continuation of application No. 12/244,723, filed on Oct. 2, 2008, now Pat. No. 8,088,593.

(60) Provisional application No. 60/997,460, filed on Oct. 2, 2007.

(51) Int. Cl.
| | |
|---|---|
| *G01N 35/02* | (2006.01) |
| *B01L 9/00* | (2006.01) |
| *G16H 10/40* | (2018.01) |
| *G01N 1/38* | (2006.01) |
| *G01N 33/569* | (2006.01) |
| *A61B 5/15* | (2006.01) |
| *A61B 5/151* | (2006.01) |
| *G01N 35/10* | (2006.01) |
| *B01L 7/00* | (2006.01) |
| *G01N 33/68* | (2006.01) |
| *G01N 33/94* | (2006.01) |
| *G01N 35/00* | (2006.01) |
| *G01N 33/574* | (2006.01) |
| *A61B 10/00* | (2006.01) |
| *A61B 10/02* | (2006.01) |

(52) U.S. Cl.
CPC .. *Y10T 29/49826* (2015.01); *Y10T 436/25375* (2015.01)

(56) References Cited

U.S. PATENT DOCUMENTS

| | | |
|---|---|---|
| 3,640,434 A | 2/1972 | Walker |
| 3,696,971 A | 10/1972 | Maclin |
| 3,722,789 A | 3/1973 | Kennedy |
| 3,756,920 A | 9/1973 | Kelbaugh et al. |
| 3,766,381 A | 10/1973 | Watson |
| 3,865,495 A | 2/1975 | Sanz et al. |
| 3,953,172 A | 4/1976 | Shapiro et al. |
| 4,010,893 A | 3/1977 | Smith et al. |
| 4,157,781 A | 6/1979 | Maruyama |
| 4,250,830 A | 2/1981 | Leif |
| 4,270,921 A | 6/1981 | Graas |
| 4,276,258 A | 6/1981 | Ginsberg et al. |
| 4,276,383 A | 6/1981 | Leighton et al. |
| 4,327,595 A | 5/1982 | Schultz |
| 4,362,698 A | 12/1982 | Boosalis et al. |
| 4,437,586 A | 3/1984 | Columbus |
| 4,460,351 A | 7/1984 | Wakita et al. |
| 4,486,315 A | 12/1984 | Teipel |
| 4,488,814 A | 12/1984 | Johnson |
| 4,545,497 A | 10/1985 | Martha |
| 4,554,839 A | 11/1985 | Hewett et al. |
| 4,593,837 A | 6/1986 | Jakubowicz et al. |
| 4,683,195 A | 7/1987 | Mullis et al. |
| 4,725,406 A * | 2/1988 | Compton ............ G01N 21/8483 252/408.1 |
| 4,744,955 A | 5/1988 | Shapiro |
| 4,756,884 A | 7/1988 | Hillman et al. |
| 4,784,834 A | 11/1988 | Hirschmann |
| 4,810,096 A | 3/1989 | Russell et al. |
| 4,816,567 A | 3/1989 | Cabilly et al. |
| 4,822,331 A | 4/1989 | Taylor |
| 4,830,832 A | 5/1989 | Arpagaus et al. |
| 4,925,629 A | 5/1990 | Schramm |
| 4,933,291 A | 6/1990 | Daiss et al. |
| 4,967,604 A | 11/1990 | Arpagaus et al. |
| 5,005,981 A | 4/1991 | Schulte et al. |
| 5,055,263 A | 10/1991 | Meltzer |
| 5,061,381 A | 10/1991 | Burd |
| 5,061,449 A | 10/1991 | Torti et al. |
| 5,072,382 A | 12/1991 | Kamentsky |
| 5,089,229 A | 2/1992 | Heidt et al. |
| 5,112,574 A | 5/1992 | Horton |
| 5,122,284 A | 6/1992 | Braynin et al. |
| 5,130,238 A | 7/1992 | Malek et al. |
| 5,171,534 A | 12/1992 | Smith et al. |
| 5,173,193 A | 12/1992 | Schembri |
| 5,186,162 A | 2/1993 | Talish et al. |
| 5,230,864 A | 7/1993 | Columbus |
| 5,242,606 A | 9/1993 | Braynin et al. |
| 5,270,163 A | 12/1993 | Gold et al. |
| 5,270,184 A | 12/1993 | Walker et al. |
| 5,273,905 A | 12/1993 | Muller et al. |
| 5,281,395 A | 1/1994 | Markart et al. |
| 5,292,658 A | 3/1994 | Cormier et al. |
| 5,310,652 A | 5/1994 | Gelfand et al. |
| 5,320,808 A | 6/1994 | Holen et al. |
| 5,322,770 A | 6/1994 | Gelfand |
| 5,324,481 A | 6/1994 | Dunn et al. |
| 5,380,487 A | 1/1995 | Choperena et al. |
| 5,393,903 A | 2/1995 | Graetzel et al. |
| 5,399,491 A | 3/1995 | Kacian et al. |
| 5,403,415 A | 4/1995 | Schembri |
| 5,416,879 A | 5/1995 | Liu |
| 5,418,155 A | 5/1995 | Cormier et al. |
| 5,443,790 A | 8/1995 | Coeurveille et al. |
| 5,455,166 A | 10/1995 | Walker |
| 5,456,652 A | 10/1995 | Eberle |
| 5,463,228 A | 10/1995 | Krause |
| 5,472,603 A | 12/1995 | Schembri |
| 5,475,096 A | 12/1995 | Gold et al. |
| 5,478,750 A | 12/1995 | Bernstein et al. |
| 5,480,784 A | 1/1996 | Kacian et al. |
| 5,483,799 A | 1/1996 | Dalto |
| 5,507,410 A | 4/1996 | Clark et al. |
| 5,518,923 A | 5/1996 | Berndt et al. |
| 5,527,257 A | 6/1996 | Piramoon |
| 5,527,670 A | 6/1996 | Stanley |
| 5,530,101 A | 6/1996 | Queen et al. |
| 5,545,540 A | 8/1996 | Mian |
| 5,551,241 A | 9/1996 | Boeckel et al. |
| 5,578,269 A | 11/1996 | Yaremko et al. |
| 5,578,270 A | 11/1996 | Reichler et al. |
| 5,580,529 A | 12/1996 | Devaughn et al. |
| 5,585,089 A | 12/1996 | Queen et al. |
| 5,590,052 A | 12/1996 | Kopf-Sill et al. |
| 5,591,643 A | 1/1997 | Schembri |
| 5,599,411 A | 2/1997 | Schembri |
| 5,602,647 A | 2/1997 | Xu et al. |
| 5,628,890 A | 5/1997 | Carter et al. |
| 5,639,665 A * | 6/1997 | Arai ................ G01N 35/00029 422/404 |
| 5,648,211 A | 7/1997 | Fraiser et al. |
| 5,670,375 A | 9/1997 | Seaton et al. |
| 5,674,698 A | 10/1997 | Zarling et al. |
| 5,683,888 A | 11/1997 | Campbell |
| 5,687,716 A | 11/1997 | Kaufmann et al. |
| 5,693,233 A | 12/1997 | Schembri |
| 5,693,761 A | 12/1997 | Queen et al. |
| 5,693,762 A | 12/1997 | Queen et al. |
| 5,741,411 A | 4/1998 | Yeung et al. |
| 5,741,668 A | 4/1998 | Ward et al. |
| 5,758,443 A | 6/1998 | Pedrazzini |
| 5,772,962 A | 6/1998 | Uchida et al. |
| 5,777,079 A | 7/1998 | Tsien et al. |
| 5,779,981 A | 7/1998 | Danssaert et al. |
| 5,797,898 A | 8/1998 | Santini et al. |
| 5,804,387 A | 9/1998 | Cormack et al. |
| 5,807,523 A | 9/1998 | Watts et al. |
| 5,821,337 A | 10/1998 | Carter et al. |
| 5,842,787 A | 12/1998 | Kopf-Sill et al. |
| 5,844,686 A | 12/1998 | Treptow et al. |

(56) References Cited

U.S. PATENT DOCUMENTS

| | | | |
|---|---|---|---|
| 5,854,033 A | 12/1998 | Lizardi | |
| 5,854,684 A | 12/1998 | Stabile et al. | |
| 5,859,205 A | 1/1999 | Adair et al. | |
| 5,863,502 A | 1/1999 | Southgate et al. | |
| 5,874,046 A | 2/1999 | Megerle et al. | |
| 5,874,304 A | 2/1999 | Zolotukhin et al. | |
| 5,876,675 A | 3/1999 | Kennedy | |
| 5,876,995 A | 3/1999 | Bryan | |
| 5,879,628 A | 3/1999 | Ridgeway et al. | |
| 5,885,470 A | 3/1999 | Parce et al. | |
| 5,891,734 A | 4/1999 | Gill et al. | |
| 5,896,297 A | 4/1999 | Valerino | |
| 5,902,549 A | 5/1999 | Mimura et al. | |
| 5,906,795 A | 5/1999 | Nakashima et al. | |
| 5,915,284 A | 6/1999 | Meltzer et al. | |
| 5,925,558 A | 7/1999 | Tsien et al. | |
| 5,939,291 A | 8/1999 | Loewy et al. | |
| 5,942,443 A | 8/1999 | Parce et al. | |
| 5,960,160 A | 9/1999 | Clark et al. | |
| 5,961,451 A | 10/1999 | Reber et al. | |
| 5,976,896 A * | 11/1999 | Kumar | G01N 21/03 422/417 |
| 5,980,830 A | 11/1999 | Savage et al. | |
| 5,993,417 A | 11/1999 | Yerfino et al. | |
| 6,013,528 A | 1/2000 | Jacobs et al. | |
| 6,030,582 A | 2/2000 | Levy | |
| 6,033,850 A | 3/2000 | Purvis | |
| 6,042,909 A | 3/2000 | Dunleavy et al. | |
| 6,046,056 A | 4/2000 | Parce et al. | |
| 6,054,297 A | 4/2000 | Carter et al. | |
| 6,056,661 A | 5/2000 | Schmidt | |
| 6,060,022 A | 5/2000 | Pang et al. | |
| 6,063,341 A | 5/2000 | Fassbind et al. | |
| 6,074,616 A | 6/2000 | Buechler et al. | |
| 6,091,490 A | 7/2000 | Stellman et al. | |
| 6,114,122 A | 9/2000 | Besemer et al. | |
| 6,115,545 A | 9/2000 | Mellquist | |
| 6,121,054 A | 9/2000 | Lebl | |
| 6,143,252 A | 11/2000 | Haxo, Jr. et al. | |
| 6,156,181 A | 12/2000 | Parce et al. | |
| 6,159,368 A | 12/2000 | Moring et al. | |
| 6,168,914 B1 | 1/2001 | Campbell et al. | |
| 6,168,948 B1 | 1/2001 | Anderson et al. | |
| 6,174,675 B1 | 1/2001 | Chow et al. | |
| 6,180,370 B1 | 1/2001 | Queen et al. | |
| 6,191,852 B1 | 2/2001 | Paffhausen et al. | |
| 6,197,572 B1 | 3/2001 | Schneebeli | |
| 6,200,531 B1 | 3/2001 | Liljestrand et al. | |
| 6,210,891 B1 | 4/2001 | Nyren et al. | |
| 6,235,531 B1 | 5/2001 | Kopf-Sill et al. | |
| 6,235,534 B1 | 5/2001 | Brookes et al. | |
| 6,244,119 B1 | 6/2001 | Theran | |
| 6,245,057 B1 | 6/2001 | Sieben et al. | |
| 6,251,639 B1 | 6/2001 | Kurn | |
| 6,267,858 B1 | 7/2001 | Parce et al. | |
| 6,274,288 B1 | 8/2001 | Kewitsch et al. | |
| 6,277,605 B1 | 8/2001 | Wijnhoven et al. | |
| 6,290,907 B1 | 9/2001 | Takahashi et al. | |
| 6,291,249 B1 | 9/2001 | Mahant et al. | |
| 6,294,331 B1 | 9/2001 | Ried et al. | |
| 6,309,828 B1 | 10/2001 | Schleifer et al. | |
| 6,312,929 B1 | 11/2001 | McMillan | |
| 6,333,157 B1 | 12/2001 | Miller-Jones et al. | |
| 6,340,588 B1 | 1/2002 | Nova et al. | |
| 6,341,490 B1 | 1/2002 | Jones | |
| 6,348,176 B1 | 2/2002 | Hammer et al. | |
| 6,352,854 B1 | 3/2002 | Nova et al. | |
| 6,361,486 B1 | 3/2002 | Gordon | |
| 6,361,958 B1 | 3/2002 | Shieh et al. | |
| 6,368,275 B1 | 4/2002 | Sliwa et al. | |
| 6,368,871 B1 | 4/2002 | Christel et al. | |
| 6,369,893 B1 | 4/2002 | Christel et al. | |
| 6,372,185 B1 | 4/2002 | Shumate et al. | |
| 6,372,428 B1 | 4/2002 | Nova et al. | |
| 6,375,028 B1 | 4/2002 | Smith | |
| 6,379,929 B1 | 4/2002 | Burns et al. | |
| 6,403,338 B1 | 6/2002 | Knapp et al. | |
| 6,407,213 B1 | 6/2002 | Carter et al. | |
| 6,410,278 B1 | 6/2002 | Notomi et al. | |
| 6,420,143 B1 | 7/2002 | Kopf-Sill | |
| 6,440,725 B1 | 8/2002 | Pourahmadi et al. | |
| 6,465,953 B1 | 10/2002 | Duggal | |
| 6,468,474 B2 | 10/2002 | Bachand et al. | |
| 6,471,916 B1 | 10/2002 | Noblett | |
| 6,477,394 B2 | 11/2002 | Rice et al. | |
| 6,482,593 B2 | 11/2002 | Walt et al. | |
| 6,484,104 B2 | 11/2002 | Abraham-Fuchs et al. | |
| 6,484,897 B1 | 11/2002 | Crawley | |
| 6,491,666 B1 | 12/2002 | Santini, Jr. et al. | |
| 6,506,611 B2 | 1/2003 | Bienert et al. | |
| 6,509,193 B1 | 1/2003 | Tajima | |
| 6,517,475 B1 | 2/2003 | Brown et al. | |
| 6,544,732 B1 | 4/2003 | Chee et al. | |
| 6,551,838 B2 | 4/2003 | Santini, Jr. et al. | |
| 6,565,813 B1 | 5/2003 | Garyantes | |
| 6,565,815 B1 | 5/2003 | Chang et al. | |
| 6,583,879 B1 | 6/2003 | Berg et al. | |
| 6,589,789 B1 | 7/2003 | Hubert et al. | |
| 6,591,124 B2 | 7/2003 | Sherman et al. | |
| 6,599,476 B1 | 7/2003 | Watson et al. | |
| 6,605,213 B1 | 8/2003 | Smith | |
| 6,627,160 B2 | 9/2003 | Wanner | |
| 6,632,216 B2 | 10/2003 | Houzego et al. | |
| 6,656,428 B1 | 12/2003 | Clark et al. | |
| 6,663,003 B2 | 12/2003 | Johnson et al. | |
| 6,664,104 B2 | 12/2003 | Pourahmadi et al. | |
| 6,689,615 B1 | 2/2004 | Murto et al. | |
| 6,732,598 B2 | 5/2004 | Schoeppe | |
| 6,748,337 B2 | 6/2004 | Wardlaw et al. | |
| 6,752,961 B2 | 6/2004 | Kopf-Sill et al. | |
| 6,752,965 B2 | 6/2004 | Levy | |
| 6,780,645 B2 | 8/2004 | Hayter et al. | |
| 6,797,518 B1 | 9/2004 | Jacobs et al. | |
| 6,805,842 B1 | 10/2004 | Bodner et al. | |
| 6,825,921 B1 | 11/2004 | Modlin et al. | |
| 6,833,246 B2 | 12/2004 | Balasubramanian | |
| 6,858,185 B1 * | 2/2005 | Kopf-Sill | B01L 3/5027 422/504 |
| 6,859,830 B1 | 2/2005 | Ronneburg et al. | |
| 6,878,540 B2 | 4/2005 | Pourahmadi et al. | |
| 6,881,541 B2 | 4/2005 | Petersen et al. | |
| 6,887,202 B2 | 5/2005 | Currie et al. | |
| 6,887,693 B2 | 5/2005 | McMillan et al. | |
| 6,893,879 B2 | 5/2005 | Petersen et al. | |
| 6,899,848 B1 | 5/2005 | Chen et al. | |
| 6,905,816 B2 | 6/2005 | Jacobs et al. | |
| 6,917,726 B2 | 7/2005 | Levene et al. | |
| 6,940,598 B2 | 9/2005 | Christel et al. | |
| 6,946,251 B2 | 9/2005 | Kurn | |
| 6,947,582 B1 | 9/2005 | Vilsmeier et al. | |
| 6,949,377 B2 | 9/2005 | Ho | |
| 6,979,424 B2 | 12/2005 | Northrup et al. | |
| 7,033,764 B2 | 4/2006 | Korlach et al. | |
| 7,052,847 B2 | 5/2006 | Korlach et al. | |
| 7,056,676 B2 | 6/2006 | Korlach et al. | |
| 7,109,293 B2 | 9/2006 | Hwang et al. | |
| 7,135,144 B2 | 11/2006 | Christel et al. | |
| 7,170,050 B2 | 1/2007 | Turner et al. | |
| 7,172,897 B2 | 2/2007 | Blackburn et al. | |
| 7,177,767 B2 | 2/2007 | Ostoich et al. | |
| 7,185,551 B2 | 3/2007 | Schwartz | |
| 7,188,001 B2 | 3/2007 | Young et al. | |
| 7,255,833 B2 | 8/2007 | Chang et al. | |
| 7,272,252 B2 | 9/2007 | De La et al. | |
| 7,276,158 B1 | 10/2007 | Shukla et al. | |
| 7,358,098 B2 | 4/2008 | Noda et al. | |
| 7,361,466 B2 | 4/2008 | Korlach et al. | |
| 7,394,363 B1 | 7/2008 | Ghahramani | |
| 7,416,844 B2 | 8/2008 | Korlach et al. | |
| 7,422,554 B2 | 9/2008 | Moscone et al. | |
| 7,429,652 B2 | 9/2008 | Wang et al. | |
| 7,438,857 B2 | 10/2008 | Massaro | |
| 7,481,787 B2 | 1/2009 | Gable et al. | |
| 7,494,791 B2 | 2/2009 | Goel | |

(56) References Cited

U.S. PATENT DOCUMENTS

| | | | |
|---|---|---|---|
| 7,497,997 B2* | 3/2009 | Glezer | B01L 3/5027 422/504 |
| 7,548,034 B2 | 6/2009 | Takahashi et al. | |
| 7,569,346 B2 | 8/2009 | Petersen et al. | |
| 7,581,660 B2 | 9/2009 | Nay et al. | |
| 7,587,201 B2 | 9/2009 | Ohara | |
| 7,609,654 B2 | 10/2009 | Lubeck et al. | |
| 7,632,462 B2 | 12/2009 | Holtlund et al. | |
| 7,635,594 B2* | 12/2009 | Holmes | A61B 5/1411 422/67 |
| 7,650,395 B2 | 1/2010 | Johnson et al. | |
| 7,662,343 B2 | 2/2010 | Mathus et al. | |
| 7,690,275 B1 | 4/2010 | Wiederin et al. | |
| 7,691,332 B2 | 4/2010 | Kacian et al. | |
| 7,702,524 B1 | 4/2010 | Whibbs et al. | |
| 7,711,800 B2 | 5/2010 | Gavrilescu et al. | |
| 7,744,821 B2 | 6/2010 | Eberle | |
| 7,765,069 B2 | 7/2010 | Ostoich et al. | |
| 7,771,658 B2 | 8/2010 | Larsen | |
| 7,771,926 B2 | 8/2010 | Petyt et al. | |
| 7,824,612 B2 | 11/2010 | Fuisz et al. | |
| 7,824,890 B2 | 11/2010 | Hoser et al. | |
| 7,887,750 B2 | 2/2011 | Blatt et al. | |
| 7,898,569 B2 | 3/2011 | Koselka et al. | |
| 7,914,994 B2 | 3/2011 | Petersen et al. | |
| 7,923,256 B2 | 4/2011 | Widrig Opalsky et al. | |
| 7,925,069 B2 | 4/2011 | Ortyn et al. | |
| 7,955,867 B2 | 6/2011 | Park | |
| 7,978,665 B1 | 7/2011 | Jaynes et al. | |
| 7,998,411 B2 | 8/2011 | Kopf-Sill et al. | |
| 8,008,066 B2 | 8/2011 | Lair et al. | |
| 8,024,395 B1 | 9/2011 | Odom | |
| 8,029,733 B2 | 10/2011 | Chang et al. | |
| 8,030,080 B2 | 10/2011 | Spence et al. | |
| 8,088,593 B2* | 1/2012 | Burd | B01J 19/0046 435/7.92 |
| 8,133,671 B2 | 3/2012 | Williams et al. | |
| 8,158,430 B1 | 4/2012 | Roy et al. | |
| 8,194,235 B2 | 6/2012 | Kosaka et al. | |
| 8,211,386 B2 | 7/2012 | Talmer et al. | |
| 8,247,176 B2 | 8/2012 | Petersen et al. | |
| 8,283,155 B2 | 10/2012 | Holmes et al. | |
| 8,287,820 B2 | 10/2012 | Williams et al. | |
| 8,309,035 B2 | 11/2012 | Chen et al. | |
| 8,309,317 B2 | 11/2012 | Chen et al. | |
| 8,323,564 B2 | 12/2012 | Padmanabhan et al. | |
| 8,380,541 B1 | 2/2013 | Holmes | |
| 8,383,421 B2 | 2/2013 | Yanagida et al. | |
| 8,387,811 B2 | 3/2013 | Livingston et al. | |
| 8,392,585 B1 | 3/2013 | Balwani | |
| 8,394,608 B2 | 3/2013 | Ririe et al. | |
| 8,435,738 B2 | 5/2013 | Holmes | |
| 8,475,739 B2 | 7/2013 | Holmes et al. | |
| 8,580,559 B2 | 11/2013 | Petersen et al. | |
| 8,588,807 B2 | 11/2013 | Kumar | |
| 8,592,157 B2 | 11/2013 | Petersen et al. | |
| 8,697,377 B2* | 4/2014 | Burd | B01J 19/0046 435/7.92 |
| 8,822,167 B2* | 9/2014 | Burd | B01J 19/0046 435/7.92 |
| 8,877,507 B2 | 11/2014 | Xia et al. | |
| 8,883,518 B2* | 11/2014 | Roy | G01N 33/49 436/518 |
| 9,012,163 B2* | 4/2015 | Burd | B01J 19/0046 435/7.92 |
| 9,121,801 B2 | 9/2015 | Clark et al. | |
| 9,121,851 B2* | 9/2015 | Burd | B01J 19/0046 |
| 9,128,015 B2 | 9/2015 | Holmes et al. | |
| 9,131,884 B2 | 9/2015 | Holmes et al. | |
| 9,156,032 B2 | 10/2015 | Petersen et al. | |
| 9,168,523 B2 | 10/2015 | Ludowise et al. | |
| 9,250,229 B2* | 2/2016 | Holmes | G01N 35/00 |
| 9,285,366 B2* | 3/2016 | Burd | B01J 19/0046 |
| 9,435,793 B2* | 9/2016 | Burd | B01J 19/0046 |
| 9,588,109 B2* | 3/2017 | Burd | B01J 19/0046 |
| 9,789,481 B2 | 10/2017 | Petersen et al. | |
| 10,533,994 B2 | 1/2020 | Holmes et al. | |
| 2001/0012612 A1 | 8/2001 | Petersen et al. | |
| 2001/0019845 A1 | 9/2001 | Bienert et al. | |
| 2001/0045355 A1 | 11/2001 | Gephart et al. | |
| 2001/0048899 A1 | 12/2001 | Marouiss et al. | |
| 2001/0051766 A1 | 12/2001 | Gazdzinski | |
| 2002/0019060 A1 | 2/2002 | Petersen et al. | |
| 2002/0025576 A1 | 2/2002 | Northrup et al. | |
| 2002/0034757 A1 | 3/2002 | Cubicciotti | |
| 2002/0039723 A1 | 4/2002 | Fox et al. | |
| 2002/0039783 A1 | 4/2002 | McMillan et al. | |
| 2002/0042125 A1 | 4/2002 | Petersen et al. | |
| 2002/0045246 A1 | 4/2002 | McMillan et al. | |
| 2002/0052761 A1 | 5/2002 | Fey et al. | |
| 2002/0055167 A1 | 5/2002 | Pourahmadi et al. | |
| 2002/0059030 A1 | 5/2002 | Otworth et al. | |
| 2002/0065457 A1 | 5/2002 | Kuth | |
| 2002/0074882 A1 | 6/2002 | Werfel et al. | |
| 2002/0085952 A1 | 7/2002 | Ellingboe et al. | |
| 2002/0087101 A1 | 7/2002 | Barrick et al. | |
| 2002/0106786 A1 | 8/2002 | Carvalho et al. | |
| 2002/0108857 A1 | 8/2002 | Paschetto et al. | |
| 2002/0109844 A1 | 8/2002 | Christel et al. | |
| 2002/0110496 A1 | 8/2002 | Samsoondar | |
| 2002/0114739 A1 | 8/2002 | Weigl et al. | |
| 2002/0120183 A1 | 8/2002 | Abraham-Fuchs et al. | |
| 2002/0120187 A1 | 8/2002 | Eiffert et al. | |
| 2002/0127708 A1 | 9/2002 | Kluttz et al. | |
| 2002/0130100 A1 | 9/2002 | Smith | |
| 2002/0132226 A1 | 9/2002 | Nair et al. | |
| 2002/0139936 A1 | 10/2002 | Dumas | |
| 2002/0141904 A1 | 10/2002 | Rosen et al. | |
| 2002/0143437 A1 | 10/2002 | Handique et al. | |
| 2002/0149772 A1 | 10/2002 | Halg | |
| 2002/0155599 A1 | 10/2002 | Vellinger et al. | |
| 2002/0155616 A1 | 10/2002 | Hiramatsu et al. | |
| 2002/0156365 A1 | 10/2002 | Tsekos | |
| 2002/0160353 A1 | 10/2002 | Sundaram et al. | |
| 2002/0161606 A1 | 10/2002 | Bennett et al. | |
| 2002/0164770 A1 | 11/2002 | Hoffmann | |
| 2002/0168784 A1 | 11/2002 | Sundrehagen et al. | |
| 2002/0175079 A1 | 11/2002 | Christel et al. | |
| 2002/0176801 A1 | 11/2002 | Giebeler et al. | |
| 2002/0187074 A1* | 12/2002 | O'Connor | B01F 5/0682 422/82.05 |
| 2002/0192112 A1 | 12/2002 | Chow | |
| 2003/0012699 A1 | 1/2003 | Moore et al. | |
| 2003/0032035 A1* | 2/2003 | Chatelain | B01L 3/5027 435/6.14 |
| 2003/0049865 A1 | 3/2003 | Santini et al. | |
| 2003/0052074 A1 | 3/2003 | Chang et al. | |
| 2003/0061687 A1 | 4/2003 | Hansen et al. | |
| 2003/0064386 A1* | 4/2003 | Karaki | G01N 33/54313 435/6.11 |
| 2003/0069560 A1 | 4/2003 | Adamis et al. | |
| 2003/0077207 A1 | 4/2003 | Tyndorf et al. | |
| 2003/0100822 A1 | 5/2003 | Lew et al. | |
| 2003/0104590 A1 | 6/2003 | Santini et al. | |
| 2003/0112432 A1 | 6/2003 | Yguerabide et al. | |
| 2003/0114735 A1 | 6/2003 | Silver et al. | |
| 2003/0127609 A1 | 7/2003 | El-Hage et al. | |
| 2003/0138140 A1 | 7/2003 | Marcelpoil et al. | |
| 2003/0152492 A1 | 8/2003 | Chang et al. | |
| 2003/0153900 A1 | 8/2003 | Aceti et al. | |
| 2003/0165398 A1 | 9/2003 | Waldo et al. | |
| 2003/0170705 A1 | 9/2003 | Schulman et al. | |
| 2003/0175164 A1 | 9/2003 | Micklash et al. | |
| 2003/0175993 A1 | 9/2003 | Toranto et al. | |
| 2003/0207457 A1 | 11/2003 | Kopf-Sill et al. | |
| 2003/0207463 A1 | 11/2003 | Iheme et al. | |
| 2003/0208113 A1 | 11/2003 | Mault et al. | |
| 2003/0208133 A1 | 11/2003 | Mault | |
| 2003/0211618 A1 | 11/2003 | Patel | |
| 2003/0212379 A1 | 11/2003 | Land et al. | |
| 2004/0005582 A1 | 1/2004 | Shipwash | |
| 2004/0005699 A1 | 1/2004 | Roos et al. | |
| 2004/0014202 A1 | 1/2004 | King et al. | |

(56) References Cited

U.S. PATENT DOCUMENTS

| | | |
|---|---|---|
| 2004/0020310 A1 | 2/2004 | Escal |
| 2004/0022677 A1 | 2/2004 | Wohlstadter et al. |
| 2004/0029266 A1 | 2/2004 | Barbera-Guillem |
| 2004/0033501 A1 | 2/2004 | Lappe et al. |
| 2004/0044560 A1 | 3/2004 | Giglio et al. |
| 2004/0053290 A1 | 3/2004 | Terbrueggen et al. |
| 2004/0055361 A1 | 3/2004 | Schneider et al. |
| 2004/0058378 A1 | 3/2004 | Kong et al. |
| 2004/0074849 A1 | 4/2004 | Brown et al. |
| 2004/0078145 A1 | 4/2004 | Ostoich et al. |
| 2004/0086872 A1 | 5/2004 | Childers et al. |
| 2004/0087426 A1 | 5/2004 | Lattanzi |
| 2004/0096959 A1 | 5/2004 | Stiene et al. |
| 2004/0099628 A1 | 5/2004 | Casterlin |
| 2004/0109793 A1 | 6/2004 | McNeely et al. |
| 2004/0115720 A1 | 6/2004 | McWilliams et al. |
| 2004/0120848 A1 | 6/2004 | Teodorczyk |
| 2004/0122559 A1 | 6/2004 | Young et al. |
| 2004/0127252 A1 | 7/2004 | Tsunomoto et al. |
| 2004/0132220 A1 | 7/2004 | Fish |
| 2004/0134750 A1 | 7/2004 | Luoma |
| 2004/0161368 A1* | 8/2004 | Holtlund ............... B01L 3/0275 422/68.1 |
| 2004/0166027 A1 | 8/2004 | Wilmer et al. |
| 2004/0209374 A1 | 10/2004 | Kopf-Sill et al. |
| 2004/0228766 A1 | 11/2004 | Witty et al. |
| 2004/0230400 A1 | 11/2004 | Tomasso et al. |
| 2004/0233043 A1 | 11/2004 | Yazawa et al. |
| 2004/0241043 A1 | 12/2004 | Sattler |
| 2004/0241048 A1 | 12/2004 | Shin et al. |
| 2005/0009101 A1 | 1/2005 | Blackburn |
| 2005/0009191 A1 | 1/2005 | Swenson et al. |
| 2005/0010098 A1 | 1/2005 | Frigstad et al. |
| 2005/0036907 A1 | 2/2005 | Shoji |
| 2005/0054078 A1 | 3/2005 | Miller et al. |
| 2005/0074873 A1 | 4/2005 | Shanler et al. |
| 2005/0084921 A1* | 4/2005 | Cranley ............... C12N 9/0006 435/25 |
| 2005/0100937 A1* | 5/2005 | Holmes ................. A61B 5/0024 435/6.12 |
| 2005/0106713 A1 | 5/2005 | Phan et al. |
| 2005/0125258 A1 | 6/2005 | Yellin et al. |
| 2005/0147559 A1 | 7/2005 | Von Alten |
| 2005/0152900 A1 | 7/2005 | Najib et al. |
| 2005/0159982 A1 | 7/2005 | Showalter et al. |
| 2005/0164204 A1 | 7/2005 | Reed |
| 2005/0176940 A1 | 8/2005 | King |
| 2005/0180885 A1 | 8/2005 | Tateishi et al. |
| 2005/0180892 A1 | 8/2005 | Davies et al. |
| 2005/0194316 A1 | 9/2005 | Pourahmadi et al. |
| 2005/0220668 A1 | 10/2005 | Coville |
| 2005/0225751 A1 | 10/2005 | Sandell et al. |
| 2005/0227370 A1 | 10/2005 | Ramel et al. |
| 2005/0231723 A1 | 10/2005 | Blasenheim et al. |
| 2005/0236317 A1 | 10/2005 | DeSilets et al. |
| 2005/0283318 A1 | 12/2005 | Ostoich et al. |
| 2006/0013733 A1 | 1/2006 | Meeks et al. |
| 2006/0019274 A1 | 1/2006 | Goel |
| 2006/0024841 A1 | 2/2006 | Yao et al. |
| 2006/0026040 A1 | 2/2006 | Reeves et al. |
| 2006/0034732 A1 | 2/2006 | Bargh et al. |
| 2006/0045806 A1 | 3/2006 | Winther et al. |
| 2006/0051243 A1 | 3/2006 | Chow et al. |
| 2006/0057559 A1 | 3/2006 | Xu et al. |
| 2006/0057599 A1 | 3/2006 | Dzenitis et al. |
| 2006/0062697 A1 | 3/2006 | Eberle |
| 2006/0062852 A1 | 3/2006 | Holmes |
| 2006/0073538 A1 | 4/2006 | Konrad |
| 2006/0074063 A1 | 4/2006 | Fernandez-Pol |
| 2006/0083660 A1 | 4/2006 | Schorno et al. |
| 2006/0095429 A1 | 5/2006 | Abhyankar et al. |
| 2006/0110725 A1 | 5/2006 | Lee et al. |
| 2006/0115384 A1 | 6/2006 | Wohleb |
| 2006/0121491 A1 | 6/2006 | Wolber et al. |
| 2006/0121502 A1 | 6/2006 | Cain et al. |
| 2006/0153736 A1 | 7/2006 | Kalra et al. |
| 2006/0154327 A1 | 7/2006 | Bachur, Jr. et al. |
| 2006/0160170 A1 | 7/2006 | Giordano |
| 2006/0182738 A1 | 8/2006 | Holmes |
| 2006/0183217 A1 | 8/2006 | Yanagida et al. |
| 2006/0210435 A1* | 9/2006 | Alavie ................. G01N 21/253 422/65 |
| 2006/0223178 A1 | 10/2006 | Barber et al. |
| 2006/0245978 A1 | 11/2006 | Prins |
| 2006/0263263 A1 | 11/2006 | Shimizu |
| 2006/0263871 A1 | 11/2006 | Kluttz et al. |
| 2006/0264780 A1 | 11/2006 | Holmes et al. |
| 2006/0264783 A1 | 11/2006 | Holmes et al. |
| 2006/0275861 A1 | 12/2006 | Angros et al. |
| 2006/0286619 A1 | 12/2006 | Ricci et al. |
| 2006/0292039 A1 | 12/2006 | Iida |
| 2007/0004577 A1 | 1/2007 | Lederer |
| 2007/0035819 A1 | 2/2007 | Bahatt et al. |
| 2007/0048188 A1 | 3/2007 | Bigus |
| 2007/0055538 A1 | 3/2007 | Burton |
| 2007/0059196 A1 | 3/2007 | Brister et al. |
| 2007/0073113 A1 | 3/2007 | Squilla et al. |
| 2007/0077173 A1 | 4/2007 | Melet |
| 2007/0109294 A1 | 5/2007 | Gotman et al. |
| 2007/0118399 A1 | 5/2007 | Avinash et al. |
| 2007/0125677 A1 | 6/2007 | Oronsky et al. |
| 2007/0134128 A1 | 6/2007 | Korlach |
| 2007/0146873 A1 | 6/2007 | Ortyn et al. |
| 2007/0148759 A1 | 6/2007 | Amano et al. |
| 2007/0149874 A1 | 6/2007 | Say et al. |
| 2007/0154922 A1 | 7/2007 | Collier et al. |
| 2007/0166725 A1 | 7/2007 | McBride et al. |
| 2007/0177778 A1 | 8/2007 | Massaro |
| 2007/0178580 A1 | 8/2007 | Tajima et al. |
| 2007/0192138 A1 | 8/2007 | Saito et al. |
| 2007/0202538 A1 | 8/2007 | Glezer et al. |
| 2007/0207161 A1 | 9/2007 | Ralph |
| 2007/0207450 A1 | 9/2007 | Rodgers et al. |
| 2007/0224084 A1 | 9/2007 | Holmes et al. |
| 2007/0264629 A1 | 11/2007 | Holmes et al. |
| 2007/0269345 A1 | 11/2007 | Schilffarth et al. |
| 2007/0292941 A1 | 12/2007 | Handique et al. |
| 2007/0295113 A1 | 12/2007 | Londo et al. |
| 2008/0001735 A1 | 1/2008 | Tran |
| 2008/0003649 A1 | 1/2008 | Maltezos et al. |
| 2008/0019878 A1 | 1/2008 | Trump |
| 2008/0026483 A1 | 1/2008 | Oldenburg |
| 2008/0032416 A1 | 2/2008 | Park et al. |
| 2008/0038771 A1 | 2/2008 | Taylor et al. |
| 2008/0050280 A1 | 2/2008 | Fujita |
| 2008/0057572 A1 | 3/2008 | Petersen et al. |
| 2008/0065420 A1 | 3/2008 | Tirinato et al. |
| 2008/0110753 A1 | 5/2008 | Fourrier et al. |
| 2008/0118988 A1 | 5/2008 | Johnson et al. |
| 2008/0144005 A1 | 6/2008 | Guiney et al. |
| 2008/0153096 A1 | 6/2008 | Witty et al. |
| 2008/0166753 A1 | 7/2008 | Storey et al. |
| 2008/0179301 A1 | 7/2008 | Garty et al. |
| 2008/0198379 A1 | 8/2008 | Coker et al. |
| 2008/0206751 A1 | 8/2008 | Squirrell et al. |
| 2008/0223841 A1 | 9/2008 | Lofy |
| 2008/0228107 A1 | 9/2008 | Reddy |
| 2008/0243394 A1 | 10/2008 | Petricoin et al. |
| 2008/0253927 A1 | 10/2008 | Burow et al. |
| 2008/0253933 A1 | 10/2008 | Redfern |
| 2008/0254532 A1 | 10/2008 | Chang et al. |
| 2008/0261210 A1 | 10/2008 | Frantzen et al. |
| 2008/0299652 A1 | 12/2008 | Owen et al. |
| 2008/0308404 A1 | 12/2008 | Luotola et al. |
| 2009/0004754 A1 | 1/2009 | Oldenburg |
| 2009/0021728 A1 | 1/2009 | Heinz et al. |
| 2009/0043607 A1 | 2/2009 | Nemoto et al. |
| 2009/0057259 A1 | 3/2009 | Johnson et al. |
| 2009/0059218 A1 | 3/2009 | Harner et al. |
| 2009/0081648 A1 | 3/2009 | Wangh |
| 2009/0088336 A1 | 4/2009 | Burd et al. |
| 2009/0093970 A1 | 4/2009 | Lewy et al. |
| 2009/0094361 A1 | 4/2009 | Srinivasan |
| 2009/0098594 A1 | 4/2009 | Fantl et al. |

(56) References Cited

U.S. PATENT DOCUMENTS

| | | |
|---|---|---|
| 2009/0104079 A1 | 4/2009 | O'Connell et al. |
| 2009/0104689 A1 | 4/2009 | Kim et al. |
| 2009/0117009 A1 | 5/2009 | Cote |
| 2009/0124284 A1 | 5/2009 | Scherzer et al. |
| 2009/0141272 A1 | 6/2009 | Oldham et al. |
| 2009/0143235 A1 | 6/2009 | Drmanac et al. |
| 2009/0148941 A1 | 6/2009 | Florez et al. |
| 2009/0181463 A1 | 7/2009 | Chen |
| 2009/0203085 A1 | 8/2009 | Kurn et al. |
| 2009/0204435 A1 | 8/2009 | Gale |
| 2009/0208966 A1 | 8/2009 | Kacian et al. |
| 2009/0215157 A1 | 8/2009 | Jung et al. |
| 2009/0221059 A1 | 9/2009 | Williams et al. |
| 2009/0223311 A1 | 9/2009 | Hamada et al. |
| 2009/0227041 A1 | 9/2009 | Wang et al. |
| 2009/0246782 A1 | 10/2009 | Kelso et al. |
| 2009/0274348 A1 | 11/2009 | Jakubowicz et al. |
| 2009/0274587 A1 | 11/2009 | Butz et al. |
| 2009/0298075 A1 | 12/2009 | Travers et al. |
| 2009/0298129 A1 | 12/2009 | Spence et al. |
| 2009/0305392 A1 | 12/2009 | Alfredsson et al. |
| 2009/0318775 A1 | 12/2009 | Michelson et al. |
| 2009/0325210 A1 | 12/2009 | Weichselbaum et al. |
| 2010/0009364 A1 | 1/2010 | Fantl et al. |
| 2010/0009456 A1 | 1/2010 | Prins et al. |
| 2010/0009460 A1 | 1/2010 | Clark et al. |
| 2010/0009831 A1 | 1/2010 | Ryu et al. |
| 2010/0015634 A1 | 1/2010 | VanDine et al. |
| 2010/0015690 A1 | 1/2010 | Heavner |
| 2010/0027868 A1 | 2/2010 | Kosaka et al. |
| 2010/0028207 A1 | 2/2010 | Colella et al. |
| 2010/0034706 A1 | 2/2010 | Mathus et al. |
| 2010/0047128 A1 | 2/2010 | Mototsu et al. |
| 2010/0047790 A1 | 2/2010 | Southern et al. |
| 2010/0068706 A1 | 3/2010 | Pourahmadi et al. |
| 2010/0081144 A1 | 4/2010 | Holmes et al. |
| 2010/0081894 A1 | 4/2010 | Zdeblick et al. |
| 2010/0082781 A1 | 4/2010 | Lubeck et al. |
| 2010/0105074 A1 | 4/2010 | Covey et al. |
| 2010/0111773 A1 | 5/2010 | Pantelidis |
| 2010/0121156 A1 | 5/2010 | Yoo |
| 2010/0124746 A1 | 5/2010 | Liew |
| 2010/0132487 A1 | 6/2010 | Haack et al. |
| 2010/0151472 A1 | 6/2010 | Nolan et al. |
| 2010/0152885 A1 | 6/2010 | Regan et al. |
| 2010/0157302 A1 | 6/2010 | Serai et al. |
| 2010/0174181 A1 | 7/2010 | Nemoto |
| 2010/0184093 A1 | 7/2010 | Donovan et al. |
| 2010/0215644 A1 | 8/2010 | Fantl et al. |
| 2010/0240544 A1 | 9/2010 | Liu et al. |
| 2010/0246416 A1 | 9/2010 | Sinha et al. |
| 2010/0256470 A1 | 10/2010 | Miller |
| 2010/0262432 A1 | 10/2010 | Benja-Athon |
| 2010/0291588 A1 | 11/2010 | Mcdevitt et al. |
| 2010/0294950 A1 | 11/2010 | Kitamura et al. |
| 2011/0003392 A1 | 1/2011 | Stayton et al. |
| 2011/0003699 A1 | 1/2011 | Yoder et al. |
| 2011/0007261 A1 | 1/2011 | Abbott et al. |
| 2011/0008825 A1 | 1/2011 | Ingber et al. |
| 2011/0034758 A1 | 2/2011 | Shany et al. |
| 2011/0056290 A1 | 3/2011 | Bryant et al. |
| 2011/0093249 A1 | 4/2011 | Holmes et al. |
| 2011/0116385 A1 | 5/2011 | Turlington et al. |
| 2011/0124128 A1 | 5/2011 | Oosterbroek et al. |
| 2011/0129931 A1 | 6/2011 | Reboud et al. |
| 2011/0130740 A1 | 6/2011 | Levy |
| 2011/0143947 A1 | 6/2011 | Chamberlin et al. |
| 2011/0151502 A1 | 6/2011 | Kendall et al. |
| 2011/0176051 A1 | 7/2011 | Randers-Pehrson et al. |
| 2011/0183433 A1* | 7/2011 | Motadel ............ B01L 3/0275 436/180 |
| 2011/0189785 A1 | 8/2011 | Gutmann et al. |
| 2011/0201099 A1 | 8/2011 | Anderson et al. |
| 2011/0201121 A1 | 8/2011 | Kaartinen |
| 2011/0207617 A1 | 8/2011 | Faham et al. |
| 2011/0207619 A1 | 8/2011 | Ehben et al. |
| 2011/0213564 A1 | 9/2011 | Henke |
| 2011/0213579 A1 | 9/2011 | Henke |
| 2011/0213619 A1 | 9/2011 | Henke |
| 2011/0218428 A1 | 9/2011 | Westmoreland et al. |
| 2011/0233148 A1 | 9/2011 | Antonchuk et al. |
| 2011/0256025 A1 | 10/2011 | Mabuchi et al. |
| 2011/0287447 A1 | 11/2011 | Norderhaug et al. |
| 2012/0053068 A1 | 3/2012 | Remacle et al. |
| 2012/0059664 A1 | 3/2012 | Georgiev et al. |
| 2012/0071313 A1 | 3/2012 | Mackel et al. |
| 2012/0105837 A1 | 5/2012 | Ingber |
| 2012/0141339 A1 | 6/2012 | Sattler et al. |
| 2012/0142020 A1 | 6/2012 | Miller |
| 2012/0142043 A1 | 6/2012 | Koyata et al. |
| 2012/0149035 A1 | 6/2012 | Burd et al. |
| 2012/0171758 A1 | 7/2012 | Petersen et al. |
| 2012/0171759 A1 | 7/2012 | Williams et al. |
| 2012/0178091 A1 | 7/2012 | Glezer et al. |
| 2012/0206587 A1 | 8/2012 | Oz et al. |
| 2012/0224179 A1 | 9/2012 | Page |
| 2012/0252005 A1 | 10/2012 | Chiang et al. |
| 2012/0282603 A1 | 11/2012 | Hansen et al. |
| 2012/0291872 A1 | 11/2012 | Brady et al. |
| 2012/0295269 A1 | 11/2012 | Pourahmadi et al. |
| 2012/0309636 A1 | 12/2012 | Gibbons et al. |
| 2013/0074614 A1 | 3/2013 | Holmes et al. |
| 2013/0078149 A1 | 3/2013 | Holmes et al. |
| 2013/0078624 A1 | 3/2013 | Holmes et al. |
| 2013/0078625 A1 | 3/2013 | Holmes et al. |
| 2013/0078733 A1 | 3/2013 | Holmes et al. |
| 2013/0079236 A1 | 3/2013 | Holmes |
| 2013/0079599 A1 | 3/2013 | Holmes et al. |
| 2013/0080071 A1 | 3/2013 | Holmes |
| 2013/0190159 A1 | 7/2013 | Watahiki et al. |
| 2013/0220931 A1 | 8/2013 | Petersen et al. |
| 2013/0236907 A1 | 9/2013 | Petersen et al. |
| 2013/0243794 A1 | 9/2013 | Hauser |
| 2013/0244898 A1 | 9/2013 | Burd et al. |
| 2013/0252320 A1 | 9/2013 | Burd et al. |
| 2013/0274139 A1 | 10/2013 | Burd et al. |
| 2013/0280143 A1 | 10/2013 | Zucchelli et al. |
| 2014/0030729 A1 | 1/2014 | Basiji et al. |
| 2014/0045170 A1 | 2/2014 | Patel et al. |
| 2014/0057255 A1 | 2/2014 | Holmes |
| 2014/0057770 A1 | 2/2014 | Holmes et al. |
| 2014/0073043 A1 | 3/2014 | Holmes |
| 2014/0081665 A1 | 3/2014 | Holmes |
| 2014/0141424 A1 | 5/2014 | Pourahmadi et al. |
| 2014/0170678 A1 | 6/2014 | Kasdan et al. |
| 2014/0170688 A1 | 6/2014 | Matje et al. |
| 2014/0170691 A1 | 6/2014 | Ingber et al. |
| 2014/0170735 A1 | 6/2014 | Holmes |
| 2014/0186238 A1 | 7/2014 | Holmes et al. |
| 2014/0229955 A1 | 8/2014 | Holmes et al. |
| 2014/0234949 A1 | 8/2014 | Wasson et al. |
| 2014/0272938 A1 | 9/2014 | Loo et al. |
| 2014/0287955 A1 | 9/2014 | Wende et al. |
| 2014/0295439 A1 | 10/2014 | Patel |
| 2014/0295440 A1 | 10/2014 | Belhocine et al. |
| 2014/0295447 A1 | 10/2014 | Hayashizaki et al. |
| 2014/0296089 A1 | 10/2014 | Holmes et al. |
| 2014/0308661 A1 | 10/2014 | Holmes et al. |
| 2014/0335505 A1 | 11/2014 | Holmes |
| 2014/0335506 A1 | 11/2014 | Burd et al. |
| 2014/0342371 A1 | 11/2014 | Holmes |
| 2015/0072338 A1 | 3/2015 | Holmes |
| 2015/0072362 A1 | 3/2015 | Lui et al. |
| 2015/0072889 A1 | 3/2015 | Lui et al. |
| 2015/0198588 A1 | 7/2015 | Burd et al. |
| 2015/0299777 A1 | 10/2015 | Patel et al. |
| 2015/0338428 A1 | 11/2015 | Holmes et al. |
| 2015/0355169 A1 | 12/2015 | Burd et al. |
| 2015/0368717 A1 | 12/2015 | Holmes et al. |
| 2015/0377871 A1 | 12/2015 | Burd et al. |
| 2015/0377914 A1 | 12/2015 | Burd et al. |
| 2016/0003823 A1 | 1/2016 | Holmes |
| 2016/0011215 A1 | 1/2016 | Holmes |
| 2016/0011225 A1 | 1/2016 | Holmes |

(56) References Cited

U.S. PATENT DOCUMENTS

| | | |
|---|---|---|
| 2016/0025721 A1 | 1/2016 | Burd et al. |
| 2016/0025760 A1 | 1/2016 | Holmes |
| 2016/0025763 A1 | 1/2016 | Holmes |
| 2016/0032361 A1 | 2/2016 | Holmes et al. |
| 2016/0033544 A1 | 2/2016 | Holmes et al. |
| 2016/0054343 A1 | 2/2016 | Holmes |
| 2016/0069919 A1 | 3/2016 | Holmes |
| 2016/0069920 A1 | 3/2016 | Holmes |
| 2016/0069921 A1 | 3/2016 | Holmes |
| 2016/0070884 A1 | 3/2016 | Lui et al. |
| 2016/0077015 A1 | 3/2016 | Holmes et al. |
| 2016/0084863 A1 | 3/2016 | Holmes et al. |
| 2016/0103123 A1 | 4/2016 | Holmes |
| 2016/0124009 A1 | 5/2016 | Wasson et al. |
| 2016/0139138 A1 | 5/2016 | Burd |
| 2016/0161513 A1* | 6/2016 | Burd .................... B01J 19/0046 506/9 |
| 2016/0169880 A1 | 6/2016 | Holmes |
| 2016/0169923 A1 | 6/2016 | Holmes |
| 2016/0216286 A1 | 7/2016 | Holmes |
| 2016/0216287 A1 | 7/2016 | Holmes |
| 2016/0266158 A1* | 9/2016 | Burd .................... B01J 19/0046 |
| 2016/0266163 A1 | 9/2016 | Burd |
| 2016/0320381 A1 | 11/2016 | Holmes |
| 2016/0370396 A1 | 12/2016 | Wasson |
| 2016/0377640 A1 | 12/2016 | Balwani |
| 2018/0111123 A1 | 4/2018 | Chattetjee et al. |

FOREIGN PATENT DOCUMENTS

| | | |
|---|---|---|
| CN | 1253625 A | 5/2000 |
| CN | 1262606 A | 8/2000 |
| CN | 1415964 A | 5/2003 |
| CN | 1416528 A | 5/2003 |
| CN | 2559986 Y | 7/2003 |
| CN | 1499949 A | 5/2004 |
| CN | 1526074 A | 9/2004 |
| CN | 1173776 C | 11/2004 |
| CN | 1572320 A | 2/2005 |
| CN | 1192567 C | 3/2005 |
| CN | 1746675 A | 3/2006 |
| CN | 101010579 A | 8/2007 |
| CN | 101128738 A | 2/2008 |
| CN | 101379386 A | 3/2009 |
| CN | 101490547 A | 7/2009 |
| CN | 101821601 A | 9/2010 |
| CN | 101874205 A | 10/2010 |
| CN | 101878294 A | 11/2010 |
| CN | 101900668 A | 12/2010 |
| CN | 102974474 A | 3/2013 |
| EP | 0410645 A2 | 1/1991 |
| EP | 0478319 A1 | 4/1992 |
| EP | 0541340 A2 | 5/1993 |
| EP | 0564254 A1 | 10/1993 |
| EP | 0571225 A2 | 11/1993 |
| EP | 0576602 A1 | 1/1994 |
| EP | 0631137 A2 | 12/1994 |
| EP | 0636685 A2 | 2/1995 |
| EP | 0637996 A1 | 2/1995 |
| EP | 0637998 A1 | 2/1995 |
| EP | 0639223 A1 | 2/1995 |
| EP | 0640826 A1 | 3/1995 |
| EP | 0640828 A1 | 3/1995 |
| EP | 0652600 A1 | 5/1995 |
| EP | 0684315 A1 | 11/1995 |
| EP | 0684315 A1 | 11/1995 |
| EP | 684315 A1 | 11/1995 |
| EP | 0693560 A2 | 1/1996 |
| EP | 0723146 A1 | 7/1996 |
| EP | 0734017 A1 | 9/1996 |
| EP | 0488761 B1 | 1/1998 |
| EP | 0844475 A2 | 5/1998 |
| EP | 0871034 A2 | 10/1998 |
| EP | 0962773 A1 | 12/1999 |
| EP | 0971039 A2 | 1/2000 |
| EP | 1002229 A1 | 5/2000 |
| EP | 1054250 A1 | 11/2000 |
| EP | 1086719 A1 | 3/2001 |
| EP | 1106244 A2 | 6/2001 |
| EP | 1129783 A | 9/2001 |
| EP | 1174078 A2 | 1/2002 |
| EP | 1202057 A2 | 5/2002 |
| EP | 1203959 A1 | 5/2002 |
| EP | 1225442 A2 | 7/2002 |
| EP | 1221342 A3 | 5/2003 |
| EP | 1346686 A2 | 9/2003 |
| EP | 1353181 A1 | 10/2003 |
| EP | 1360931 A1 | 11/2003 |
| EP | 1415788 A1 | 5/2004 |
| EP | 1498067 A | 1/2005 |
| EP | 1722235 A | 11/2006 |
| EP | 1881329 A2 | 1/2008 |
| EP | 2112514 A | 10/2009 |
| EP | 2112514 A1 | 10/2009 |
| EP | 0828222 B1 | 3/2010 |
| EP | 2259070 A2 | 12/2010 |
| EP | 2264465 A1 | 12/2010 |
| EP | 2298931 B1 | 8/2013 |
| FR | 2498331 A | 7/1982 |
| GB | 1512685 A | 6/1978 |
| JP | 61202142 A | 9/1986 |
| JP | 361202141 A | 9/1986 |
| JP | S 61202141 A | 9/1986 |
| JP | S61254833 A | 11/1986 |
| JP | S 62254034 A | 11/1987 |
| JP | S62254034 A | 11/1987 |
| JP | S6382359 A | 4/1988 |
| JP | S6420453 A | 1/1989 |
| JP | H0275959 A | 3/1990 |
| JP | H03181853 A | 8/1991 |
| JP | 07027700 | 1/1995 |
| JP | H0727700 A | 1/1995 |
| JP | 07083936 A | 3/1995 |
| JP | H07083936 A | 3/1995 |
| JP | H07103959 A | 4/1995 |
| JP | H07120393 A | 5/1995 |
| JP | H07151101 A | 6/1995 |
| JP | H07196314 A | 8/1995 |
| JP | H07304799 A | 11/1995 |
| JP | 8122336 | 5/1996 |
| JP | H08211071 | 8/1996 |
| JP | H08211071 A | 8/1996 |
| JP | H08334505 A | 12/1996 |
| JP | H0968533 A | 3/1997 |
| JP | H0980021 A | 3/1997 |
| JP | H09113511 A | 5/1997 |
| JP | H09192218 A | 7/1997 |
| JP | 2637695 B2 | 8/1997 |
| JP | H09244055 A | 9/1997 |
| JP | H09253056 A | 9/1997 |
| JP | H09281078 A | 10/1997 |
| JP | H1072628 A | 3/1998 |
| JP | H10132712 A | 5/1998 |
| JP | H10239240 A | 9/1998 |
| JP | H10267888 A | 10/1998 |
| JP | H10305016 A | 11/1998 |
| JP | 11037845 A | 2/1999 |
| JP | H11037845 A | 2/1999 |
| JP | H1157560 A | 3/1999 |
| JP | H11352094 A | 12/1999 |
| JP | 2000258341 A | 9/2000 |
| JP | 2000314719 A | 11/2000 |
| JP | 2001065458 A | 3/2001 |
| JP | 2001157855 A | 6/2001 |
| JP | 2001165752 A | 6/2001 |
| JP | 2001174469 A | 6/2001 |
| JP | 2001255272 A | 9/2001 |
| JP | 2001319560 A | 11/2001 |
| JP | 2002010990 A | 1/2002 |
| JP | 2002031055 A | 1/2002 |
| JP | 2002041654 A | 2/2002 |
| JP | 2002044007 A | 2/2002 |
| JP | 2002161856 A | 6/2002 |

(56) References Cited

FOREIGN PATENT DOCUMENTS

| | | |
|---|---|---|
| JP | 2002196011 A | 7/2002 |
| JP | 2002263185 A | 9/2002 |
| JP | 2002266762 A | 9/2002 |
| JP | 2002282217 A | 10/2002 |
| JP | 2002538440 A | 11/2002 |
| JP | 2002371955 A | 12/2002 |
| JP | 2003057244 A | 2/2003 |
| JP | 2003504618 A | 2/2003 |
| JP | 2003166910 A | 6/2003 |
| JP | 2003166910 A | 6/2003 |
| JP | 2003167960 A | 6/2003 |
| JP | 2003207454 A | 7/2003 |
| JP | 2003222611 A | 8/2003 |
| JP | 2003315348 A | 11/2003 |
| JP | 2003322653 A | 11/2003 |
| JP | 2003329696 A | 11/2003 |
| JP | 2004028589 A | 1/2004 |
| JP | 2004101381 A | 4/2004 |
| JP | 2004317498 A | 11/2004 |
| JP | 2004333452 A | 11/2004 |
| JP | 2004358261 A | 12/2004 |
| JP | 2005010179 A | 1/2005 |
| JP | 2005015243 A | 1/2005 |
| JP | 2005030983 A | 2/2005 |
| JP | 2005104750 A | 4/2005 |
| JP | 2005130855 A | 5/2005 |
| JP | 2005140681 A | 6/2005 |
| JP | 2005291954 A | 10/2005 |
| JP | 2006010363 A | 1/2006 |
| JP | 2006125855 A | 5/2006 |
| JP | 2006184009 A | 7/2006 |
| JP | 2006276003 A | 10/2006 |
| JP | 2007017354 A | 1/2007 |
| JP | 2007178328 A | 7/2007 |
| JP | 2007187677 A | 7/2007 |
| JP | 2007322324 A | 12/2007 |
| JP | 2008064701 A | 3/2008 |
| JP | 2008298494 A | 12/2008 |
| JP | 2009002816 A | 1/2009 |
| JP | 2010025937 A | 2/2010 |
| JP | 2010175342 A | 8/2010 |
| JP | 2011174746 A | 9/2011 |
| JP | 2016197106 A | 11/2016 |
| RU | 2147123 C1 | 3/2000 |
| RU | 2148438 C1 | 5/2000 |
| RU | 2179887 C1 | 2/2002 |
| RU | 2237426 C2 | 10/2004 |
| SU | 598649 A | 3/1978 |
| SU | 1722603 A | 3/1992 |
| TW | 265262 B | 12/1995 |
| WO | 9949019 A2 | 9/1990 |
| WO | 9013668 A1 | 11/1990 |
| WO | 9215673 A1 | 9/1992 |
| WO | 9507463 A | 3/1995 |
| WO | 9508774 A2 | 3/1995 |
| WO | 9603637 A1 | 2/1996 |
| WO | 9735171 A1 | 9/1997 |
| WO | 9814605 A1 | 4/1998 |
| WO | 9826277 A2 | 6/1998 |
| WO | 1998038510 A3 | 1/1999 |
| WO | 1999004043 A1 | 1/1999 |
| WO | 0049176 A1 | 8/2000 |
| WO | WO 00/78454 A1 | 12/2000 |
| WO | 0104600 A | 1/2001 |
| WO | WO 01/13127 A1 | 2/2001 |
| WO | 2002044703 A2 | 6/2002 |
| WO | 02064038 A | 8/2002 |
| WO | WO 02/064038 A2 | 8/2002 |
| WO | WO 02/064826 A2 | 8/2002 |
| WO | 2002090995 A2 | 11/2002 |
| WO | 2004055198 A2 | 7/2004 |
| WO | 2004059312 A1 | 7/2004 |
| WO | 2004112602 A1 | 12/2004 |
| WO | 2005024437 A1 | 3/2005 |
| WO | 2005025413 A2 | 3/2005 |
| WO | 2005065157 A2 | 7/2005 |
| WO | 2005065538 A2 | 7/2005 |
| WO | 2005072145 A2 | 8/2005 |
| WO | WO2005074161 A1 | 8/2005 |
| WO | 2005121780 A2 | 12/2005 |
| WO | 2006090154 A | 8/2006 |
| WO | 2006120656 A1 | 11/2006 |
| WO | 2006121510 A2 | 11/2006 |
| WO | 2007002579 A | 1/2007 |
| WO | WO 2007/092713 A2 | 8/2007 |
| WO | 2008050254 A1 | 5/2008 |
| WO | 2008115632 A2 | 9/2008 |
| WO | 2008010759 | 3/2009 |
| WO | 2009046227 A1 | 4/2009 |
| WO | 2009114333 A2 | 9/2009 |
| WO | WO 2009/114333 A2 | 9/2009 |
| WO | 2009130309 A1 | 10/2009 |
| WO | 2011106315 A1 | 9/2011 |
| WO | 2011106512 A | 9/2011 |
| WO | 2012040641 A | 3/2012 |
| WO | 2012054589 A2 | 4/2012 |
| WO | 2012054638 A2 | 4/2012 |
| WO | 2012054639 A2 | 4/2012 |
| WO | 2012069925 A1 | 5/2012 |
| WO | 2010090857 | 6/2012 |
| WO | 2012100235 A | 7/2012 |
| WO | 2013043203 A2 | 3/2013 |
| WO | 2013052318 A1 | 4/2013 |
| WO | 2013148866 A1 | 10/2013 |
| WO | 2014004573 A1 | 1/2014 |
| WO | 2014015199 A1 | 1/2014 |
| WO | 2014127379 A1 | 8/2014 |
| WO | 2015035256 A2 | 3/2015 |

OTHER PUBLICATIONS

Notice of Allowance dated Aug. 22, 2016 for U.S. Appl. No. 13/244,949.
Notice of Allowance dated Aug. 22, 2016 for U.S. Appl. No. 14/479,241.
Office Action dated Jun. 30, 2016 for U.S. Appl. No. 14/872,718.
Office Action dated Jul. 14, 2016 for U.S. Appl. No. 14/848,032.
Office Action dated Aug. 18, 2016 for U.S. Appl. No. 14/831,838.
Office Action dated Aug. 8, 2016 for U.S. Appl. No. 13/244,950.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Abbott. FDA Clears Abbott's i-STAT 1 Wireless Point of Care Testing System. Press release dated Mar. 29, 2011.
Abbott. Procedure Manual for the i-STAT System. Rev. dated Jul. 12, 2004.
Abbott. Testing Cartridges for the i-STAT System. Rev. B. 06/09. Available at http://www.abbottpointofcare.com/PDFs/17845_CrtrdgeBrochure_M1.pdf. Accessed Sep. 13, 2011.
Advisory Action dated Sep. 25, 2015 for U.S. Appl. No. 14/479,241.
Anders et al., Am Journal Med Hyg 87(1), 2012, pp. 165-170.
AppliedBiosystems StepOne Real-Time PCR System Manual, Rev. 2010.
B. Rodriguez-Sanchez et al. Improved Diagnosis for Nine Viral Diseases Considered as Notifiable by the World Organization for Animal Health. Transbound Emerg Dis. Aug. 2008; 55(5-6): 215-25.
Botstein, et al. Construction of a genetic linkage map in man using restriction fragment length polymorphisms. Am J Hum Genet. May 1980;32(3):314-31.
Bruggemann, et al. Production of human antibody repertoires in transgenic mice. Curr Opin Biotechnol. 1997; 8(4):455-458.
Carter, et al. Humanization of an anti-p185HER2 antibody for human cancer therapy. Proc. Natl. Acad. Sci. USA. 1992;89(10):4285-9.
Chantreuil J. et al. "Artial chaotic tachycardia during a respiratory tract infection due to NL63 coronavirus". Arch Pediatr, Mar. 2013; 20(3):pp. 278-281, abstract.

(56) References Cited

OTHER PUBLICATIONS

Chin et al. Low-Cost Microdevices for Point-of-Care Testing. Biological and Medical Physics, Biomedical Engineering pp. 3-21. Oct. 12, 2012.
Dapat I.C. et al. Genetic characterization of human influenza viruses in the pandemic (2009-2010) and post-pandemic (2010-2011) periods in Japan. PLoS One, 2012; 7(6):e36455.
Di Serio, et al. Integration between the tele-cardiology unit and the central laboratory: methodological and clinical evaluation of point-of-care testing cardiac marker in the ambulance. Clin Chem Lab Med. 2006;44(6):768-73.
Diamandis. Theranos phenomenon: promises and fallacies. Clin Chem Lab Med. Jun. 2015;53(7):989-93.
Dzenitis, Presentation of Autonomous Pathogen Detection System, Lawrence Livermore National Laboratory, Aug. 21, 2006, Washington, DC, UCRL-PRES-22311.
ebm Industries, Inc. Motor Design, Quality and Performance are Critical to Reliable Operation of Fans and Blowers. pp. 15-17. emb Industries, Inc. 1995, 1996, 1997, 1999.
European search report and opinion dated Sep. 18, 2013 for Application No. 13178059.5.
European search report dated Aug. 31, 2010 for Application No. 8836072.2.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
Gibbons, et al. Patient-side immunoassay system with a single-use cartridge for measuring analytes in blood. Clin Chem. Sep. 1989;35(9):1869-73.
Gill, et al. Nucleic acid isothermal amplification technologies: a review. Nucleosides, Nucleotides and Nucleic Acids. Mar. 2008; 27(3):224-43.
Griffiths, et al. Strategies for selection of antibodies by phage display. Curr Opin Biotechnol. Feb. 1998;9(1):102-8.
Guatelli, et al. Isothermal, in vitro amplification of nucleic acids by a multienzyme reaction modeled after retroviral replication. Proc. Natl. Acad. Sci. USA. 1990;87:1874-1878.
Havlickova M et al. Influenza virus detection in clinical specimens. Abstract. Acta Virol. Sep. 1990;34(5):449-56.
Health Buddy device. Available at http://www.3hc.org/images/2009%20images/health-buddy-appliance.gif. Accessed Aug. 26, 2011.
Health Buddy Health Management Programs. Available at http://www.bosch-telehealth.com/content/language1/img_zoom/health_buddy_system_gif. Accessed Aug. 26, 2011.
Hung et al. Effect of clinical and virological parameters on the level of neutralizing antibody against pandemic influenza A virus H1N1 2009. Clin Infect Dis. Aug. 1, 2010;51(3):274-9.
International Search Report and Written Opinion dated Jan. 16, 2014 for Application No. PCT/US2013/061485.
International search report and written opinion dated Jan. 18, 2012 for PCT/US2011/053189.
International search report and written opinion dated Jan. 20, 2012 for PCT/US2011/053188.
International search report and written opinion dated Nov. 5, 2012 for PCT/US2012/057093.
International search report and written opinion dated Feb. 6, 2013 for PCT/US2012/057155.
International Search Report and Written Opinion dated Jun. 19, 2014 for PCT/US2014/016997.
International search report and written opinion dated Aug. 3, 2012 for PCT/US2012/022130.
International search report and written opinion dated Sep. 16, 2008 for PCT/US2007/009878.
International search report dated Dec. 5, 2008 for PCT Application No. US2008/78636.
Jannetto et al. Real-Time Detection of Influenza A, Influenza B, and Respiratory Syncytial Virus A and B in Respiratory Specimens by Use of Nanoparticle Probes. J Clin Microbiol. Nov. 2010;48(11):3997-4002. Epub Sep. 8, 2010.
Jones, et al. Replacing the complementarity-determining regions in a human antibody with those from a mouse. Nature. 1986;321:522-525.
Kautner et al., Journal of Pediatrics, 1997, 131, pp. 516-524.
Khan, et al. Detection of influenza virus neuraminidase-specific antibodies by an enzyme-linked immunosorbent assay. J Clin Microbiol. Jul. 1982;16(1): 115-22.
Kimura Y et al. Tail variation of the folding primer effects the SmartAmp2 process differently. Biochem Biophys Res Commun. Jun. 12, 2009;383(4):455-9.
Kwok, et al. Increasing the information content of STS-based genome maps: identifying polymorphisms in mapped STSs. Genomics. Jan. 1, 1996;31(1):123-6.
Landgren. Molecular mechanics of nucleic acid sequence amplification. Trends Genet. Jun. 1993;9(6):199-204.
Lee, et al. Nucleic Acid Amplication Technologies. 1997. (Textbook).
Li, Peng. (2012) Microfluidics for IVD: In Pursuit of the Holy Grail. J Bioengineer & Biomedical Sci S8:e001.
Little, et al. Of mice and men: hybridoma and recombinant antibodies. Immunol Today. Aug. 2000;21(8):364-70.
Lizardi, et al. Exponential amplification of recombinant-RNA hybridization probes. BioTechnol. 1988; 6:1197-1202.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Lounsbury et al., Lab Chip, 2013, 13, pp. 1384-1393.
Luk F.O. et al. A case of dengue maculopathy with spontaneous recovery. Case Rep Ophthalmol, Jun. 8, 2013;4(2):pp. 28-33.
Mahony et al. Molecular diagnosis of respiratory virus infections. Crit Rev Clin Lab Sci. Sep.-Dec. 2011;48(5-6):217-49.
Metzgar D. et al. Single assay for simultaneous detection and differential identification of human and avian influenza virus types, subtypes, and emergent variants. PLoS One. Feb. 3, 2010;5(2):e8995.
Notice of Allowance dated Jan. 12, 2016 for U.S. Appl. No. 14/670,200.
Notice of Allowance dated Jan. 14, 2016 for U.S. Appl. No. 13/326,023.
Notice of Allowance dated Nov. 20, 2015 for U.S. Appl. No. 13/244,956.
Notice of Allowance dated Dec. 15, 2014 for U.S. Appl. No. 14/339,946.
Notice of Allowance dated Feb. 5, 2016 for U.S. Appl. No. 13/244,949.
Notice of Allowance dated May 29, 2015 for U.S. Appl. No. 14/480,960.
Notice of Allowance dated May 6, 2015 for U.S. Appl. No. 13/893,258.
Notice of Allowance dated Jun. 6, 2016 for U.S. Appl. No. 14/479,245.
Notice of Allowance dated Jun. 6, 2016 for U.S. Appl. No. 14/562,066.
Notice of Allowance dated Jul. 19, 2016 for U.S. Appl. No. 15/007,585.
Notice of Allowance dated Aug. 11, 2014 for U.S. Appl. No. 13/244,954.
Notice of Allowance issued for U.S. Appl. No. 13/916,553 dated Dec. 20, 2013.
Obryadina A.P. et al, "Avidnost antitel v diagnostike infektsionnykh zabolevaniy" Laboratornaya diagnostika infektsionnykh zabolevaniy, 2007, No. 4, p. 3-7 (with English translation).
O'Connor, et al. Humanization of an antibody against human protein C and calcium-dependence involving framework residues. Protein Eng. 1998; 11(4):321-8.
Office Action dated Jan. 11, 2012 for U.S. Appl. No. 13/244,951.
Office Action dated Jan. 12, 2016 for U.S. Appl. No. 13/647,325.
Office Action dated Jan. 13, 2015 for U.S. Appl. No. 13/647,325.
Office Action dated Jan. 14, 2014 for U.S. Appl. No. 13/893,258.
Office Action dated Jan. 19, 2011 for U.S. Appl. No. 12/244,723.
Office Action dated Jan. 19, 2012 for U.S. Appl. No. 13/244,956.

(56) References Cited

OTHER PUBLICATIONS

Office Action dated Jan. 21, 2016 for U.S. Appl. No. 14/789,967.
Office Action dated Jan. 23, 2013 for U.S. Appl. No. 13/355,458.
Office Action dated Jan. 24, 2012 for Application No. MX/a/2010/003578.
Office Action dated Jan. 27, 2012 for U.S. Appl. No. 13/244,946.
Office Action dated Jan. 29, 2015 for U.S. Appl. No. 13/893,258.
Office Action dated Jan. 29, 2015 for U.S. Appl. No. 14/479,241.
Office Action dated Jan. 3, 2012 for Application No. SG201002319-0.
Office Action dated Jan. 5, 2016 for U.S. Appl. No. 14/831,734.
Office Action dated Oct. 17, 2011 for Application No. MX/a/2010/003578.
Office Action dated Oct. 25, 2012 for Application No. SG201002319-0.
Office Action dated Nov. 12, 2014 for U.S. Appl. No. 14/479,245.
Office Action dated Nov. 12, 2015 for U.S. Appl. No. 14/562,066.
Office Action dated Nov. 15, 2012 for Application No. JP2010-528139.
Office Action dated Nov. 19, 2015 for U.S. Appl. No. 14/604,194.
Office Action dated Nov. 24, 2015 for U.S. Appl. No. 14/831,838.
Office Action dated Nov. 4, 2015 for U.S. Appl. No. 13/933,035.
Office Action dated Nov. 6, 2012 for U.S. Appl. No. 13/244,954.
Office Action dated Nov. 6, 2013 for U.S. Appl. No. 13/916,553.
Office Action dated Dec. 3, 2015 for U.S. Appl. No. 14/848,032.
Office Action dated Dec. 4, 2015 for U.S. Appl. No. 14/670,200.
Office Action dated Feb. 12, 2015 for U.S. Appl. No. 14/479,190.
Office Action dated Feb. 15, 2012 for U.S. Appl. No. 13/244,952.
Office Action dated Feb. 20, 2014 for U.S. Appl. No. 13/764,642.
Office Action dated Feb. 24, 2012 for U.S. Appl. No. 13/244,954.
Office Action dated Feb. 24, 2016 for U.S. Appl. No. 14/479,245.
Office Action dated Feb. 24, 2016 for U.S. Appl. No. 14/848,084.
Office Action dated Feb. 29, 2016 for U.S. Appl. No. 13/244,950.
Office Action dated Mar. 1, 2012 for U.S. Appl. No. 13/244,953.
Office Action dated Mar. 12, 2012 for Application No. IL204877.
Office Action dated Mar. 12, 2012 for U.S. Appl. No. 13/244,947.
Office Action dated Mar. 21, 2012 for U.S. Appl. No. 13/244,950.
Office Action dated Mar. 22, 2012 for U.S. Appl. No. 13/244,949.
Office Action dated Mar. 25, 2014 for U.S. Appl. No. 13/889,674.
Office Action dated Mar. 26, 2012 for U.S. Appl. No. 13/244,836.
Office Action dated Mar. 8, 2016 for U.S. Appl. No. 14/604,194.
Office Action dated Apr. 17, 2012 for U.S. Appl. No. 13/244,952.
Office Action dated Apr. 18, 2016 for U.S. Appl. No. 14/479,241.
Office Action dated Apr. 22, 2015 for U.S. Appl. No. 13/244,956.
Office Action dated Apr. 3, 2015 for U.S. Appl. No. 14/479,245.
Office Action dated Apr. 6, 2015 for U.S. Appl. No. 13/244,950.
Office Action dated Apr. 7, 2016 for U.S. Appl. No. 15/007,585.
Office Action dated May 10, 2016 for U.S. Appl. No. 14/793,625.
Office Action dated May 19, 2016 for U.S. Appl. No. 14/831,734.
Office Action dated Jun. 12, 2015 for U.S. Appl. No. 13/326,023.
Office Action dated Jun. 18, 2012 for U.S. Appl. No. 13/244,951.
Office Action dated Jun. 19, 2015 for U.S. Appl. No. 13/647,325.
Office Action dated Jun. 20, 2012 for U.S. Appl. No. 13/244,946.
Office Action dated Jun. 21, 2011 for Application No. NZ584963.
Office Action dated Jun. 22, 2012 for Application No. EP 8836072.2.
Office Action dated Jun. 29, 2012 for Application No. CN 200880118646.2.
Office Action dated Jun. 9, 2010 for U.S. Appl. No. 12/244,723.
Office Action dated Jul. 13, 2012 for U.S. Appl. No. 13/244,836.
Office Action dated Jul. 13, 2012 for U.S. Appl. No. 13/244,956.
Office Action dated Jul. 18, 2013 for U.S. Appl. No. 13/893,258.
Office Action dated Jul. 24, 2012 for U.S. Appl. No. 13/244,947.
Office Action dated Jul. 28, 2014 for U.S. Appl. No. 13/244,949.
Office Action dated Jul. 7, 2014 for U.S. Appl. No. 13/769,779.
Office Action dated Jul. 8, 2014 for U.S. Appl. No. 13/335,458.
Office Action dated Jul. 8, 2014 for U.S. Appl. No. 14/157,343.
Office Action dated Jul. 8, 2015 for U.S. Appl. No. 14/479,241.
Office Action dated Aug. 1, 2012 for U.S. Appl. No. 13/244,949.
Office Action dated Aug. 16, 2012 for U.S. Appl. No. 13/244,950.
Office Action dated Aug. 16, 2012 for U.S. Appl. No. 13/244,953.
Office Action dated Aug. 22, 2014 for U.S. Appl. No. 13/244,950.
Office Action dated Sep. 18, 2014 for U.S. Appl. No. 14/339,946.
Office Action dated Sep. 24, 2015 for U.S. Appl. No. 14/479,245.
Office Action dated Sep. 26, 2013 for U.S. Appl. No. 13/889,674.
Office Action dated Sep. 8, 2014 for U.S. Appl. No. 13/244,956.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Papautsky, et al. Micromachined pipette arrays. IEEE Trans Biomed Eng. Jun. 2000;47(6):812-9.
Plebani. Evaluating and using innovative technologies: a lesson from Theranos? Clin Chem Lab Med. Jun. 2015;53(7):961-2.
Preliminary Amendment filed Jul. 1, 2015 for U.S. Appl. No. 14/789,967.
Queen, et al. A humanized antibody that binds to the interleukin 2 receptor. Proc. Natl. Acad. Sci. USA. 1989; 86(24):10029-33.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-issues-following-cms-investigation.html.
Ray, et al. Distinct hemagglutinin and neuraminidase epitopes involved in antigenic variation of recent human parainfluenza virus type 2 isolates. Virus Res. Jun. 1992;24(1):107-13.
Resch-Genger, Ute, et al., "Quantum dots versus organic dyes as fluorescent labels," Sep. 2008, Nature Methods, 5, pp. 763-775.
Restriction Requirement dated Aug. 1, 2013 for U.S. Appl. No. 13/916,553.
Restriction Requirement dated Aug. 26, 2013 for U.S. Appl. No. 13/916,533.
Riechmann, et al. Reshaping human antibodies for therapy. Nature. Mar. 24, 1988;332(6162):323-7.
Roskos et al. Simple System for Isothermal DNA Amplification Coupled to Lateral Flow Detection. Plos One. Jul. 26, 2013;8(7):e69335. Print 2013.
Rouzic. Contamination-pipetting: relative efficiency of filter tips compared to Microman(R) postitive displacement pipette. Nature Methods (2006) 3 iii-iv.
Sahni et al. Reverse transcription loop-mediated isothermal amplification (RT-LAMP) for diagnosis of dengue. Med J Armed Forces India. Jul. 2013; 69(3):246-53. doi: 10.1016/j.mjafi.2012.07.017. Epub Dec. 1, 2012.
Sakas. Trends in Medical Imaging from 2D to 3D. Computers and Graphics. 2002;26:577-587.
Singapore combined search report/examination dated Jan. 3, 2012 for Application No. 201002319.
Tautz. Hypervariability of simple sequences as a general source for polymorphic DNA markers. Nucleic Acids Res. Aug. 25, 1989;17(16):6463-71.
Thermo Scientific: Thermo Scientific Heraeus Labofuge 400 and 400 R Centrifuges Great value and performance for averyday use in the lab, Jan. 1, 2008.
Tholouli, Eleni, et al., "Imaging of multiple mRNA targets using quantum dot based in situ hybridization and spectral deconvolution in clinical biopsies," Jul. 31, 2006, Biochemical and Biophysical Research Communications, 348, pp. 628-636.
U.S. Appl. No. 13/896,171, filed May 16, 2013. Inventors: Holmes, et al.
U.S. Appl. No. 14/050,235, filed Oct. 9, 2013. Inventors: Holmes, et al.
U.S. Appl. No. 60/997,460, filed Oct. 2, 2007. Inventors: Burd et al.
U.S. Appl. No. 61/435,250, filed Jan. 21, 2011. Inventors: Gibbons et al.
U.S. Appl. No. 61/766,113, filed Feb. 18, 2013.
U.S. Appl. No. 61/766,119, filed Feb. 18, 2013.
U.S. Appl. No. 61/805,923, filed Mar. 27, 2013.
Verhoeyen, et al. Reshaping human antibodies: grafting an antilysozyme activity. Science. 1988;239:1534-1536.

(56) References Cited

OTHER PUBLICATIONS

Von Lode, P. Point-of-care immunotesting: approaching the analytical performance of central laboratory methods. Clin Biochem. Jul. 2005;38(7):591-606.
Vos, et al. AFLP: a new technique for DNA fingerprinting. Nucleic Acids Res. Nov. 11, 1995;23(21):4407-14.
Voudoukis et al., 2011, Med Sci Monit, 17(4), pp. 185-188.
Wang Y. et al. "Methicillin resistant *Staphyloccus aureus* infection: a case report and literature review". Zhonghua Jie He Hu Xi Za Zhi, Sep. 2009; 32(9):pp. 665-659, abstract.
Weber, et al. Abundant class of human DNA polymorphisms which can be typed using the polymerase chain reaction. Am J Hum Genet. Mar. 1989;44(3):388-96.
Wikipedia. Electric motor. Available at http://en.wikipedia.org/wiki/Electric_motor. Accessed May 22, 2012.
Wikipedia. Outrunner. Available at http://en.wikipedia.org/wiki/Outrunner. Accessed May 22, 2012.
Williams, et al. DNA polymorphisms amplified by arbitrary primers are useful as genetic markers. Nucleic Acids Res. Nov. 25, 1990;18(22):6531-5.
World Health Organization (WHO) Guide to Field Operations, Oct. 2006, pp. 1-80.
Written Opinion and International Search Report dated Dec. 18, 2014 for PCT/US2014/054424.
Zhao et al. Phylogenetic distribution and genetic mapping of a (GGC)n microsatellite from rice (*Oryza sativa* L.). Plant Mol Biol. Feb. 1993;21(4):607-14.
Zietkiewicz, et al. Genome fingerprinting by simple sequence repeat (SSR)—anchored polymerase chain reaction amplification. Genomics. Mar. 15, 1994;20(2)176-83.
Zimmerman O et al. C-reactive protein serum levels as an early predictor of outcome in patients with pandemic H1N1 influenza A virus infection. BMC Infect Dis. Oct. 4, 2010;10:288.
Office Action dated Mar. 2, 2017 for U.S. Appl. No. 14/918,090.
Advisory Action dated Apr. 29, 2016 for U.S. Appl. No. 14/183,500.
Advisory Action dated Aug. 19, 2016 for U.S. Appl. No. 14/839,749.
Advisory Action dated Aug. 19, 2016 for U.S. Appl. No. 14/855,303.
Advisory Action dated Aug. 3, 2016 for U.S. Appl. No. 14/857,407.
Advisory Action dated Aug. 8, 2016 for U.S. Appl. No. 14/857,224.
Advisory Action dated Sep. 15, 2016 for U.S. Appl. No. 14/918,090.
Allain, Charles C. et al. Enzymatic determination of total serum cholesterol. Clinical Chemistry (1974) 20 470-475.
BD Max System User's Manual, Sep. 2012.
Dinca et al. Fast and accurate temperature control of a PCT microsystem with a disposable reactor, J. Micromech. Microeng. 19 (2009).
Drosten et al. Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription-PCR, J Clin Microbial, Jul. 2002, 40(7), 2323-2330.
Examiner's Answer to Appeal Brief dated Feb. 26, 2016 for U.S. Appl. No. 14/157,343.
Godolphin et al. Automated blood-sample handling in the clinical laboratory. Clinical Chemistry (1990) 36 1551-1555.
International Search Report and Written Opinion dated Jun. 19, 2014 for Application No. PCT/US2014/016548.
Ma et al. Study of ELISA Technique, Nature and Science, 4(2), 2006, Ma, ELISA Technique.
Martin, David H. et al. Use of multiple acid amplification tests to define the infected-patient "gold standard" in clinical trials of new diagnostic tests for Chlamydia trachomatis infections. J. Clinical Microbiology (2004) 42 4749-4758.
Niemz, et al. Nucleic acid testing for tuberculosis at the point-of-care in high-burden countries. Expert Rev Mol Diagn. Sep. 2012 ; 12(7): 687-701.
Notice of Allowance dated Jan. 13, 2017 for U.S. Appl. No. 14/872,919.
Notice of Allowance dated Jan. 5, 2017 for U.S. Appl. No. 14/859,064.
Notice of Allowance dated Oct. 3, 2016 for U.S. Appl. No. 13/769,820.
Notice of Allowance dated Oct. 7, 2016 for U.S. Appl. No. 14/789,967.
Notice of Allowance dated Nov. 12, 2015 for U.S. Appl. No. 13/769,779.
Notice of Allowance dated Dec. 2, 2016 for U.S. Appl. No. 15/007,585.
Notice of Allowance dated Dec. 9, 2016 for U.S. Appl. No. 13/933,035.
Notice of Allowance dated Sep. 28, 2016 for U.S. Appl. No. 14/831,734.
Niwakanma, et al. Quantitative detection of plasmodium falciparum NDA in saliva, blood, and urine. Journal of Infectious Diseases (2009) 199 1567-1574.
Office Action dated Jan. 11, 2016 for U.S. Appl. No. 14/829,572.
Office Action dated Jan. 12, 2016 for U.S. Appl. No. 14/857,224.
Office Action dated Jan. 13, 2016 for U.S. Appl. No. 14/857,407.
Office Action dated Jan. 21, 2016 for U.S. Appl. No. 14/183,503.
Office Action dated Jan. 3, 2017 for U.S. Appl. No. 15/160,578.
Office Action dated Jan. 9, 2015 for U.S. Appl. No. 14/157,343.
Office Action dated Oct. 20, 2016 for U.S. Appl. No. 14/848,032.
Office Action dated Oct. 26, 2016 for U.S. Appl. No. 14/793,625.
Office Action dated Oct. 31, 2016 for U.S. Appl. No. 14/918,090.
Office Action dated Nov. 17, 2015 for U.S. Appl. No. 13/945,202.
Office Action dated Nov. 17, 2016 for U.S. Appl. No. 14/965,665.
Office Action dated Nov. 18, 2016 for U.S. Appl. No. 15/005,897.
Office Action dated Nov. 8, 2016 for U.S. Appl. No. 14/604,194.
Office Action dated Dec. 15, 2015 for U.S. Appl. No. 14/848,775.
Office Action dated Dec. 15, 2016 for U.S. Appl. No. 14/183,500.
Office Action dated Dec. 17, 2015 for U.S. Appl. No. 14/860,149.
Office Action dated Dec. 18, 2015 for U.S. Appl. No. 14/860,048.
Office Action dated Dec. 18, 2015 for U.S. Appl. No. 14/872,919.
Office Action dated Dec. 28, 2016 for U.S. Appl. No. 14/872,718.
Office Action dated Dec. 29, 2016 for U.S. Appl. No. 15/041,421.
Office Action dated Dec. 30, 2016 for U.S. Appl. No. 14/848,084.
Office Action dated Dec. 7, 2015 for U.S. Appl. No. 14/859,064.
Office Action dated U.S. Appl. No. 14/183,500 dated Jun. 6, 2016 for U.S. Appl. No. 14/183,500.
Office Action dated Feb. 23, 2016 for U.S. Appl. No. 14/183,500.
Office Action dated Feb. 4, 2016 for U.S. Appl. No. 13/769,820.
Office Action dated Feb. 4, 2016 for U.S. Appl. No. 14/839,749.
Office Action dated Feb. 8, 2016 for U.S. Appl. No. 14/855,303.
Office Action dated Feb. 9, 2017 for U.S. Appl. No. 14/831,838.
Office Action dated Mar. 22, 2016 for U.S. Appl. No. 14/918,090.
Office Action dated Apr. 20, 2015 for U.S. Appl. No. 13/769,779.
Office Action dated Apr. 29, 2015 for U.S. Appl. No. 13/769,820.
Office Action dated May 12, 2016 for U.S. Appl. No. 13/769,820.
Office Action dated May 13, 2016 for U.S. Appl. No. 14/857,224.
Office Action dated May 16, 2016 for U.S. Appl. No. 14/857,407.
Office Action dated Jun. 10, 2016 for U.S. Appl. No. 14/839,749.
Office Action dated Jun. 10, 2016 for U.S. Appl. No. 14/855,303.
Office Action dated Jun. 10, 2016 for U.S. Appl. No. 14/859,064.
Office Action dated Jun. 17, 2016 for U.S. Appl. No. 14/872,919.
Office Action dated Jun. 19, 2015 for U.S. Appl. No. 14/183,500.
Office Action dated Jun. 24, 2016 for U.S. Appl. No. 14/860,048.
Office Action dated Jun. 3, 2016 for U.S. Appl. No. 13/945,202.
Office Action dated Jun. 9, 2016 for U.S. Appl. No. 13/933,035.
Office Action dated Jul. 1, 2016 for U.S. Appl. No. 14/848,775.
Office Action dated Jul. 1, 2016 for U.S. Appl. No. 14/860,149.
Office Action dated Jul. 14, 2016 for U.S. Appl. No. 14/829,572.
Office Action dated Jul. 27, 2016 for U.S. Appl. No. 15/160,578.
Office Action dated Jul. 8, 2016 for U.S. Appl. No. 14/918,090.
Office Action dated Aug. 15, 2016 for U.S. Appl. No. 14/183,503.
Office Action dated Aug. 15, 2016 for U.S. Appl. No. 14/789,920.
Office Action dated Aug. 24, 2016 for U.S. Appl. No. 14/848,084.
Office Action dated Aug. 25, 2016 for U.S. Appl. No. 14/872,995.
Office Action dated Aug. 26, 2016 for U.S. Appl. No. 14/789,930.
Office Action dated Sep. 13, 2016 for U.S. Appl. No. 14/831,734.
Office Action dated Sep. 13, 2016 for U.S. Appl. No. 14/965,725.
Office Action dated Sep. 19, 2016 for U.S. Appl. No. 14/839,749.
Office Action dated Sep. 19, 2016 for U.S. Appl. No. 14/855,303.
Office Action dated Sep. 2, 2014 for U.S. Appl. No. 13/769,820.
Office Action dated Sep. 2, 2016 for U.S. Appl. No. 14/857,224.
Office Action dated Sep. 30, 2016 for U.S. Appl. No. 13/647,325.
Office Action dated Sep. 7, 2016 for U.S. Appl. No. 14/857,407.

(56) References Cited

OTHER PUBLICATIONS

Pacaniello. Detection of antigens or antibodies by ELISA, Jul. 16, 2010, published by Virology Blog. Downloaded by USPTO Examiner on Jan 5, 2016 from http://www.virology.ws/2010/07/16/detection-of-antigens-or-antibodies-by-elisa/.

Ramamritham K. et al. "Scheduling algorithms and operating systems support for real-time systems." Proceedings of the IEEE, 1994; 82(1): 55-67, especially pp. 57-58.

Schembri, et al. Centrifugation and capillarity integrated into a multiple analyte whole blood analyser, Journal of Automatic Chemistry, vol. 17, No. 3 (May-Jun. 1995), pp. 99-104.

Teles, Fernando S. R. R. Biosensors and rapid diagnostic tests on the frontier between analytical and clinical chemistry for biomolecular diagnosis of dengue disease: A review. Analytical Chimica Acta (2011) 687 28-42.

The International Search Report and the Written Opinion for Application No. PCT/US2013/051170.

The International Search Report and Written Opinion dated May 28, 2015 for PCT/US2015/012541.

Van Ierssel, et al., Flow cytometric detectopm of endothelial microparticles (EMP): Effects of centrifugation and storage alter with the phenotype studied, Thrombosis Research 125 (2010) 332-339.

Webb et al. Vascular endothelial growth factor (VEGF) is released from platelets during blood clotting: implications for measurement of circulating VEGF levels in clinical disease, Clinical Science (1998) 94,395-404 (printed in Great Britain).

Xie Z. et al, "A new algorithm for complex product flexible scheduling with constraint between jobs." Computers & Industrial Engineering, 2009; 57: 766-772. doi:10.1016/j.cie.2009.02.004.

Belgrader et al. A battery-powered notebook thermal cycler for rapid multiplex real-time PCR analysis. Analytical Chemistry (2001) 73 286-289.

Draw et al. Isothermal nucleic acid amplification technologies for point-of-care diagnostics: a critical review, Lab On a Chip, vol. 12, No. 14, Jul. 1, 2012.

Horton et al. Engineering hybrid genes without the use of restriction enzymes: gene splicing byoverlap extension. Sene, Elsevier, Amsterdam, NL, vol. 77, No. 1, Apr. 15, 1989, pp. 61-68.

Notice of Allowance dated Jul. 3, 17 for U.S. Appl. No. 15/162,038.
Office Action dated Oct. 6, 2017 for U.S. Appl. No. 14/848,084.
Office Action dated Nov. 16, 2017 for U.S. Appl. No. 14/831,838.
Office Action dated Dec. 15, 2017 for U.S. Appl. No. 14/789,930.
Office Action dated Dec. 6, 2017 for U.S. Appl. No. 14/855,303.
Office Action dated Mar. 29, 2017 for U.S. Appl. No. 14/789,904.
Office Action dated Apr. 7, 2017 for U.S. Appl. No. 14/860,048.
Office Action dated Apr. 7, 2017 for U.S. Appl. No. 14/860,149.
Office Action dated May 16, 2017 for U.S. Appl. No. 14/857,407.
Office Action dated May 3, 2017 for U.S. Appl. No. 14/855,303.
Office Action dated May 4, 2017 for U.S. Appl. No. 14/848,775.
Office Action dated May 4, 2017 for U.S. Appl. No. 14/857,224.
Office Action dated Jun. 2, 2017 for U.S. Appl. No. 14/789,920.
Office Action dated Jun. 2, 2017 for U.S. Appl. No. 14/965,725.
Office Action dated Jun. 21, 2017 for U.S. Appl. No. 14/965,665.
Office Action dated Jun. 22, 2017 for U.S. Appl. No. 14/848,032.
Office Action dated Jun. 29, 2017 for U.S. Appl. No. 15/161,547.
Office Action dated Jun. 30, 2017 for U.S. Appl. No. 15/161,533.
Office Action dated Aug. 1, 2017 for U.S. Appl. No. 14/839,749.
Office Action dated Aug. 16, 2017 for U.S. Appl. No. 14/183,503.
Office Action dated Aug. 16, 2017 for U.S. Appl. No. 14/928,087.
Office Action dated Aug. 21, 2017 for U.S. Appl. No. 15/005,897.
Office Action dated Aug. 23, 2017 for U.S. Appl. No. 14/872,718.
Office Action dated Sep. 25, 2017 for U.S. Appl. No. 14/793,625.

"Products," Cepheid, Inc., Sunnyvale, California, United States, https://web.archive.Org/web/20040407201033/http://cepheid.com:80/pages/products.htm 1, archived Apr. 7, 2004.

"Cepheid—Products," Cepheid, Inc., Sunnyvale, California, United States, https://web.archive.Org/web/2004/0614174818/https://www.cepheid.com:80/Sites/cephe id/content.cfm?id=158, archived Jun. 14, 2004.

Belgrader, P., et al., "A microfluidic cartridge to prepare spores for PCR analysis," Biosensors & Bioelectronics, vol. 14: 849-852 (2000).

Ulrich, M. P., et al., "Evaluation of the Cepheid GeneXpert® system for detecting Bacillus anthracis," Journal of Applied Microbiology, vol. 100: 1011-1016 (2006).

Mcmillan, W. A., "Real-time point-of-care molecular detection of infectious disease agents," American Clinical Laboratory, vol. 21(1): 29-31 (2002).

Meehan, P. J., et al., "Responding to Detection of Aerosolized Bacillus anthracis by Autonomous Detection Systems in the Workplace," Morbidity and Mortality Weekly Report: Recommendations and Reports, vol. 53 (7): 1-12 (2004).

Petersen, K., et al., "IVD systems in bioterrorism response," IVDT: Beyond Clinical Diagnostics, vol. 8(4): 3 5-40 (2002).

"Cepheid Granted US Patent Covering Key Internal Control Method for Ensuring Accurate DNA Test Results," Cepheid Inc., Sunnyvale, California, United States, Nov. 27, 2001.

Piccolo® Operator's Manual, Abaxis, Inc., Union City, California, United States, Mar. 2001.

Von Schenck, H., et al., "Evaluation of "HemoCue," a New Device for Determining Hemoglobin," Clin Chem., vol. 32(3): 526-529 (1986).

Neufeld, L., et al., "Hemoglobin measured by Hemocue and a reference method in venous and capillary blood: A validation study," Salud Publica de Mexico, vol. 44(3): 219-227 (2002).

HemoCue Hb 201+ Operating Manual, HomeCue AB, Angelholm Sweden, www.hemocue.com.

Cheng, S. B., et al., "Development of a Multichannel Microfluidic Analysis System Employing Affinity Capillary Electrophoresis for Immunoassay," Anal. Chem., vol. 73(7): 1472-1479 (2001).

Clayton, J., "Go with the microflow," Nature Methods, vol. 2(8): 621-627 (2005).

Hong, J. W., et al., "A nanoliter-scale nucleic acid processor with parallel architecture," Nature Biotechnology, vol. 22(4): 435-439 (2004).

\* cited by examiner

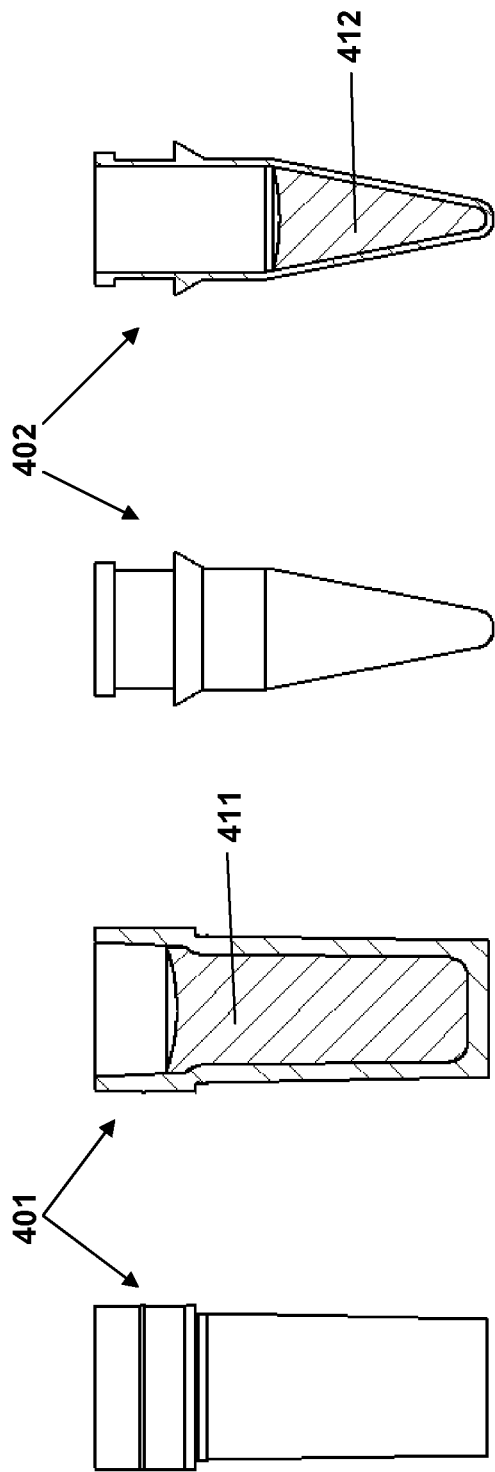

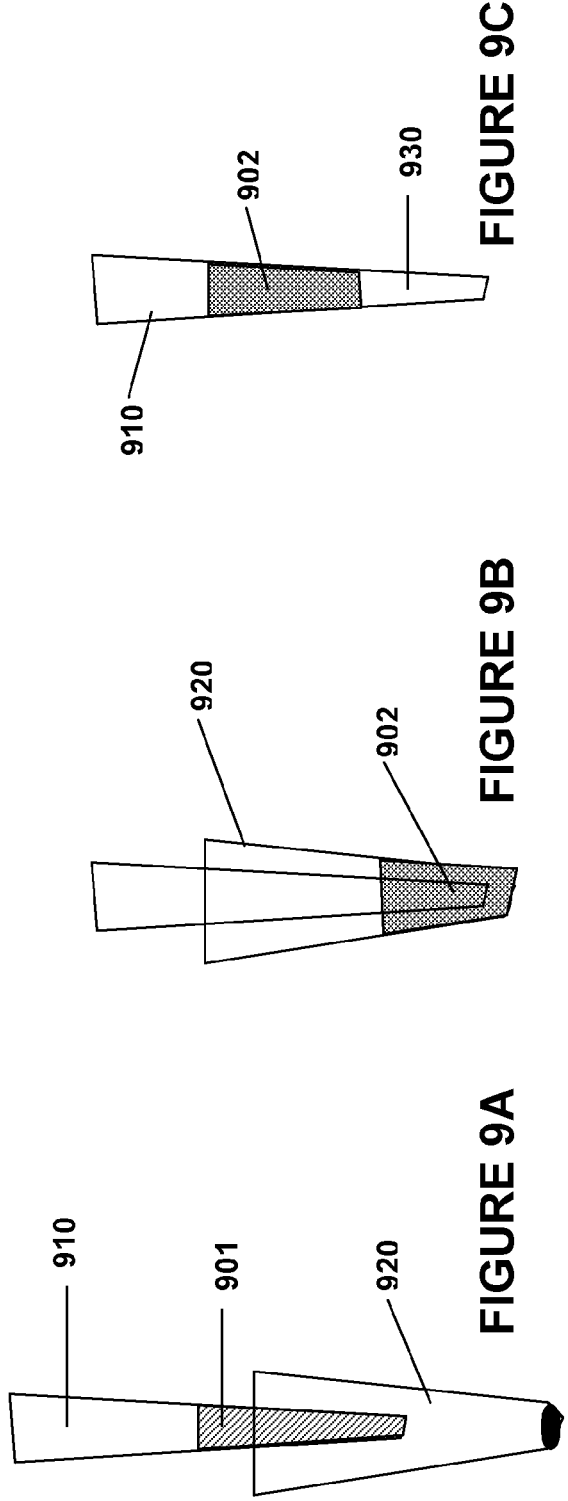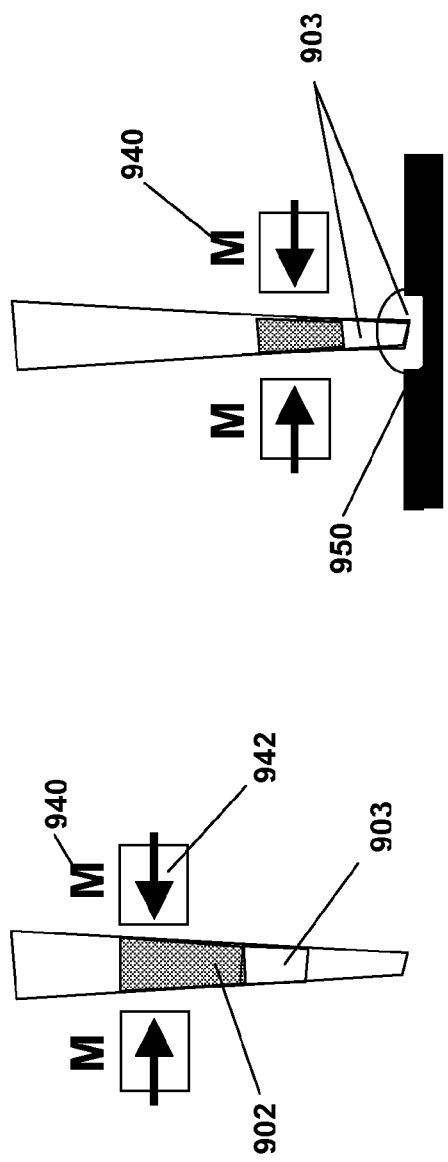

MODULAR POINT-OF-CARE DEVICES, SYSTEMS, AND USES THEREOF

CROSS-REFERENCE

This application is a continuation application of, and claims priority under 35 U.S.C. §120 to, U.S. patent application Ser. No. 15/007,585, filed Jan. 27, 2016, which is a continuation of U.S. patent application Ser. No. 14/670,200, filed Mar. 26, 2015, now U.S. Pat. No. 9,285,366, which is a continuation of U.S. patent application Ser. No. 13/893,258 filed May 13, 2013, now U.S. Pat. No. 9,121,851, which is a continuation of U.S. patent application Ser. No. 13/889,674 filed May 8, 2013, now U.S. Pat. No. 8,822,167, which is a continuation of U.S. patent application Ser. No. 13/326,023 filed Dec. 14, 2011, which is a continuation of U.S. patent application Ser. No. 12/244,723, filed Oct. 2, 2008, now U.S. Pat. No. 8,088,593, which is a non-provisional application claiming priority under 35 U.S.C. §119(e) to, and which claims the benefit of, U.S. Provisional Application No. 60/997,460, filed Oct. 2, 2007, the contents of all of which non-provisional and provisional applications are hereby incorporated herein by reference in their entireties.

BACKGROUND OF THE INVENTION

The discovery of a vast number of disease biomarkers and the establishment of miniaturized medical systems have opened up new avenues for the prediction, diagnosis and monitoring of treatment of diseases in a point-of-care setting. Point-of-care systems can rapidly deliver test results to medical personnel, other medical professionals and patients. Early diagnosis of a disease or disease progression can allow medical personnel to begin or modify therapy in a timely manner.

Multiplexed biomarker measurement can provide additional knowledge of the condition of a patient. For example, when monitoring the effects of a drug, three or more biomarkers can be measured in parallel. Typically, microtiter plates and other similar apparatuses have been used to perform multiplexed separation-based assays. A microtiter plate (for example, a 384 well microtiter plate) can perform a large number of assays in parallel.

In a Point-of-Care (POC) device, the number of assays that can be performed in parallel is often limited by the size of the device and the volume of the sample to be analyzed. In many POC devices, the number assays performed is about 2 to 10. A POC device capable of performing multiplexed assays on a small sample would be desirable.

A shortcoming of many multiplexed POC assay devices is the high cost of manufacturing the components of the device. If the device is disposable, the high cost of the components can make the manufacturing of a POC device impractical. Further, for multiplexed POC devices that incorporate all of the necessary reagents onboard of the device, if any one of those reagents exhibit instability, an entire manufactured lot of devices may have to be discarded even if all the other reagents are still usable.

When a customer is interested in a customizing a POC device to a particular set of analytes, manufacturers of multiplexed POC assay systems are often confronted with a need to mix-and-match the assays and reagents of the device. A multiplexed POC assay suitable to each customer can be very expensive, difficult to calibrate, and difficult to maintain quality control.

POC methods have proven to be very valuable in monitoring disease and therapy (for example, blood glucose systems in diabetes therapy, Prothrombin Time measurement in anticoagulant therapy using Warfarin). By measuring multiple markers, it is believed that complex diseases (such as cancer) and therapies such as multi-drug therapy for cancer can be better monitored and controlled.

SUMMARY OF THE INVENTION

Thus, there remains an unmet need for alternative designs of POC devices. A desirable design provides modular capture surfaces and assay incubation elements. Furthermore, modular capture surfaces and assay incubation elements need to be integrated into POC disposables suited for just-in-time (JIT) manufacturing methods. It would be desirable to provide a customizable POC device at a practical cost to user and the manufacturer. The present invention addresses these needs and provides related advantages as well.

In an aspect, a cartridge is disclosed for automated detection of an analyte in a bodily fluid sample comprising: an array of addressable assay units configured to run a chemical reaction that yields a detectable signal indicative of the presence or absence of the analyte; and an array of addressable reagent units, wherein an individual addressable reagent unit of the array is addressed to correspond to an individual addressable assay unit of the array of assay units, and wherein the individual reagent units are configured to be calibrated in reference to the corresponding individual assay unit before the arrays are assembled on the cartridge. The device can further comprise a sample collection unit configured to receive the bodily fluid sample.

In another aspect, a cartridge is disclosed for automated detection of an analyte in a bodily fluid sample comprising: a sample collection unit configured to receive the bodily fluid sample; an array of assay units configured to receive a portion of the sample from the sample collection unit and run a chemical reaction that yields a detectable signal indicative of the presence of the analyte in the sample; and an array of reagent units containing reagents for running the chemical reaction; wherein an individual assay unit of the array of assay units and an individual reagent unit of the array of reagents units are configured to be movable into fluid communication such that reagents for running the chemical reaction are brought to contact with the bodily fluid sample in the assay unit.

An individual reagent unit can be configured to receive a movable assay unit. In some embodiments, the individual assay unit comprises an assay tip. In some embodiments, the individual assay unit is configured to run an immunoassay. The bodily fluid sample can be a blood sample. In some instances, a sample collection unit is configured to receive a volume of the bodily fluid sample about 50, 20, 10, 5 or 3 microliters or less. In an instance, the sample collection unit is configured to receive a volume of the bodily fluid sample equivalent to a single drop of blood.

A device as described herein can comprise a pretreatment unit configured to retrieve a portion of the bodily fluid sample for running the chemical reaction to detect the analyte and the pretreatment unit can be configured to retrieve plasma from whole blood sample received in the sample collection unit.

In an aspect, a system is described herein for automated detection of an analyte in a bodily fluid sample comprising: a device as described herein; and a detection assembly for detecting the detectable signal indicative of the presence or absence of the analyte. The system can further comprise a programmable mechanical device configured to move the individual assay unit from a first location to a second location. In some instances, a system comprises a fluid transfer device. The fluid transfer device can be a pipette and can be automated. A system can also comprise a communication assembly for transmitting a protocol based on the analyte to be detected. In some instances, a system herein comprises a heating block configured to receive an individual assay unit and can also comprise a magnetic block, for example, that can be used for separation of red cells from the sample.

In another aspect, a system is disclosed for automated detection of a plurality of analytes in a bodily fluid sample, comprising: a fluidic device comprising: a sample collection unit configured to contain the bodily fluid sample; an array of assay units, wherein an individual assay unit of said array of assay units is configured to run a chemical reaction that yields a signal indicative of an individual analyte of said plurality of analytes being detected; and an array of reagent units, wherein an individual reagent unit of said array of reagent units contains a reagent; and a fluid transfer device comprising a plurality of heads, wherein an individual head of the plurality of heads is configured to engage the individual assay unit, and wherein said fluid transfer device comprises a programmable processor configured to direct fluid transfer of the bodily fluid sample from the sample collection unit and the reagent from the individual reagent unit into the individual assay unit. In some embodiments, the configuration of the processor to direct fluid transfer effects a degree of dilution of the bodily fluid sample in the array of assay units to bring signals indicative of the plurality of analytes being detected within a detectable range, such that said plurality of analytes are detectable with said system.

In some instances, a bodily fluid sample comprises at least two analytes that are present at concentrations that differ by at least 2, 5, 10, 15, 50, or 100 orders of magnitude. The degree of dilution of the bodily fluid sample can bring the signals indicative of the at least two analytes within the detectable range.

A system herein can further comprise a detector configured to detect signal intensities of the detectable range. An exemplary detector is a photomultiplier and a detectable range of the detector can be about 20 to about 10 million counts.

In some embodiments, wherein the individual head of a fluid transfer device is configured to adhere to the individual assay unit. The individual assay unit can provide an immunoassay reaction site. In some instances, the individual assay unit is a pipette tip. The fluid transfer device can be a pipette such as an air-displacement pipette. The fluid transfer device can also comprises a motor in communication with the programmable processor, wherein the motor can move said plurality of heads based on a protocol from said programmable processor.

In another aspect, a system is described herein for automated detection of a plurality of analytes in a plasma portion of a whole blood sample, comprising: a device configured to automatically receive and process the whole blood sample to yield the plasma portion, from which a detectable signal indicative of the presence or absence of the analyte of interest is generated onboard the device; and a detection assembly for detecting the detectable signal indicative of the presence or absence of the analyte.

In an aspect, provided herein is a method of detecting an analyte in a bodily fluid sample comprising: providing a blood sample to a device as described herein; allowing said sample to react within at least one assay unit; and detecting said detectable signal generated from said analyte collected in said sample of bodily fluid. The bodily fluid sample can be blood and the method can comprise retrieving plasma from the blood.

In an aspect as provided herein, a method of on-demand assembly of a cartridge for automated detection of an analyte in a bodily fluid sample, wherein the device comprises a housing, said housing comprising: an array of addressable assay units, wherein an individual assay unit of the array is configured to run a chemical reaction that yields a detectable signal indicative of the presence or absence of the analyte; and an array of addressable reagent units, wherein an individual reagent unit of the array is addressed to correspond to the individual assay unit, said method comprises: (i) placing according to the analyte to be detected an array of addressable assay units, wherein an individual assay unit of the array is configured to run a chemical reaction that detects an analyte of interest ordered by said end user, into the housing; (ii) placing according to the analyte to be detected an array of reagent units, wherein an individual reagent unit of the array corresponds to the individual assay unit, into the housing; and (iii) securing the arrays of (i) and (ii) within the housing of the device. The method can comprise selecting an analyte to be detected. In some embodiments, the method comprises sealing the cartridge. In an embodiment, the method comprises labeling the cartridge with a readable label indicating the analyte to be detected, for example with a bar code or RFID.

In an aspect, a method is provided for automated detection of a plurality of analytes in a bodily fluid sample, comprising: providing the bodily fluid sample to a fluidic device, wherein the fluidic device comprises: a sample collection unit configured to contain the bodily fluid sample; an array of assay units, wherein an individual assay unit of said array of assay units is configured to run a chemical reaction that yields a signal indicative of an individual analyte of said plurality of analytes being detected; and an array of reagent units, wherein an individual reagent unit of said array of reagent units contains a reagent; engaging the individual assay unit using a fluid transfer device; transferring the bodily fluid sample from the sample collection unit to the individual assay unit using the fluid transfer device; and transferring the reagent from the individual reagent unit to the individual assay unit, thereby reacting the reagent with the bodily fluid sample to yield the signal indicative of the individual analyte of the plurality of analytes being detected.

In an embodiment, the fluid transfer device comprises a plurality of heads, wherein an individual head of the plurality of heads is configured to engage the individual assay unit; and wherein said fluid transfer device comprises a programmable processor configured to direct fluid transfer of the bodily fluid sample from the sample collection unit and the reagent from the individual reagent unit into the individual assay unit. The method can further comprise providing instructions to the programmable processor, wherein the instructions can direct the step of transferring the bodily fluid sample to the individual assay unit.

In an embodiment, the step of transferring the bodily fluid sample effects a degree of dilution of the bodily fluid sample in the individual assay unit to bring the signal indicative the individual analyte of the plurality of analytes being detected within a detectable range. The bodily fluid sample can comprise at least two individual analytes that are present at concentrations that differ by at least 2, 5, 10, 15, 50, or 100 orders of magnitude. In some instances, the degree of dilution of the bodily fluid sample brings the signals indicative of the at least two individual analytes within the detectable range. In an embodiment, the detectable range is about 1000 to about 1 million counts per second using a photomultiplier.

In an embodiment, the reagent in the individual reagent unit is an enzyme substrate for an immunoassay and the method can further comprise repeating the step of transferring the reagent from the individual reagent unit after the reaction to yield the signal indicative of the individual analyte of the plurality of analytes being detected is complete, thereby creating a second reaction to yield a second signal indicative of the individual analyte. An intensity of the signal and a second intensity of the second signal indicative of the individual analyte can be averaged to calculate the final intensity of the signal indicative of the individual analyte.

In an aspect, a method is described herein of measuring a volume of a liquid sample, comprising: reacting a known quantity of a control analyte in a liquid sample with a reagent to yield a detectable signal indicative of the control analyte; and comparing said detectable signal with an expected detectable signal, wherein the expected signal is indicative of an expected volume of the liquid sample, and wherein said comparison provides a measurement of said volume of said liquid sample being measured. In some instances, the control analyte is not normally present in said liquid sample in a detectable amount. The method can comprise verifying the volume of said liquid sample when the measurement of the volume of the sample is within about 50% of the expect volume of the liquid sample. In an embodiment, the method further comprises: reacting a bodily fluid sample containing a target analyte with a reagent to yield a detectable signal indicative of the target analyte; and measuring the quantity of the target analyte in the bodily fluid sample using an intensity of said detectable signal indicative of the target analyte and the measurement of said volume of said liquid sample. The liquid sample and the bodily fluid sample can be the same sample and the control analyte does not react with the target analyte in the bodily fluid sample. In some instances, the liquid sample and the bodily fluid sample are different liquid samples. The control analyte can be, for example, fluorescein-labeled albumin, fluorescein labeled IgG, anti-fluorescein, anti-digoxigenin, digoxigenin-labeled albumin, digoxigenin-labeled IgG, biotinylated proteins, non-human IgG.

In another aspect, a method of retrieving plasma from a blood sample is provided herein that comprises: mixing a blood sample in the presence of magnetizable particles in a sample collection unit, wherein the magnetizable particles comprise an antibody capture surface for binding to non-plasma portions of the blood sample; and applying a magnetic field above a plasma collection area to the mixed blood sample to effect suspension of the non-plasma portions of the blood sample on top of the plasma collection area. In some instances, the sample collection unit is a capillary tube. The blood sample can be less than about 20 microliters and the plasma retrieved can be less than about 10 microliters. In some instances, the blood sample is not diluted. In some instance, mixing occurs in the presence of antibodies unbound to a solid surface. The mixing can comprise mixing by syringe action.

In yet another aspect, a method is provided herein of using automated immunoassay for detecting an analyte present in plasma portion of a whole blood sample, comprising: providing a whole blood sample to a device that is configured to automatically receive and process on board the whole blood sample to yield the plasma portion, from which a detectable signal indicative of the presence or absence of the analyte of interest is generated on board; detecting said signal that is indicative of the presence or absence of the analyte in said bodily fluid sample; and transmitting result of (b) to an end user. The immunoassay can be an ELISA. In some instances, the result is transmitted wirelessly.

In some embodiments, a method as described herein is carried out in a system as described herein.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

Many novel features of the invention are set forth with particularity in the appended claims. A better understanding of the features and advantages of the invention will be obtained by reference to the following detailed description that sets forth illustrative embodiments, in which many principles of the invention are utilized, and the accompanying drawings of which:

FIGS. 4A and 4B illustrate two examples of a reagent unit comprising a cup.

FIGS. 9A through 9E demonstrate an example of a plasma separation method wherein a whole blood sample has been aspirated into a sample tip and a magnetic reagent is mixed and suspended with the sample, then a magnetic field is applied to the whole blood sample and magnetic reagent mixture. Separated blood plasma sample can then be distributed into a well of a device.

DETAILED DESCRIPTION OF THE INVENTION

Figure 1:
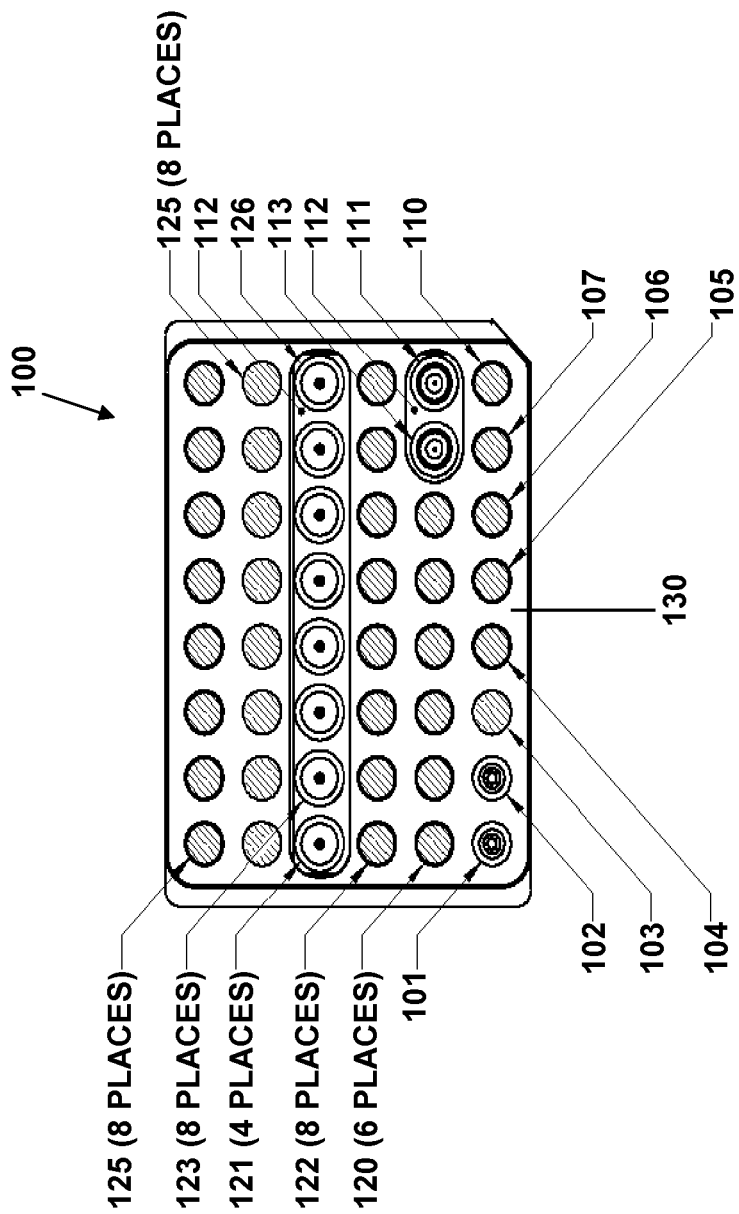
FIG. 1 illustrates an exemplary device of the invention comprising assay units, reagents unit, and other modular components of the device.

The embodiments and aspects of the invention described herein pertain to devices, systems, and methods for automated detection of an analyte in a sample of bodily fluid. The invention is capable of detecting and/or quantifying analytes that are associated with specific biological processes, physiological conditions, disorders or stages of disorders, or effects of biological or therapeutic agents. The embodiments and examples of the invention described herein are not intended to limit the scope of invention.

Devices

In an aspect of the invention, a device for automated detection of an analyte in a bodily fluid sample comprises an array of addressable assay units configured to run a chemical reaction that yields a detectable signal indicative of the presence or absence of the analyte, and an array of addressable reagent units, each of which is addressed to correspond to one or more addressable assay units in said device, such that individual reagent units can be calibrated in reference to the corresponding assay unit(s) before the arrays are assembled on the device.

In another aspect of the invention, a device for automated detection of an analyte in a bodily fluid sample comprises an array of assay units configured to run a chemical reaction that yields a detectable signal indicative of the presence of the analyte, and an array of reagent units containing reagents for running the chemical reaction, wherein at least one of the assay units and at least one of the reagent units are movable relative to each other within the device such that reagents for running the chemical reaction are automatically brought to contact with the bodily fluid sample in the assay unit.

In an embodiment of a device of the invention, the array of assay units or reagent units can be addressed according to the chemical reaction to be run by the configured assay unit. In another embodiment, at least one of the assay units and at least one of the reagent units are movable relative to each other within the device such that reagents for running the chemical reaction are automatically brought to contact with the bodily fluid sample in the assay unit.

In one embodiment, the device of the invention is self-contained and comprises all reagents, liquid- and solid-phase reagents, required to perform a plurality of assays in parallel. Where desired, the device is configured to perform at least 2, 3, 4, 5, 6, 7, 8, 9, 10, 20, 30, 40, 50, 100, 200, 500, 1000 or more assays. One or more control assays can also be incorporated into the device to be performed in parallel if desired.

The assays can be quantitative immunoassays and can be conducted in a short period of time. Other assay type can be performed with a device of the invention including, but not limited to, measurements of nucleic acid sequences and measurements of metabolytes, such as cholesterol. In some embodiments, the assay is completed in no more than one hour, preferably less than 30, 15, 10, or 5 minutes. In other embodiments, the assay is performed in less than 5 minutes. The duration of assay detection can be adjusted accordingly to the type of assay that is to be carried out with a device of the invention. For example, if needed for higher sensitivity, an assay can be incubated for more than one hour or up to more than one day. In some examples, assays that require a long duration may be more practical in other POC applications, such as home use, than in a clinical POC setting.

Any bodily fluids suspected to contain an analyte of interest can be used in conjunction with the system or devices of the invention. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

A bodily fluid may be drawn from a patient and provided to a device in a variety of ways, including but not limited to, lancing, injection, or pipetting. As used herein, the terms subject and patient are used interchangeably herein, and refer to a vertebrate, preferably a mammal, more preferably a human Mammals include, but are not limited to, murines, simians, humans, farm animals, sport animals, and pets. In one embodiment, a lancet punctures the skin and withdraws a sample using, for example, gravity, capillary action, aspiration, or vacuum force. The lancet may be part of the device, or part of a system, or a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the device, as for example, could occur with a saliva sample. The collected fluid can be placed in the sample collection unit within the device. In yet another embodiment, the device comprises at least one microneedle which punctures the skin. 3

The volume of bodily fluid to be used with a device is generally less than about 500 microliters, typically between about 1 to 100 microliters. Where desired, a sample of 1 to 50 microliters, 1 to 40 microliters, 1 to 30 microliters, 1 to 10 microliters or even 1 to 3 microliters can be used for detecting an analyte using the device.

In an embodiment, the volume of bodily fluid used for detecting an analyte utilizing the subject devices or systems is one drop of fluid. For example, one drop of blood from a pricked finger can provide the sample of bodily fluid to be analyzed with a device, system or method described herein.

A sample of bodily fluid can be collected from a subject and delivered to a device of the invention as described hereinafter.

In an embodiment, the arrays of assay and reagent units are configured to be a set of mix-and-match components. The assay units can comprise at least one capture surface capable of reacting with an analyte from the sample of bodily fluid. The assay unit may be a tubular tip with a capture surface within the tip. Examples of tips of the invention are described herein. A reagent unit typically stores liquid or solid reagents necessary for conducting an assay that detect a give analyte. Each individual assay and reagent unit can be configured for assay function independently. To assemble a device, the units can be assembled in a just-in-time fashion for use in integrated cartridges.

Separate components, both liquid and solid phase, can be made and then be tested for performance and stored. In an embodiment, the assembly of the device is carried out in on-demand fashion at a manufacturing location. The device can be modular and include components such as a housing that is generic for all assays, assay units, such as tips, and reagent units, such as a variety of frangible or instrument operable containers that encapsulate liquid reagents. In some instances, an assembled device is then tested to verify calibration (the relation of the system response to known analyte levels). Assay devices can be assembled from a library of pre-manufactured and calibrated elements on demand. In some embodiments, fluidic pathways within a device can be simple and obviate any chance of trapping bubbles and providing an efficient way to wash away excess labeled reagents in reagent excess assays such as ELISAs.

A housing for a device of the invention can be made of polystyrene or another moldable or machinable plastic and can have defined locations to place assay units and reagent units. In an embodiment, the housing has means for blotting tips or assay units to remove excess liquid. The means for blotting can be a porous membrane, such as cellulose acetate, or a piece bibulous material such as filter paper.

In some embodiments, at least one of the components of the device may be constructed of polymeric materials. Non-limiting examples of polymeric materials include polystyrene, polycarbonate, polypropylene, polydimethysiloxanes (PDMS), polyurethane, polyvinylchloride (PVC), polysulfone, polymethylmethacrylate (PMMA), acrylonitrile-butadiene-styrene (ABS), and glass.

The device or the subcomponents of the device may be manufactured by variety of methods including, without limitation, stamping, injection molding, embossing, casting, blow molding, machining, welding, ultrasonic welding, and thermal bonding. In an embodiment, a device in manufactured by injection molding, thermal bonding, and ultrasonic welding. The subcomponents of the device can be affixed to each other by thermal bonding, ultrasonic welding, friction fitting (press fitting), adhesives or, in the case of certain substrates, for example, glass, or semi-rigid and non-rigid polymeric substrates, a natural adhesion between the two components.

An exemplary device as described herein is illustrated in FIG. 1. The is also sometimes referred to herein as a cartridge 100. The device 100 comprises a housing 130 with locations to accommodate assay units 121 and reagent units 103, 122, 124, 125. In the exemplary embodiment of FIG. 1, assay units 121 occupy a center row of the housing 130 of the device 100. The assay units 121 can optionally include at least one calibration unit 126. In an example, the assay units 121 are similar to pipette tips and are referred to as assay tips 121 and the calibration units 126 are referred to as calibration tips 126 herein, however, the assay units 121 can be of any shape and size as are accommodated broadly by a device 100 as described herein. The assay units 121 and calibration units 126 are exemplary assay units 121 and are described in more detail herein. The assay units 121 in FIG. 1 can comprise a capture surface and are capable, for example, of performing a chemical reaction such as nucleic acid assays and immunoassays. The assay units 121 can be assembled into the housing according to instructions or the assays that a user wishes to perform on a sample.

As shown in FIG. 1, the housing of the device 100 can comprise a sample collection unit 110 configured to contain a sample. A sample, such as a blood sample, can be placed into the sample collection unit 110. A sample tip 111 (for example, a pipette tip that couples to a fluid transfer device as described in more detail herein) can occupy another portion of the housing 130. When an assay is to be run the sample tip 111 can distribute the sample to pretreatment reagent units or pretreatment units 103, 104, 105, 106, 107, or assay units 121. Exemplary pretreatment units 103, 104, 105, 106, 107 include but are not limited to: mixing units 107, diluent or dilution units 103, 104, and, if the sample is a blood sample, plasma removal or retrieval units 105, 106. The pretreatment units 103, 104, 105, 106, 107 can be the same type of unit or different types of units. Other pretreatment units 103, 104, 105, 106, 107 as are necessary to run a chemical reaction can be incorporated into device 100 as would be obvious to one skilled in the art with knowledge of this disclosure. The units 103, 104, 105, 106, 107 can contain various amounts of reagents or diluents, flexible to whatever is needed to run the assay on the current cartridge 100.

Often, the assay units 121 can be manufactured separately from the housing 130 and then inserted into the housing 130 with pick-and-place methods. The assay units 121 can fit snugly into the housing 130 or can fit loosely into the housing 130. In some embodiments, the housing 130 is manufactured such that is holds the reagent units 103, 122, 124, 125 and/or assay units 121 snugly in place, for example during shipping or manipulation a cartridge. Reagents units 103, 122, 124, 125 are shown in FIG. 1 that contain a conjugate reagent 122 (for example, for use with an immunoassay), a wash reagent 125 (for example, to wash said conjugate from capture surfaces), and a substrate 124 (for example, an enzyme substrate). Other embodiments of the device 100 and the components in the example in FIG. 1 are described herein. Reagent units 103, 122, 124, 125 can be manufactured and filled separately from the housing 130 and then placed into the housing 130. In this way, a cartridge 100 can be built in a modular manner, therefore increasing the flexibility of the cartridge 100 to be used for a variety of assays. Reagents in a reagent unit 103, 122, 124, 125 can be chosen according to the assay to be run. Exemplary reagents and assays are described herein.

A device, such as the example shown in FIG. 1, can also comprise other features as may be needed to run a chemical reaction. For example, if the assay units 121 are assay tips 121 as described herein, the device can comprise tip touch-off pads 112 to remove excess sample or reagent from an assay tip 121 or a sample tip 111 after fluid transfer, for example, by a system as described herein. The housing 130 can also comprise units or areas 101, 102 within the device 100 for placing a used tip or unit, for example, in order to avoid cross-contamination of a sample tip 111 or assay unit 121. In FIG. 1, the device 100 comprises a sample tip 111 for transferring a sample between units of the device 100. The device 100 as illustrated in FIG. 1 also comprises a pretreatment tip 113 for transferring a sample that has been pretreated in a unit of the device 100 to other units of a device 100 to perform a chemical reaction. For example, the sample tip 111 can be used to remove a blood sample from the sample collection unit 110 and transfer the blood sample to pretreatment units 103, 104, 105, 106, 107 as described. Red cells can be removed from the blood sample in the pretreatment units 103, 104, 105, 106, 107 and the pretreatment tip 113 can then be used to collect the blood plasma from the pretreatment units 103, 104, 105, 106, 107 and transfer the blood plasma to another pretreatment unit (for example, a diluent unit) 103, 104, 105, 106, 107 and/or to at least one assay unit 121. In an embodiment, a sample tip 111 is the sample collection unit 110. In another embodiment, the sample collection unit 110 is similar to a well and is configured to contain a sample as received by a user.

Assay units 121 and reagent units 103, 122, 124, 125 as shown in FIG. 1 can be addressable to indicate the location of the units on the cartridge 100. For example, a column of the cartridge 100 as shown in FIG. 1 can contain an assay unit 121 to run an assay configured to detect C-reactive protein, and the column can contain corresponding reagent units 103, 122, 124, 125 for that assay in the same column, wherein the units are addressed to correspond to each other. For example, the addresses can be entered and stored in a computer system, and the cartridge 100 can be given a label, such as a bar code. When the bar code of the cartridge 100 is scanned for use, the computer system can send the addresses of the units to a system, such as those described herein, to transfer the fluids and run a reaction according to the addresses entered into the computer. The addresses can be part of a protocol sent to operate the system. The addresses can be in any configuration and can be altered if need be to change the protocol of running an assay, which in turn can offer a change in assay protocol or steps to a user of the cartridge that has not been typically available in prior art POC devices. In some embodiments, the housing 130 and units are configured in a 6 by 8 array of units as shown in FIG. 1. The layout of the units can be of any format, for example, rectangular arrays or random layouts. A cartridge 100 can comprise any number of units, for example between 1 and about 500. In some embodiments, a cartridge 100 has between 5-100 units. As an example as shown in FIG. 1, the cartridge 100 has 48 units.

Figure 2:
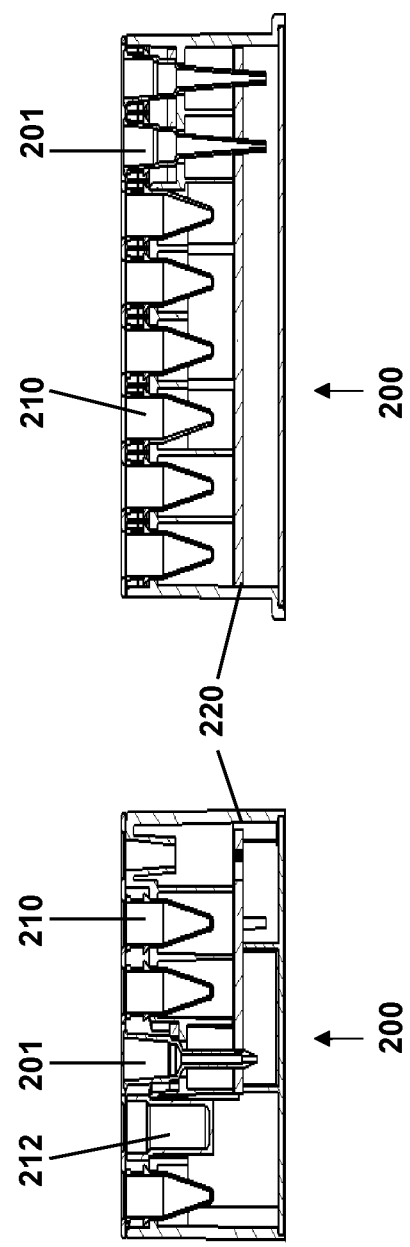
FIG. 2 illustrates two side-cut away views of the exemplary device of FIG. 1 comprising cavities in the housing of the device shaped to accommodate an assay unit, a reagent unit, and a sample tip.

Two side cut-away views of the exemplary device 200 of FIG. 1 are illustrated in FIGS. 2A and 2B. A cavity can be shaped in a housing 220 of a device to accommodate assay units (for example, assay tips) 201 in a vertical orientation (housing horizontal) with their bosses toward the top of the device 200. As shown in FIG. 2, a cavity can also be shaped to accommodate a reagent unit 210, 212 or a sample collection unit or tip 202. There may be features in the housing 220 to capture the units precisely and hold them securely. Such features can also be designed to operate with a mechanism for moving the tips, such as tip pick-up and drop-off. In another embodiment, the sample collection unit comprises a bendable or breakable element that serves to protect a small collection tube during shipment and to hold a plunger device in place within a capillary. Also shown in FIG. 2A are two exemplary embodiments of reagent units 210, 212 as are described herein. The bottom of the housing 220 can be configured to collect waste liquids, for example, wash reagents after use that are transferred back through a hole in the housing 220 to the bottom. The housing 220 can comprise an absorbent pad to collect waste fluids. The assay units 201 and sample units 202 can be positioned to fit through a cavity of the housing 220 of the device 200 and extend beyond an inner support structure. The reagent units 210, 212 fit snugly into the housing as is shown in FIG. 2 and do not extend beyond the inner support structure. The housing 220 and the areas in which the assay units 201 and reagents units 210, 212 can be held and positioned may adapt a variety of patterns.

In some embodiments, each tip provides for a single assay and can be paired with or corresponded to an appropriate reagent, such as required reagents for running the designated assay. Some tips provide for control assay units and have known amounts of analyte bound to their capture surfaces either in the manufacturing process or during the performance of an assay. In case of a control assay unit, the unit is configured to run a control assay for comparison. The control assay unit may comprise, for example, a capture surface and analyte that are in a solid or liquid state.

In many embodiments, the device holds all reagents and liquids required by the assay. For example, for a luminogenic ELISA assay the reagents within the device may include a sample diluent, a detector conjugate (for example, three enzyme-labeled antibodies), a wash solution, and an enzyme substrate. Additional reagents can be provided as needed.

In some embodiments, reagents can be incorporated into a device to provide for sample pretreatment. Examples of pretreatment reagents include, without limitation, white cell lysis reagents, reagents for liberating analytes from binding factors in the sample, enzymes, and detergents. The pretreatment reagents can also be added to a diluent contained within the device.

An individual reagent unit can be configured to receive a movable assay unit. In some embodiments, the individual assay unit comprises an open ended hollow cylindrical element comprising a capture surface and a reaction cuvette. A cylindrical assay unit can be referred to as an assay tip herein. In some embodiments, the individual assay unit is configured to run an immunoassay. An assay unit 301 that comprises a small tip or tubular formation is shown in FIG. 3A. In some instances, the tip 301 is configured to provide an interior cylindrical capture surface 311 and a boss 321 capable of engaging with the housing of device. In some instances, the boss 321 and the tip 301 is configured to engage with a mechanism of moving the tip 301 such as a system as described herein or for example, a fluid transfer device. An assay tip 301 as shown in FIG. 3A can comprise an opening 331 at the bottom of the tip. The opening 331 can be utilized for transferring fluids or reagents in and out of an assay unit 301. In an embodiment, an assay unit 301 as described is or is similar to a pipette tip with the improvement that the assay unit 301 comprises a capture surface 311 configured to detect an analyte in a sample.

The tip 301 can be manufactured by an injection-molded process. In an embodiment, the tip 301 is made of a clear polystyrene for use with chemiluminescence assays. As shown in FIG. 3A, an exemplary tip 301 comprises a boss (shown as the larger top half of the tip 301), which can engage with a housing and can engage, for example, with tapered elements of a fluid transfer device and/or pipetting devices so as to form a pressure-tight seal. Also shown in FIG. 3A, the exemplary tip 301 comprises a smaller cylindrical part. In many embodiments, an assay capture surface is contained within the smaller cylindrical part. The assay capture surface can be anywhere within the tip 301 or on the outside of the tip 301. The surface of the tip 301 can be of many geometries including, but not limited to, tubular, cubic, or pyramidal. In chemiluminescence and fluorescence-based assays, the tip 301 can serve as a convenient means to present the assay product to the assay optics.

Figure 3B:
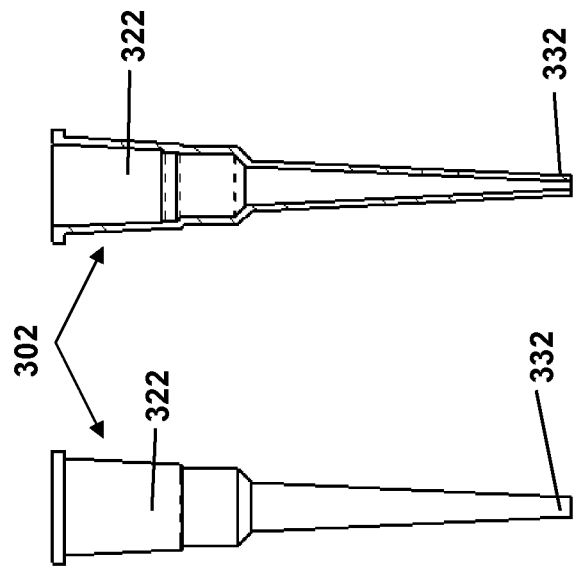
FIG. 3B demonstrates an example of a sample tip as described herein.
Figure 3A:
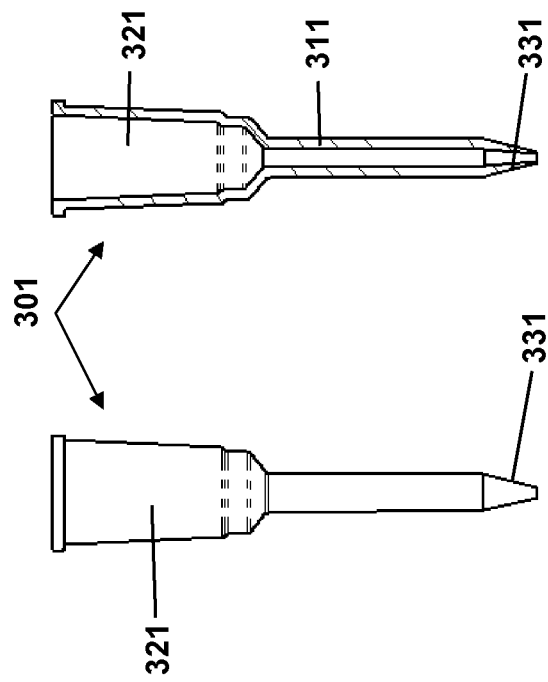
FIG. 3A demonstrates an exemplary assay unit that comprises a small tip or tubular formation.

FIG. 3B demonstrates an exemplary sample collection unit 302 comprising a sample tip 302. The sample tip 302 as shown in FIG. 3B can also be separate from a sample collection unit 302 and used to transfer sample from the sample collection units to other units on a device as described herein. The sample tip as shown in FIG. 3B comprises a boss 322 as described herein to couple the tip 302 with a housing of a device and a fluid transfer device. The sample tip 302 also comprises an opening 332 to allow the transfer of fluids or samples in and out of the sample tip. In some embodiments, the sample tip 302 is of the same shape as an assay tip 301. In other embodiments (such as those shown in FIGS. 3A and 3B), the sample tip 302 is a different shape than the assay tip 301.

In an embodiment, one function of a tip is to enable samples and liquid reagents to be brought into contact with the capture surface of the assay unit. The movement can occur by a variety of means including, but not limited to, capillary action, aspiration, and controlled pumping. The small size of the tips enables rapid control of the required temperature for a chemical reaction. Heat transfer and/or maintenance can be carried out by simply placing the tip in a temperature controlled block.

In some embodiments, the tip is able to contain about 1 to 40 microliters of fluid. In a further embodiment, the tip is able to contain about 5 to 25 microliters of fluid. In an embodiment, the tip contains 20 microliters of fluid. In some instances, a tip can contain 1 microliter of fluid or less. In other instances, a tip can contain up to 100 microliters.

Where desired, the end of the tip can be blotted onto an absorbent material (for example incorporated into a disposable cartridge) prior to introduction of the next assay component to avoid contamination with a small amount of sample and/or reagent. Due to physical forces, any liquid drawn into a subject tip can be held at any desired location with minimal risk of the liquid draining out, even when held in a vertical orientation.

The assay unit (for example, an assay tip) can be coated with assay capture reagents prior to use, using similar fluidics as in the assay (for example, controlled capillary or mechanical aspiration).

A capture surface (also referred to herein as a reaction site) can be formed by a binding antibody or other capture reagents bound covalently or by adsorption to the assay unit. The surface can then dried and maintained in dry condition until used in an assay. In an embodiment, there is a reaction site for each analyte to be measured.

In an embodiment, the assay unit can be moved into fluid communication with the reagent unit and/or a sample collection unit, such that a reagent or sample can interact with a reaction site where bound probes can detect an analyte of interest in the bodily fluid sample. A reaction site can then provide a signal indicative of the presence or concentration of the analyte of interest, which can then be detected by a detection device described herein.

In some embodiments, the location and configuration of a reaction site is an important element in an assay device. Most, if not all, disposable immunoassay devices have been configured with their capture surface as an integral part of the device.

In one embodiment, a molded plastic assay unit is either commercially available or can be made by injection molding with precise shapes and sizes. For example, the characteristic dimension can be a diameter of 0.05-3 mm or can be a length of 3 to 30 mm. The units can be coated with capture reagents using method similar to those used to coat microtiter plates but with the advantage that they can be processed in bulk by placing them in a large vessel, adding coating reagents and processing using sieves, holders, and the like to recover the pieces and wash them as needed.

The assay unit can offer a rigid support on which a reactant can be immobilized. The assay unit is also chosen to provide appropriate characteristics with respect to interactions with light. For example, the assay unit can be made of a material, such as functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, PMMA, ABS, or combinations thereof. In an embodiment, an assay unit comprises polystyrene. Other appropriate materials may be used in accordance with the present invention. A transparent reaction site may be advantageous. In addition, in the case where there is an optically transmissive window permitting light to reach an optical detector, the surface may be advantageously opaque and/or preferentially light scattering.

A reactant immobilized at the capture surface can be anything useful for detecting an analyte of interest in a sample of bodily fluid. For instance, such reactants include, without limitation, nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or noncovalent, via a linker moiety, or tethering them to an immobilized moiety. Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art. Surface immobilization can also be achieved via a Poly-L Lysine tether, which provides a charge-charge coupling to the surface.

The assay units can be dried following the last step of incorporating a capture surface. For example, drying can be performed by passive exposure to a dry atmosphere or via the use of a vacuum manifold and/or application of clean dry air through a manifold.

In many embodiments, an assay unit is designed to enable the unit to be manufactured in a high volume, rapid manufacturing processes. For example, tips can be mounted in large-scale arrays for batch coating of the capture surface into or onto the tip. In another example, tips can be placed into a moving belt or rotating table for serial processing. In yet another example, a large array of tips can be connected to vacuum and/or pressure manifolds for simple processing.

In an embodiment, an assay unit can be operably coupled with a fluid transfer device. The fluid transfer device can be operated under automatic control without human interaction. In assay units comprising tips, the control of the installed height of a disposable liquid tip relies on the tapered interference attachment of the tip to the liquid dispenser. A fluid transfer device can engage the tip. In some instances, the immersion length of a tip in liquid to be transferred must be known to minimize the liquid contact with the outside of the tip which may be uncontrolled. In order to couple or adhere a tip to the fluid transfer device a hard stop can be molded at the bottom of the tapered connector which engages the nozzle of the dispenser. An air tight seal can be made by an o-ring that is half way up the taper or in the flat bottom of the nozzle. By separating the seal function of the tip from the controlled height of the tip both can be separately adjusted. The modular device and fluid transfer device can enable many assays to be performed in parallel.

The reagent units of a device can store reagents that are required to perform a give chemical reaction for detecting a given analyte of interest. Liquid reagents can be dispensed into small capsules that can be manufactured from a variety of materials including, without limitation, plastic such as polystyrene, polyethylene, or polypropylene. In some embodiments, the reagent units are cylindrical cups. Two examples of a reagent unit 401, 402 comprising a cup are shown in FIGS. 4A and 4B. Where desired, the units 401, 402 fit snugly into cavities in a housing of a device. The units 401, 402 can be sealed on the open surface to avoid spilling the reagents 411, 412 onboard. In some embodiments, the seal is an aluminized plastic and can be sealed to the cup by thermal bonding. A unit can be of any shape as is necessary to contain a reagent. For example, a cylindrical shaped reagent unit 401 is shown in FIG. 4A, and the reagent unit contains a liquid reagent 411. A different shaped reagent unit 402 is illustrated in FIG. 4B also contain a liquid reagent 412. Both exemplary reagent units 401, 402 comprise optional slight modifications near the top surface that allow the units 401, 402 to fit snugly into a housing of a device as described herein.

In many embodiments of the invention the reagent units are modular. The reagent unit can be designed to enable the unit to be manufactured in a high volume, rapid manufacturing processes. For example, many reagent units can be filled and sealed in a large-scale process simultaneously. The reagent units can be filled according to the type of assay or assays to be run by the device. For example, if one user desires different assays than another user, the reagent units can be manufactured accordingly to the preference of each user, without the need to manufacture an entire device. In another example, reagent units can be placed into a moving belt or rotating table for serial processing.

In another embodiment, the reagent units are accommodated directly into cavities in the housing of a device. In this embodiment, a seal can be made onto areas of housing surrounding the units.

Reagents according to the present invention include without limitation wash buffers, enzyme substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies, or other materials necessary to run an assay on a device. An enzyme-labeled conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments, the reagents comprise immunoassay reagents. In general, reagents, especially those that are relatively unstable when mixed with liquid, are confined separately in a defined region (for example, a reagent unit) within the device.

In some embodiments, a reagent unit contains approximately about 5 microliters to about 1 milliliter of liquid. In some embodiments, the unit may contain about 20-200 microliters of liquid. In a further embodiment, the reagent unit contains 100 microliters of fluid. In an embodiment, a reagent unit contains about 40 microliters of fluid. The volume of liquid in a reagent unit may vary depending on the type of assay being run or the sample of bodily fluid provided. In an embodiment, the volumes of the reagents do not have to predetermined, but must be more than a known minimum. In some embodiments, the reagents are initially stored dry and dissolved upon initiation of the assay being run on the device.

In an embodiment, the reagent units can be filled using a siphon, a funnel, a pipette, a syringe, a needle, or a combination thereof. The reagent units may be filled with liquid using a fill channel and a vacuum draw channel. The reagent units can be filled individually or as part of a bulk manufacturing process.

In an embodiment, an individual reagent unit comprises a different reagent as a means of isolating reagents from each other. The reagent units may also be used to contain a wash solution or a substrate. In addition, the reagent units may be used to contain a luminogenic substrate. In another embodiment, a plurality of reagents are contained within a reagent unit.

In some instances, the setup of the device enables the capability of pre-calibration of assay units and the reagent units prior to assembly of disposables of the subject device.
Systems In an aspect, a system of the invention comprises a device comprising assay units and reagent units comprising reagents (both liquid and solid phase reagents). In some embodiments, at least one of the whole device, an assay unit, a reagent unit, or a combination thereof is disposable. In a system of the invention, the detection of an analyte with a device is operated by an instrument. In most embodiments, the instrument, device, and method offer an automated detection system. The automated detection system can be automated based upon a defined protocol or a protocol provided to the system by a user.

In an aspect, a system for automated detection an analyte in a bodily fluid sample comprises a device or cartridge, and a detection assembly or detector for detecting the detectable signal indicative of the presence or absence of the analyte.

In an embodiment, the user applies a sample (for example, a measured or an unmeasured blood sample) to the device and inserts the device into the instrument. All subsequent steps are automatic, programmed either by the instrument (hard wired), the user, a remote user or system, or modification of the instrument operation according to a identifier (for example, a bar code or RFID on the device).

Examples of different functions of that can be carried out using a system of the invention include, but are not limited to, dilution of a sample, removal of parts of a sample (for example, red blood cells (RBCs)), reacting a sample in an assay unit, adding liquid reagents to the sample and assay unit, washing the reagents from the sample and assay unit, and containing liquids during and following use of the device. Reagents can be onboard the device in a reagent unit or in a reagent unit to assembled onto the device.

An automated system can detect a particular analyte in a biological sample (for example, blood) by an enzyme-linked immunosorbent assay (ELISA). The system is amenable to multiplexing and is particularly suited for detecting an analyte of interest present in a small volume of a whole blood sample (for example, 20 microliters or less). The system can also detect analytes in different dilutions of a single sample, allowing different sensitivities to be tested on the same device, when desired. All reagents, supplies, and wastes can be contained on the device of the system.

In use, a sample from a subject is applied to the assembled device and the device is inserted into an instrument. In an embodiment, an instrument can begin processing the sample by some combination of removal of red cells (blood sample), dilution of the sample, and movement the sample to the assay unit. In an embodiment with multiplexed assays, a plurality of assay units are used and a portion of the sample is moved to individual assay units in sequence or in parallel. Assays can then be performed by a controlled sequence of incubations and applications of reagents to the capture surfaces.

An exemplary fluid transfer device is comprised of any component required to perform and/or read the assay. Example of components include, but are not limited to, pumps to aspirate and eject accurately known fluid volumes from wells or units of the device, at least one translational stage for improving the precision and accuracy of the movement within the system, a detector to detect an analyte in an assay unit, and temperature regulation means to provide a regulated temperature environment for incubation of assays. In an embodiment of the invention, the instrument controls the temperature of the device. In a further embodiment, the temperature is in the range of about 30-40 degrees Celsius. In some embodiments, the temperature control by the system can comprise active cooling. In some instances, the range of temperature is about 0-100 degrees Celsius. For example, for nucleic acid assays, temperatures up to 100 degrees Celsius can be achieved. In an embodiment, the temperature range is about 15-50 degrees Celsius. A temperature control unit of the system can comprise a thermoelectric device, such as a Peltier device.

Cartridges, devices, and systems as described herein can offer many features that are not available in existing POC systems or integrated analysis systems. For example, many POC cartridges rely on a closed fluidic system or loop to handle small volumes of liquid in an efficient manner. The cartridges and fluidic devices described herein can have open fluid movement between units of the cartridge. For example, a reagent can be stored in a unit, a sample in a sample collection unit, a diluent in a diluent unit, and the capture surface can be in an assay unit, wherein in one state of cartridge, none of the units are in fluid communication with any of the other units. Using a fluid transfer device or system as described herein, the units do not have to be in fluid communication with each other in a state. The units can be movable relative to each other in order to bring some units into fluid communication. For example, a fluid transfer device can comprise a head that engages an assay unit and moves the assay unit into fluidic communication with a reagent unit.

The devices and systems herein can provide an effective means for high throughput and real-time detection of analytes present in a bodily fluid from a subject. The detection methods may be used in a wide variety of circumstances including identification and quantification of analytes that are associated with specific biological processes, physiological conditions, disorders or stages of disorders. As such, the systems have a broad spectrum of utility in, for example, drug screening, disease diagnosis, phylogenetic classification, parental and forensic identification, disease onset and recurrence, individual response to treatment versus population bases, and monitoring of therapy. The subject devices and systems are also particularly useful for advancing pre-clinical and clinical stage of development of therapeutics, improving patient compliance, monitoring ADRs associated with a prescribed drug, developing individualized medicine, outsourcing blood testing from the central laboratory to the home or on a prescription basis, and monitoring therapeutic agents following regulatory approval. The devices and systems can provide a flexible system for personalized medicine. Using the same system, a device can be changed or interchanged along with a protocol or instructions to a programmable processor of the systems to perform a wide variety of assays as described. The systems and devices herein offer many features of a laboratory setting in a desk-top or smaller size automated instrument.

In some embodiments a patient may be provided with a plurality of devices to be used for detecting a variety of analytes. A subject may, for example, use different fluidic devices on different days of the week. In some embodiments the software on the external device associating the identifier with a protocol may include a process to compare the current day with the day the fluidic device is to be used based on a clinical trial for example. In another embodiment, the patient is provided different reagent units and assay units that can be fit into a housing of a device interchangeably. In yet another embodiment, as described the patient does not need a new device for each day of testing, but rather, the system can be programmed or reprogrammed by downloading new instructions from, e.g. an external device such as a server. If for example, the two days of the week are not identical, the external device can wirelessly send notification to the subject using any of the methods described herein or known in the art to notify them of the proper device and/or proper instructions for the system. This example is only illustrative and can easily be extended to, for example, notifying a subject that a fluidic device is not being used at the correct time of day.

For example, a cartridge as illustrated in FIG. 1 can comprise a variety of assay units and reagent units. The assay units can comprise a capture surface according to an analyte to be detected. The assay units can then be assembled with the rest of the device in a just-in-time fashion. In many prior art POC devices, the capture surface is integral to the device and if the capture surface is incorrect or not properly formed, the whole device is bad. Using a device as described herein, the capture surface and/or assay unit can be individually quality controlled and customized independently of the reagent units and the housing of the device.

Reagent units can be filled with a variety of reagents in a similar just-in-time fashion. This provides flexibility of the device being customizable. In addition, the reagent units can be filled with different volumes of reagents without affecting the stability of a device or the chemical reactions to be run within the device. Coupled with a system as described with a fluid transfer device, the devices and units described herein offer flexibility in the methods and protocols of the assays to be run. For example, a batch of similar devices containing the same reagents can be given to a patient pool for a clinical trial. Half way through the clinical trial, a user identifies that the assay could be optimized by changing the dilution of the sample and the amount of reagent provided to the assay unit. As provided herein, the assay can be changed or optimized by only changing the instructions to a programmable processor of the fluid transfer device. For example, the batch of cartridges in the patient pool had excess diluent loaded on the cartridge. The new protocol demands four times as much diluent as the previous protocol. Due to the methods and systems provided herein, the protocol can be changed at a central server and sent to all the systems for executing the methods with the devices without having to provide new devices to the patient pool. In other words, a POC device and system as described herein can offer much of the flexibility of a standard laboratory practice where excess reagents and often excess sample are often available.

In some instances, wherein the units of the cartridge are separate, devices and systems provide flexibility in construction of the systems described herein. For example, a cartridge can be configured to run 8 assays using an array of assay units and an array of reagent units. Due to the features of the cartridge as described herein, the same housing, or a housing of the same design can be used to manufacture a cartridge with up to 8 different assays than the previous cartridge. This flexibility is difficult to achieve in many current POC device designs because of the closed systems and fluid channels, and therefore the devices may not be modular or as easy to assemble as described.

Currently, a need exists for the detecting more than one analyte where the analytes are present in widely varying concentration range, for example, one analyte is in the pg/ml concentration range and another is in the ug/ml concentration range. The system as described herein has the ability to simultaneously assay analytes that are present in the same sample in a wide concentration range. Another advantage for being able to detect concentrations of different analytes present in a wide concentration range is the ability to relate the ratios of the concentration of these analytes to safety and efficacy of multiple drugs administered to a patient. For example, unexpected drug-drug interactions can be a common cause of adverse drug reactions. A real-time, concurrent measurement technique for measuring different analytes would help avoid the potentially disastrous consequence of adverse drug-drug interactions.

Being able to monitor the rate of change of an analyte concentration and/or or concentration of PD or PK markers over a period of time in a single subject, or performing trend analysis on the concentration, or markers of PD, or PK, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

Accordingly, the data generated with the use of the subject fluidic devices and systems can be utilized for performing a trend analysis on the concentration of an analyte in a subject.

Often, 8 assays on the same cartridge may require different dilutions or pre-treatments. The range of dilution can be substantial between assays. Many current POC devices offer a limited range of dilution and therefore a limited number of assays that can be potentially carried out on the POC device. However, a system and/or cartridge as described herein can offer a large range of dilutions due to the ability of to serially dilute a sample. Therefore, a large number of potential assays can be performed on a single cartridge or a plurality of cartridges without modifying the detector or reading instrument for the assays.

In an example, a system as provided herein is configured to run multiple (e.g., five or more) different target analyte detection assays. In order to bring the expected analyte concentration within the range of detection of an immunoassay as described herein and commonly used in the POC field, a sample must be diluted e.g., 3:1, 8:1, 10:1, 100:1, and 2200:1, to run each of the five assays. Because the fluid transfer device is able to hold and move fluid within the device, serial dilutions can be performed with a system as described herein to achieve these five different dilutions and detect all five different target analytes. As described above, the protocol for performing the assays is also capable of being adjusted without modifying the device or the system.

In a laboratory setting with traditional pipetting, typically larger volumes of sample are used than in a POC setting. For example, a laboratory may analyze a blood sample withdrawn from the arm of a patient in a volume in the milliliter range. In a POC setting, many devices and users demand that the process is fast, easy and/or minimally invasive, therefore, small samples (on the order of a volume in the microliter range) such as one obtained by a fingerstick) are typically analyzed by a POC device. Because of the difference in sample, current POC devices can lose flexibility in running an assay that is afforded in a laboratory setting. For example, to run multiple assays from a sample, a certain minimum volume can be required for each assay to allow for accurate detection of an analyte, therefore putting some limits on a device in a POC setting.

In another example, a system and/or fluid transfer device as described herein provides a great deal of flexibility. For example, the fluid transfer device can be automated to move an assay unit, an assay tip, or an empty pipette from one unit of the device to a separate unit of the device, not in fluid communication with each other. In some instances, this can avoid cross-contamination of the units of a device as described. In other instances, it allows for the flexibility of moving several fluids within a device as described into contact with each other according to a protocol or instructions. For example, a cartridge comprising 8 different reagents in 8 different reagent units can be addressed and engaged by a fluid transfer device in any order or combination as is instructed by a protocol. Therefore, many different sequences can be run for any chemical reaction to run on the device. Without changing the volume of the reagents in the cartridge or the type of reagents in the cartridge, the assay protocol can be different or modified without the need for a second cartridge or a second system.

For example, a user orders a cartridge with a specific type of capture surface and specific reagents to run an assay to detect an analyte (for example, C-reactive protein (CRP)) in a sample. The protocol the user originally planned for may require 2 washing steps and 3 dilution steps. After the user has received the device and system, the user has decided that the protocol should actually have 5 washing steps and only 1 dilution step. The devices and systems herein can allow the flexibility for this change in protocol without having to reconfigure the device or the system. In this example, only a new protocol or set of instructions are needed to be sent to the programmable processor of the system or the fluid transfer device.

In another example, a system as provided herein is configured to run five different target analyte detection assays, wherein each assay needs to be incubated at a different temperature. In many prior art POC devices, incubation of multiple assays at different temperatures is a difficult task because the multiple assays are not modular and the capture surfaces cannot be moved relative to the heating device. In a system as described herein, wherein an individual assay unit is configured to run a chemical reaction, an individual assay unit can be place in an individual heating unit. In some embodiments, a system comprises a plurality of heating units. In some instances, a system comprises at least as many heating units as assay units. Therefore, a plurality of assays can be run as a plurality of temperatures.

Systems and devices as described herein can also provide a variety of quality control measures not previously available with many prior art POC devices. For example, because of the modularity of a device, the assay units and reagents units can be quality controlled separately from each other and/or separately from the housing and/or separately from a system or fluid transfer device. Exemplary methods and systems of quality control offered by the systems and devices herein are described.

A system as described can run a variety of assays, regardless of the analyte being detected from a bodily fluid sample. A protocol dependent on the identity of the device may be transferred from an external device where it can be stored to a reader assembly to enable the reader assembly to carry out the specific protocol on the device. In some embodiments, the device has an identifier (ID) that is detected or read by an identifier detector described herein. The identifier detector can communicate with a communication assembly via a controller which transmits the identifier to an external device. Where desired, the external device sends a protocol stored on the external device to the communication assembly based on the identifier. The protocol to be run on the system may comprise instructions to the controller of the system to perform the protocol, including but not limited to a particular assay to be run and a detection method to be performed. Once the assay is performed by the system, a signal indicative of an analyte in the bodily fluid sample is generated and detected by a detection assembly of the system. The detected signal may then be communicated to the communications assembly, where it can be transmitted to the external device for processing, including without limitation, calculation of the analyte concentration in the sample.

In some embodiments, the identifier may be a bar code identifier with a series of black and white lines, which can be read by an identifier detector such as a bar code reader, which are well known. Other identifiers could be a series of alphanumerical values, colors, raised bumps, or any other identifier which can be located on a device and be detected or read by an identifier detector. The identifier detector may also be an LED that emits light which can interact with an identifier which reflects light and is measured by the identifier detector to determine the identity of a device. In some embodiments the identifier may comprise a storage or memory device and can transmit information to an identification detector. In some embodiments a combination of techniques may be used. In some embodiments, the detector is calibrated by used of an optical source, such as an LED.

In an example, a bodily fluid sample can be provided to a device, and the device can be inserted into a system. In some embodiments the device is partially inserted manually, and then a mechanical switch in the reader assembly automatically properly positions the device inside the system. Any other mechanism known in the art for inserting a disk or cartridge into a system may be used. In some embodiments, manual insertion may be required.

In some embodiments a method of automatically selecting a protocol to be run on a system comprises providing a device comprising an identifier detector and an identifier; detecting the identifier; transferring said identifier to an external device; and selecting a protocol to be run on the system from a plurality of protocols on said external device associated with said identifier.

In an aspect, a system for automated detection of a plurality of analytes in a bodily fluid sample is disclosed that comprises: a fluidic device (such as those described herein) comprising: a sample collection unit configured to contain the bodily fluid sample; an array of assay units, wherein an individual assay unit of said array of assay units is configured to run a chemical reaction that yields a signal indicative of an individual analyte of said plurality of analytes being detected; and an array of reagent units, wherein an individual reagent unit of said array of reagent units contains a reagent. The system further comprises a fluid transfer device comprising a plurality of heads, wherein an individual head of the plurality of heads is configured to engage the individual assay unit, and wherein said fluid transfer device comprises a programmable processor configured to direct fluid transfer of the bodily fluid sample from the sample collection unit and the reagent from the individual reagent unit into the individual assay unit. For example, an individual assay unit comprises a reagent and is configured is to run a chemical reaction with that reagent.

In some instances, the configuration of the processor to direct fluid transfer effects a degree of dilution of the bodily fluid sample in the array of assay units to bring signals indicative of the plurality of analytes being detected within a detectable range, such that said plurality of analytes are detectable with said system. In an example, the bodily fluid sample comprises at least two analytes that are present at concentrations that differ by at least 2, 5, 10, 15, 50, or 100 orders of magnitude. In an example the bodily fluid sample is a single drop of blood. In an embodiment, the concentrations of at least two analytes present in a sample differs by up to 10 orders of magnitude (for example, a first analyte is present at 0.1 pg/mL and a second analyte is present at 500 ug/mL. In another example, some protein analytes are found at concentrations of greater than 100 mg/mL, which can extend the range of interest to about twelve orders of magnitude.

A degree of dilution of the bodily fluid sample can bring the signals indicative of the at least two analytes within the detectable range. In many instances, a system further comprises a detector, such as a photomultiplier (PMT). With a photomultiplier, for example, a detectable range of the detector can be about 10 to about 10 million counts per second. Each count corresponds to a single photon. In some instances, PMTs are not 100% efficient and the observed count rate may be slightly lower than, but still close to, the actual number of photons reaching the detector per unit time. In some instances, counts are measured in about ten intervals of about one second and the results are averaged. In some embodiments, ranges for assays are 1000-1,000,000 counts per second when using a PMT as a detector. In some instances, count rates as low as 100 per second and count rates as high as 10,000,000 are measurable. The linear response range of PMTs (for example, the range where count rate is directly proportional to number of photons per unit time) can be about 1000-3,000,000 counts per second. In an example, an assay has a detectable signal on the low end of about 200-1000 counts per second and on the high end of about 10,000-2,000,000 counts per second. In some instances for protein biomarkers, the count rate is directly proportional to alkaline phosphatase bound to the capture surface and also directly proportional to the analyte concentration. Other exemplary detectors include avalanche photodiodes, avalanche photodiode arrays, CCD arrays, supercooled CCD arrays. Many other detectors have an output that is digital and generally proportional to photons reaching the detector. The detectable range for exemplary detectors can be suitable to the detector being used.

An individual head of a fluid transfer device can be configured to adhere to the individual assay unit. The fluid transfer device can be a pipette, such as an air-displacement pipette. The fluid transfer device can be automated. For example, a fluid transfer device can further comprise a motor in communication with a programmable processor and the motor can move the plurality of heads based on a protocol from the programmable processor. As described, an individual assay unit can be a pipette tip, for example, a pipette tip with a capture surface or reaction site.

Often times, in a POC device, such as the systems and devices described herein, the dilution factor must be estimated and reasonably precise. For example, in environments where non-expert users operate the system there needs to be ways of ensuring a dilution of a sample.

As described herein, a fluid transfer device can affect a degree of dilution of a sample to provide accurate assay results. For example, a programmable fluid transfer device can be multi-headed) to dilute or serially dilute samples as well as provide mixing of a sample and diluent. A fluid transfer device can also provide fluid movement in POC devices.

As described, the systems and devices herein can enable many features of the flexibility of laboratory setting in a POC environment. For example, samples can be collected and manipulated automatically in a table top size or smaller device or system. A common issue in POC devices is achieving different dilution ranges when conducting a plurality of assays, wherein the assays may have significantly different sensitivity or specificity. For example, there may be two analytes in a sample, but one analyte has a high concentration in the sample and the other analyte has a very low concentration. As provided, the systems and devices herein can dilute the sample to significantly different levels in order to detect both analytes. For example, if the analyte is in a high concentration, a sample can be serially diluted to the appropriate detection range and provided to a capture surface for detection. In the same system or device, a sample with an analyte in a low concentration may not need to be diluted. In this manner, the assay range of the POC devices and systems provided herein can be expanded from many of the current POC devices.

A fluid transfer device can be part of a system that is a bench-top instrument. The fluid transfer device can comprise a plurality of heads. Any number of heads as is necessary to detect a plurality of analytes in a sample is envisioned for a fluid transfer device of the invention. In an example, a fluid transfer device has about eight heads mounted in a line and separated by a distance. In an embodiment, the heads have a tapered nozzle that engages by press fitting with a variety of tips, such as assay unit or sample collection units as described herein. The tips can have a feature that enables them to be removed automatically by the instrument and disposed into in a housing of a device as described after use. In an embodiment, the assay tips are clear and transparent and can be similar to a cuvette within which an assay is run that can be detected by an optical detector such as a photomultiplier tube.

In an example, the programmable processor of a system can comprise instructions or commands and can operate a fluid transfer device according to the instructions to transfer liquid samples by either withdrawing (for drawing liquid in) or extending (for expelling liquid) a piston into a closed air space. Both the volume of air moved and the speed of movement can be precisely controlled, for example, by the programmable processor.

Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done in similar fashion. Incubation of liquid samples and reagents with a capture surface on which is bound a capture reagent (for example an antibody) can be achieved by drawing the appropriate liquid into the tip and holding it there for a predetermined time. Removal of samples and reagents can be achieved by expelling the liquid into a reservoir or an absorbent pad in a device as described. Another reagent can then be drawn into the tip according to instructions or protocol from the programmable processor.

Figure 11:
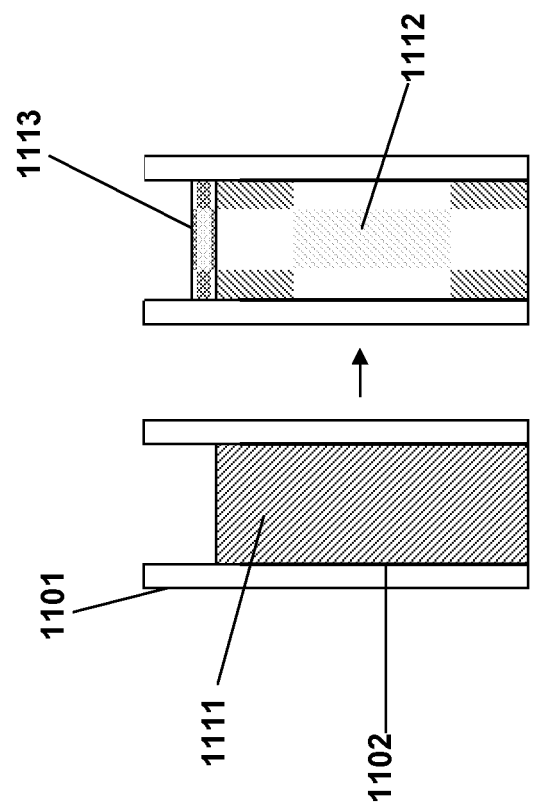
FIG. 11 illustrates a thin film, for example, contamination, within the tip when a liquid is expelled and another liquid aspirated.

In an example as illustrated in FIG. 11, a liquid 1111 previously in a tip 1101 can leave a thin film 1113 within the tip 1101 when expelled. Therefore, a system can use the action of the leading (for example uppermost) portion of the next liquid 1112 to scour the previously present liquid 1111 from the tip 1101. The portion of the subsequent liquid contaminated with the liquid previously present 1113 can be held within the top of the tip 1101 where it does not continue to interact with the capture surface 1102. The capture surface 1102 can be in a defined area of the tip 1101 such that the previous liquid 1111 does not react with the capture surface 1102, for example as shown in FIG. 11, the capture surface 1102 occupies a defined portion of the cylindrical part of the tip 1101 not extending all the way up to the boss of the tip. In many instances, incubation time is short (for example 10 minutes) and separation of the contaminated zone of liquid is relatively large (>1 mm) so diffusion or the active components of the contaminated portion of liquid 1113 does not occur rapidly enough react with the capture surface 1102 during the incubation. For many high sensitivity assays, there is a requirement to remove one reagent or wash the capture surface (for example, a detector antibody which is labeled with the assay signal generator). In an example, a fluid transfer device of a system described herein can provide washing by adding further removal and aspiration cycles of fluid transfer, for example, using a wash reagent. In an example, four wash steps demonstrated that the unbound detector antibody in contact with the capture surface is reduced by a factor of better than $10^6$-fold. Any detector antibody non-specifically bound to the capture surface (highly undesirable) can also be removed during this wash process.

Extension of the range of an assay can be accomplished by dilution of the sample. In POC assay systems using disposable cartridges containing the diluent there is often a practical limit to the extent of dilution. For example, if a small blood sample is obtained by fingerstick (for example, about 20 microliters) is to be diluted and the maximum volume of diluent that can be placed in a tube is 250 microliters, the practical limit of dilution of the whole sample is about 10-fold. In an example herein, a system can aspirate a smaller volume of the sample (for example about 2 microliters) making the maximum dilution factor about 100-fold. For many assays, such dilution factors are acceptable but for an assay like that of CRP (as described in the examples herein) there is a need to dilute the sample much more. Separation-based ELISA assays can have an intrinsic limitation in the capacity of the capture surface to bind the analyte (for example about a few hundred ng/ml for a typical protein analyte). Some analytes are present in blood at hundreds of micrograms/ml. Even when diluted by 100-fold, the analyte concentration may be outside the range of calibration. In an exemplary embodiment of a system, device, and fluid transfer device herein, multiple dilutions can be achieved by performing multiple fluid transfers of the diluent into an individual assay unit or sample collection unit. For example, if the concentration of an analyte is very high in a sample as described above, the sample can be diluted multiple times until the concentration of the analyte is within an acceptable detection range. The systems and methods herein can provide accurate measurements or estimations of the dilutions in order to calculate the original concentration of the analyte.

In an embodiment, a system herein can move a liquid sample and move an assay unit. A system can comprise a heating block and a detector. In order to move a liquid sample, a system may provide aspiration-, syringe-, or pipette-type action. In an exemplary embodiment, a fluid transfer device for moving a liquid sample is a pipette and pipette head system. The number of pipette devices required by the system can be adjusted according to the type of analyte to be detected and the number of assays being run. The actions performed by the pipette system can be automated or operated manually by a user.

Figure 5:
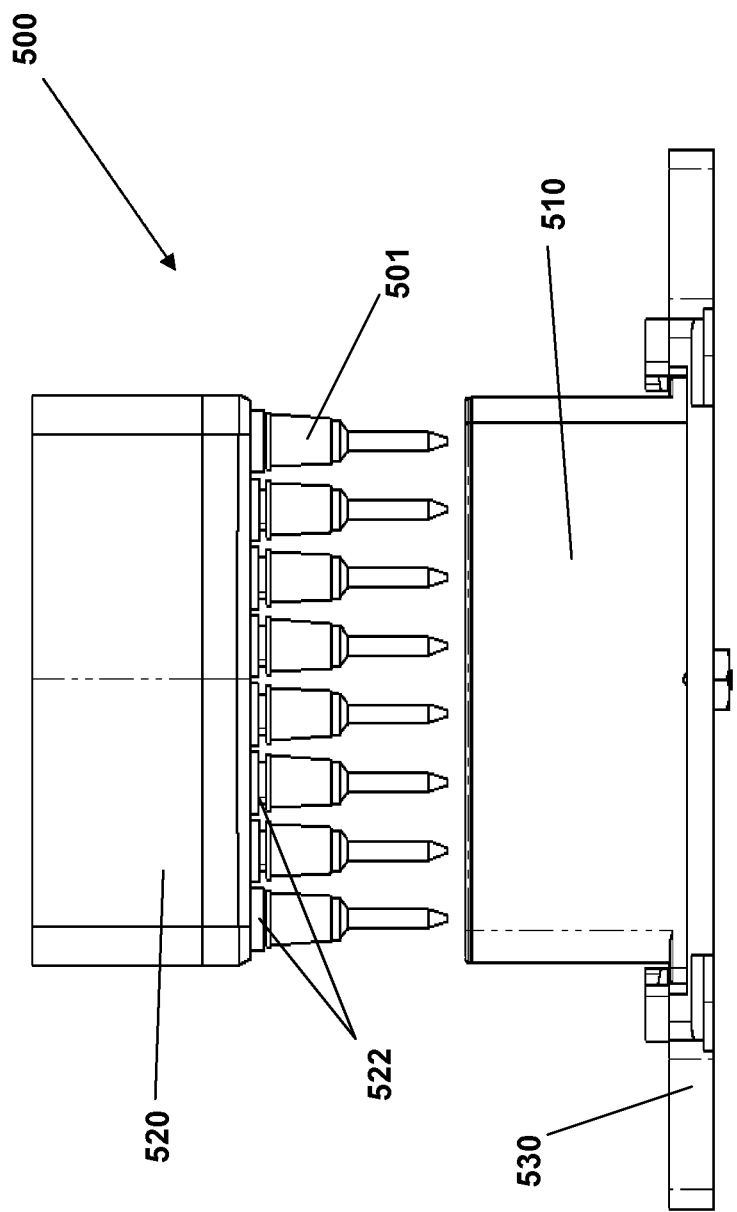
FIG. 5 demonstrates an example of a system comprising a device and a fluid transfer device.

FIG. 5 demonstrates an example of a fluid transfer device 520 and system 500 as described herein. The fluid transfer device system can move eight different or identical volumes of liquid simultaneously using the eight different heads 522. For example, the cartridge (or device as described herein) 510 comprises eight assay units 501. Individual assay units 501 are configured according to the type of assay to be run within the unit 501. Individual assay units 501 may require a certain volume of sample. An individual head 522 can be used to distribute a proper amount of sample to an individual assay unit 501. In this example, each head 522 corresponds to an addressed individual assay unit 501.

The fluid transfer device mechanism 520 can also be used to distribute reagents from the reagent units. Different types of reagents include a conjugate solution, a wash solution, and a substrate solution. In an automated system, the stage 530 on which the device 510 sits can be moved to move the device 510 relative to the positioning of the assay units 501 and heads 522 and according to the steps necessary to complete an assay as demonstrated in FIG. 5. Alternatively, the heads 522 and tips 501 or the fluid transfer device 520 can be moved relative to the position of the device 510.

In some embodiments, a reagent is provided in dry form and rehydrated and/or dissolved during the assay. Dry forms include lyophilized materials and films coated on surfaces.

A system can comprise a holder or engager for moving the assay units or tips. An engager may comprise a vacuum assembly or an assembly designed to fit snugly into a boss of an assay unit tip. For example, a means for moving the tips can be moved in a manner similar to the fluid transfer device heads. The device can also be moved on a stage according to the position of an engager or holder.

In an embodiment, an instrument for moving the tips is the same as an instrument for moving a volume of sample, such as a fluid transfer device as described herein. For example, a sample collection tip can be fit onto a pipette head according to the boss on the collection tip. The collection tip can then be used to distribute the liquid throughout the device and system. After the liquid has been distributed, the collection dip can be disposed, and the pipette head can be fit onto an assay unit according to the boss on the assay unit. The assay unit tip can then be moved from reagent unit to reagent unit, and reagents can be distributed to the assay unit according to the aspiration- or pipette-type action provided by the pipette head. The pipette head can also perform mixing within a collection tip, assay unit, or reagent unit by aspiration- or syringe-type action.

A system can comprise a heating block for heating the assay or assay unit and/or for control of the assay temperature. Heat can be used in the incubation step of a assay reaction to promote the reaction and shorten the duration necessary for the incubation step. A system can comprise a heating block configured to receive an assay unit of the invention. The heating block can be configured to receive a plurality of assay units from a device of the invention. For example, if 8 assays are desired to be run on a device, the heating block can be configured to receive 8 assay units. In some embodiments, assay units can be moved into thermal contact with a heating block using the means for moving the assay units. The heating can be performed by a heating means known in the art.

Figure 6:
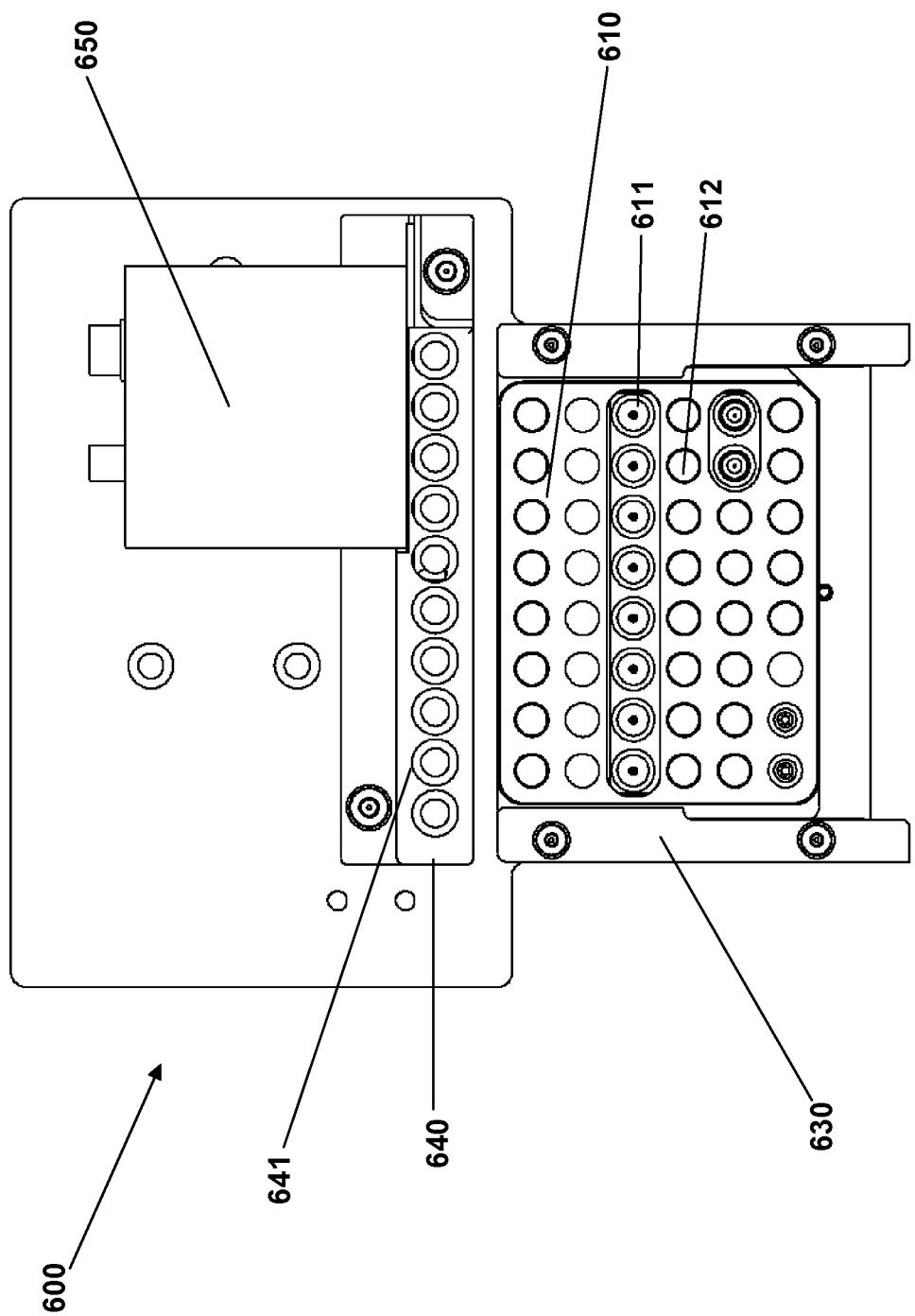
FIG. 6 illustrates an exemplary system of the invention comprising a heating block for temperature control and a detector.

An exemplary system 600 as described herein is demonstrated in FIG. 6. The system 600 comprises a translational stage 630 onto which a device 610 (or cartridge in this example) is placed either manually or automatically or a combination of both. The system 600 also comprises a heating block 640 that can be aligned with the assay units 611 of the device 610. As shown in FIG. 6, the device 610 comprises a series of 8 assay units 611 and multiple corresponding reagent units 612, and the heating block 640 also comprises an area 641 for at least 8 units to be heated simultaneously. Each of the heating areas 641 can provide the same or different temperatures to each individual assay unit 611 according to the type of assay being run or the type of analyte being detected. The system 600 also comprises a detector (such as a photomultiplier tube) 650 for detection of a signal from an assay unit 611 representative of the detection of an analyte in a sample.

In an embodiment, a sensor is provided to locate an assay unit relative to a detector when an assay is detected.

In an embodiment, the detector is a reader assembly housing a detection assembly for detecting a signal produced by at least one assay on the device. The detection assembly may be above the device or at a different orientation in relation to the device based on, for example, the type of assay being performed and the detection mechanism being employed. The detection assembly can be moved into communication with the assay unit or the assay unit can be moved into communication with the detection assembly.

In many instances, an optical detector is provided and used as the detection device. Non-limiting examples include a photodiode, photomultiplier tube (PMT), photon counting detector, avalanche photo diode, or charge-coupled device (CCD). In some embodiments a pin diode may be used. In some embodiments a pin diode can be coupled to an amplifier to create a detection device with a sensitivity comparable to a PMT. Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

A detector can also comprise a light source, such as a bulb or light emitting diode (LED). The light source can illuminate an assay in order to detect the results. For example, the assay can be a fluorescence assay or an absorbance assay, as are commonly used with nucleic acid assays. The detector can also comprise optics to deliver the light source to the assay, such as a lens or fiber optics.

In some embodiments, the detection system may comprise non-optical detectors or sensors for detecting a particular parameter of a subject. Such sensors may include temperature, conductivity, potentiometric signals, and amperometric signals, for compounds that are oxidized or reduced, for example, $O_2$, $H_2O_2$, and $I_2$, or oxidizable/reducible organic compounds.

A device and system may, after manufacturing, be shipped to the end user, together or individually. The device or system of the invention can be packaged with a user manual or instructions for use. In an embodiment, the system of the invention is generic to the type of assays run on different devices. Because components of the device can be modular, a user may only need one system and a variety of devices or assay units or reagent units to run a multitude of assays in a point-of-care environment. In this context, a system can be repeatedly used with multiple devices, and it may be necessary to have sensors on both the device and the system to detect such changes during shipping, for example. During shipping, pressure or temperature changes can impact the performance of a number of components of the present system, and as such a sensor located on either the device or system can relay these changes to, for example, the external device so that adjustments can be made during calibration or during data processing on the external device. For example, if the temperature of a fluidic device is changed to a certain level during shipping, a sensor located on the device could detect this change and convey this information to the system when the device is inserted into the system by the user. There may be an additional detection device in the system to perform these tasks, or such a device may be incorporated into another system component. In some embodiments information may be wirelessly transmitted to either the system or the external device, such as a personal computer or a television. Likewise, a sensor in the system can detect similar changes. In some embodiments, it may be desirable to have a sensor in the shipping packaging as well, either instead of in the system components or in addition thereto. For example, adverse conditions that would render an assay cartridge or system invalid that can be sensed can include exposure to a temperature higher than the maximum tolerable or breach of the cartridge integrity such that moisture penetration.

In an embodiment, the system comprises a communication assembly capable of transmitting and receiving information wirelessly from an external device. Such wireless communication may be Bluetooth or RTM technology. Various communication methods can be utilized, such as a dial-up wired connection with a modem, a direct link such as a T1, ISDN, or cable line. In some embodiments, a wireless connection is established using exemplary wireless networks such as cellular, satellite, or pager networks, GPRS, or a local data transport system such as Ethernet or token ring over a local area network. In some embodiments the information is encrypted before it is transmitted over a wireless network. In some embodiments the communication assembly may contain a wireless infrared communication component for sending and receiving information. The system may include integrated graphic cards to facilitate display of information.

In some embodiments the communication assembly can have a memory or storage device, for example localized RAM, in which the information collected can be stored. A storage device may be required if information can not be transmitted at a given time due to, for example, a temporary inability to wirelessly connect to a network. The information can be associated with the device identifier in the storage device. In some embodiments the communication assembly can retry sending the stored information after a certain amount of time.

In some embodiments an external device communicates with the communication assembly within the reader assembly. An external device can wirelessly or physically communicate with a system, but can also communicate with a third party, including without limitation a patient, medical personnel, clinicians, laboratory personnel, or others in the health care industry.

Figure 7:
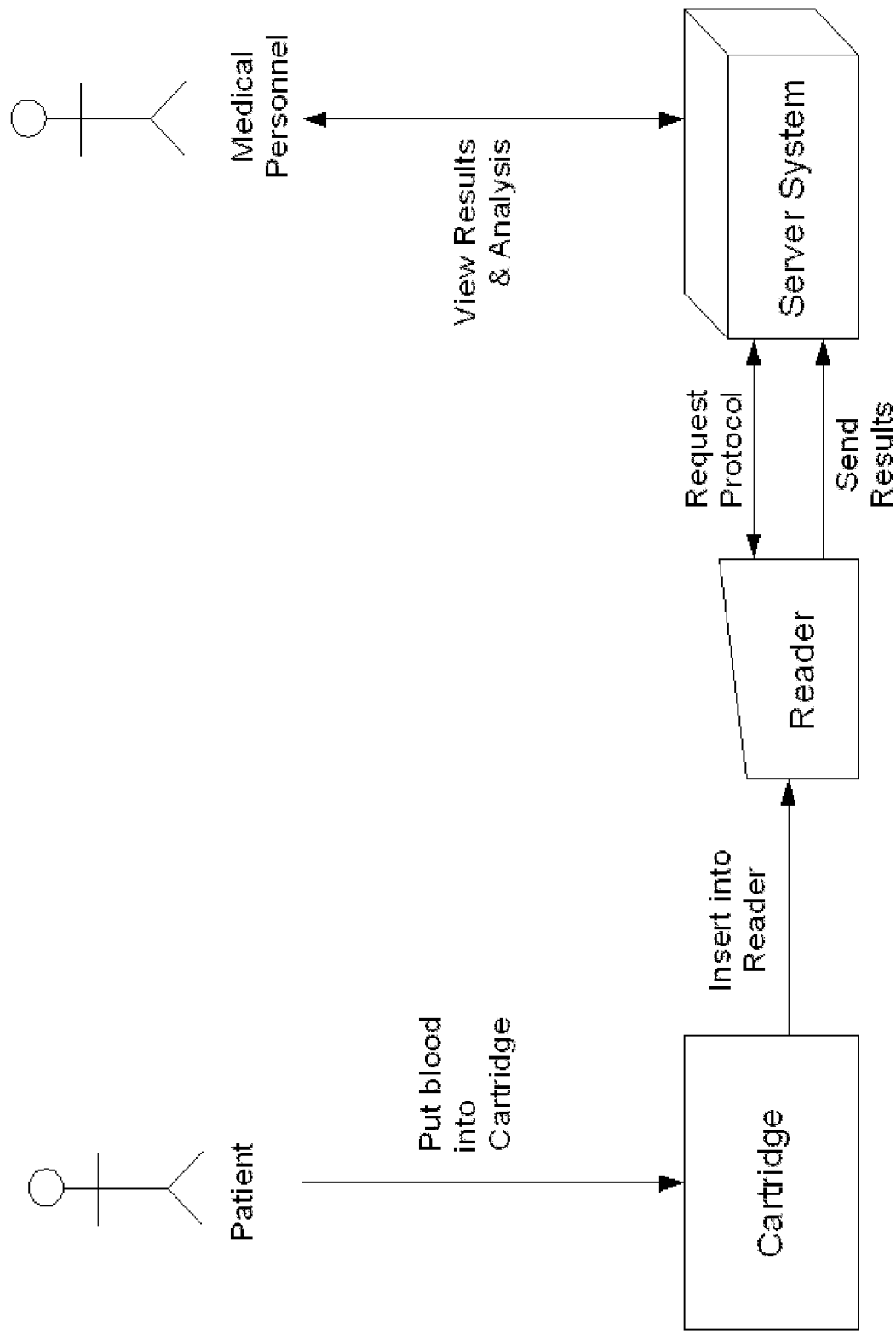
FIG. 7 demonstrates an exemplary a system wherein a patient delivers blood to a device and then the device is inserted into a reader.

An exemplary method and system is demonstrated in FIG. 7. In the example of FIG. 7, a patient delivers a blood sample to a device as described herein and then the device is inserted into a reader, wherein the reader can be desktop system capable of reading an analyte in the blood sample. The reader can be a system as described herein. The reader can be a bench-top or desk-top system and can be capable of reading a plurality of different devices as described herein. The reader or system is capable of carrying out a chemical reaction and detecting or reading the results of the chemical reaction. In the example in FIG. 7, a reader is automated according to a protocol sent from an external device (for example, a server comprising a user interface). A reader can also send the results of the detection of the chemical reaction to the server and user interface. In an exemplary system, the user (for example, medical personnel such as a physician or researcher) can view and analyze the results as well as decide or develop the protocol used to automate the system. Results can also be stored locally (on the reader) or on the server system. The server can also host patient records, a patient diary, and patient population databases.

Figure 8:
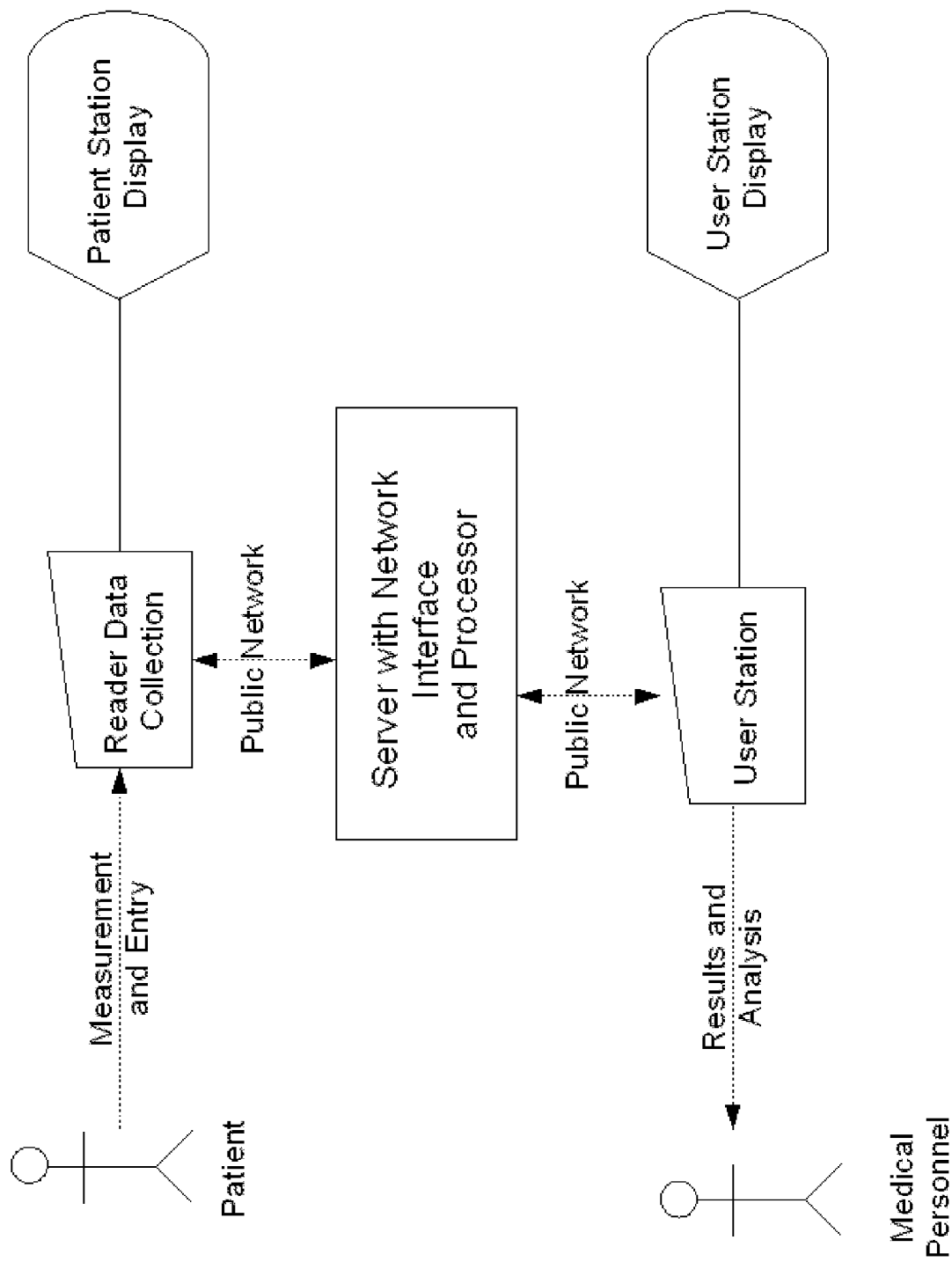
FIG. 8 illustrates the process flow of building a system for assessing the medical condition of a patient.

FIG. 8 illustrates the process flow of building a system for assessing the medical condition of a subject. The patient inputs personal data and or measurements from a device, reader, and/or system as described herein into a database as may be present on a server as described. The system can configured to display the personal data on a patient station display. In some embodiments, the patient station display is interactive and the patient can modify inputted data. The same or a different database contains data from other subjects with a similar medical condition. Data from the other subjects can be historical data from public or private institutions. Data from other subjects may also be internal data from a clinical study.

FIG. 8 also illustrates the flow of data from reader collection data that includes the data from the subject to a server that is connected over a public network. The server can manipulate the data or can just provide the data to a user station. The patient data may also be input to the server separately from the data pertaining to a medical condition that is stored in a database. FIG. 8 also demonstrates a user station display and the flow of information to medical personnel or a user. For example, using the exemplary process flow of FIG. 8, a patient at home can input a bodily fluid sample into a cartridge of the invention as described herein and place it in a system or reader as described herein. The patient can view the data from the system at a patient station display and/or modify or input new data into the process flow. The data from the patient can then travel over a public network, such as the internet, for example, in an encrypted format, to a server comprising a network interface and a processor, wherein the server is located at a central computing hub or in a clinical trial center. The server can use medical condition data to manipulate and understand the data from the user and then send the results over a public network as described to a user station. The user station can be in a medical office or laboratory and have a user station display to display the results of the assay and manipulation of the patient data to the medical personnel. In this example, the medical personnel can receive results and analysis of a sample from a patient from a test that the patient administered in an alternate location such as the patient's home. Other embodiments and example of systems and components of systems are described herein.

In some embodiments the external device can be a computer system, server, or other electronic device capable of storing information or processing information. In some embodiments the external device includes one or more computer systems, servers, or other electronic devices capable of storing information or processing information. In some embodiments an external device may include a database of patient information, for example but not limited to, medical records or patient history, clinical trial records, or preclinical trial records. An external device can store protocols to be run on a system which can be transmitted to the communication assembly of a system when it has received an identifier indicating which device has been inserted in the system. In some embodiments a protocol can be dependent on a device identifier. In some embodiments the external device stores more than one protocol for each device. In other embodiments patient information on the external device includes more than one protocol. In some instances, the external server stores mathematical algorithms to process a photon count sent from a communication assembly and in some embodiments to calculate the analyte concentration in a bodily fluid sample.

In some embodiments, the external device can include one or more servers as are known in the art and commercially available. Such servers can provide load balancing, task management, and backup capacity in the event of failure of one or more of the servers or other components of the external device, to improve the availability of the server. A server can also be implemented on a distributed network of storage and processor units, as known in the art, wherein the data processing according to the present invention reside on workstations such as computers, thereby eliminating the need for a server.

A server can includes a database and system processes. A database can reside within the server, or it can reside on another server system that is accessible to the server. As the information in a database may contains sensitive information, a security system can be implemented that prevents unauthorized users from gaining access to the database.

One advantage of some of the features described herein is that information can be transmitted from the external device back to not only the reader assembly, but to other parties or other external devices, for example without limitation, a PDA or cell phone. Such communication can be accomplished via a wireless network as disclosed herein. In some embodiments a calculated analyte concentration or other patient information can be sent to, for example but not limited to, medical personnel or the patient.

Accordingly, the data generated with the use of the subject devices and systems can be utilized for performing a trend analysis on the concentration of an analyte in a subject.

Another advantage as described herein is that assay results can be substantially immediately communicated to any third party that may benefit from obtaining the results. For example, once the analyte concentration is determined at the external device, it can be transmitted to a patient or medical personnel who may need to take further action. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

By detecting a device based on an identifier associated with a fluidic device after it is inserted in the system, the system allows for fluidic device-specific protocols to be downloaded from an external device and run. In some embodiments an external device can store a plurality of protocols associated with the system or associated with a particular patient or group of patients. For example, when the identifier is transmitted to the external device, software on the external device can obtain the identifier. Once obtained, software on the external device, such as a database, can use the identifier to identify protocols stored in the database associated with the identifier. If only one protocol is associated with the identifier, for example, the database can select the protocol and software on the external device can then transmit the protocol to the communication assembly of the system. The ability to use protocols specifically associated with a device allows for any component of a device of the invention to be used with a single system, and thus virtually any analyte of interest can be detected with a single system.

In some embodiments multiple protocols may be associated with a single identifier. For example, if it is beneficial to detect from the same patient an analyte once a week, and another analyte twice a week, protocols on the external device associated with the identifier can also each be associated with a different day of the week, so that when the identifier is detected, the software on the external device can select a specific protocol that is associated with the day of the week.

In some embodiments a patient may be provided with a plurality of devices to use to detect a variety of analytes. A subject may, for example, use different devices on different days of the week. In some embodiments the software on the external device associating the identifier with a protocol may include a process to compare the current day with the day the device is to be used based on a clinical trial for example. If for example, the two days of the week are not identical, the external device can wirelessly send notification to the subject using any of the methods described herein or known in the art to notify them that an incorrect device is in the system and also of the correct device to use that day. This example is only illustrative and can easily be extended to, for example, notifying a subject that a device is not being used at the correct time of day.

The system can also use a networking method of assessing the medical condition of a subject. A system of communicating information may or may not include a reader for reading subject data. For example, if biomarker data is acquired by a microfluidic point-of-care device, the values assigned to different individual biomarkers may be read by the device itself or a separate device. Another example of a reader would be a bar code system to scan in subject data that has been entered in an electronic medical record or a physician chart. A further example of a reader would consist of an electronic patient record database from which subject data could be directly obtained via the communications network. In this way, the efficacy of particular drugs can be demonstrated in real-time, thus justifying reimbursement of the therapy.

Noncompliance with a medical treatment, including a clinical trial, can seriously undermine the efficacy of the treatment or trial. As such, in some embodiments the system of the present invention can be used to monitor patient compliance and notify the patient or other medical personnel of such noncompliance. For example, a patient taking a pharmaceutical agent as part of medical treatment plan can take a bodily fluid sample which is assayed as described herein, but a metabolite concentration, for example, detected by the system may be at an elevated level compared to a known profile that will indicate multiple doses of the pharmaceutical agent have been taken. The patient or medical personnel may be notified of such noncompliance via any or the wireless methods discussed herein, including without limitation notification via a handheld device such a PDA or cell phone. Such a known profile may be located or stored on an external device described herein.

In an embodiment, the system can be used to identify sub-populations of patients which are benefited or harmed by a therapy. In this way, drugs with varying toxicity that would otherwise be forced from the market can be saved by allocating them only to those who will benefit.

Methods

The devices and methods of the invention provide an effective means for real-time detection of analytes present in a bodily fluid from a subject. The detection methods may be used in a wide variety of circumstances including identification and quantification of analytes that are associated with specific biological processes, physiological conditions, disorders, stages of disorders or stages of therapy. As such, the devices and methods have a broad spectrum of utility in, for example, drug screening, disease diagnosis, phylogenetic classification, parental and forensic identification, disease onset and recurrence, individual response to treatment versus population bases, and monitoring of therapy. The devices and methods are also particularly useful for advancing preclinical and clinical stage of development of therapeutics, improving patient compliance, monitoring ADRs associated with a prescribed drug, individualized medicine, outsourcing blood testing from the central laboratory to the residence of the patient. The device can be employed on a prescription basis, utilized by pharmaceutical companies for monitoring therapeutic agents following regulatory approval or utilized for payors outsourcing blood tests from a central lab.

Accordingly, in an embodiment, the present invention provides a method of detecting an analyte in a bodily fluid sample comprising providing a blood sample to a device or system of the invention, allowing the sample to react within at least one assay unit of the device, and detecting the detectable signal generated from the analyte in the blood sample.

FIG. 1 demonstrates an exemplary embodiment of a device of the invention comprising at least one assay unit and at least one reagent unit. The assay units (for example, designated as sample tips and calibrator tips in FIG. 1) can contain a capture surface and the reagent units can contain items such as conjugates, washes, and substrates. The device exemplified in FIG. 1 also comprises a whole blood sample collection tip, a plasma sample collection tip, a blood input well, a beads well or plasma separation well, a tip touch-off or blotting pad, a dilution well, a diluted plasma sample well or plasma diluent well, collection tip disposal areas.

In an embodiment, a method comprises performing an Enzyme-linked Immunosorbent Assay (ELISA). In an example as described in this paragraph, a sample is provided to a sample collection unit of a device as described herein. The device is then inserted into a system, wherein system detects the type of cartridge or device that is inserted. The system can then communicate with an external device to receive a set of instructions or protocol that allow the system to perform the desired assay or assays of the cartridge. The protocol can be sent to the programmable processor of a fluid transfer device of the system. In an example, the fluid transfer device engages a sample tip of the cartridge and picks up a certain volume of the sample from the sample collection unit and moves it to a pretreatment unit where red blood cells are removed. The plasma of the sample can then be aspirated into a plasma tip or any assay tip by the fluid transfer device according to the protocol. The tip containing the plasma can then pick up a diluent to dilute the sample as is necessary for the assays to be run. Many different dilutions can be carried by using serial dilutions of the sample. For example, each assay tip or assay unit can contain a sample of a different dilution. After the sample is aspirated into an assay unit by the fluid transfer device, the assay unit can then be incubated with the sample to allow any target analyte present to attach to the capture surface. Incubations as described in this example can be at the system or room temperature for any period of time, for example 10 minutes, or can in a heating device of the system as described herein. The assay unit can engage a reagent unit addressed with a reagent corresponding to the assay to be run in each individual assay unit that have a capture surface for that assay. In this example, the first reagent is a detector solution of an ELISA, for example, comprising a detector antibody such as a labeled anti-protein antibody different than the capture surface. The detector solution is then aspirated out of the assay unit and then a wash solution can be aspirated into the assay unit to remove any excess detector solution. Multiple wash steps can be used. The final reagent to be added is an enzymatic substrate which causes the bound detector solution to chemiluminesce. The enzymatic substrate is then expelled from the assay unit and the results of the assay are read by a detector of the system. At each step as described, incubations can occur as necessary as described herein. In this example, the entire process after putting the cartridge into the system is automated and carried out by a protocol or set of instructions to the programmable system.

One exemplary method proceeds with delivering a blood sample into the blood input well. The sample can then be picked up by a collection tip and inserted into the plasma separation well. Alternatively, the blood can be deposited directly into a well containing a blood separator. For example, plasma separation can be carried out by a variety of methods as described herein. In this example, plasma separation proceeds using magnetizable beads and antibodies to remove the components of the blood that are not plasma. The plasma can then be carried by a plasma collection tip as to not contaminate the sample with the whole blood collection tip. In this example, the plasma collection tip can pick-up a predetermined amount of diluent and dilute the plasma sample. The diluted plasma sample is then distributed to the assay units (sample tips) to bind to a capture surface. The assay units can be incubated to allow for a capture reaction to be carried out. The assay unit then can be used to collect a conjugate to bind with the reaction in the assay unit. The conjugate can comprise an entity that allows for the detection of an analyte of interest by a detector, such as an optical detector. Once conjugate has been added to the assay unit, the reaction can be incubated. In an exemplary method using an exemplary device of FIG. 1, a reagent unit containing a wash for the conjugate is then accessed by the assay unit (sample tip) to remove any excess conjugate that can interfere with any analyte detection. After washing away excess conjugate, a substrate can be added to the assay unit for detection. In addition, in the example of FIG. 1 and this method, a calibrator tip assay unit can be used to carry out all of the methods described in this paragraph except the collection and distribution of the sample. Detection and measurements using the calibrator tip assay unit can be used to calibrate the detection and measurements of the analyte from the sample. Other processes and methods similar to those used in this example are described hereinafter.

Any bodily fluids suspected to contain an analyte of interest can be used in conjunction with the system or devices of the invention. For example, the input well or sample collection unit in the example of FIG. 1 can collect of contain any type of commonly employed bodily fluids that include, but are not limited to blood, serum, saliva, urine, gastric and digestive fluid, tears, stool, semen, vaginal fluid, interstitial fluids derived from tumorous tissue liquids extracted from tissue samples, and cerebrospinal fluid. In an embodiment, the bodily fluid is blood and can be obtained by a fingerstick. In an embodiment, the bodily fluid sample is a blood plasma sample.

A bodily fluid may be drawn from a patient and distributed to the device in a variety of ways including, but not limited to, lancing, injection, or pipetting. In one embodiment, a lancet punctures the skin and delivers the sample into the device using, for example, gravity, capillary action, aspiration, or vacuum force. The lancet may onboard the device, or part of a reader assembly, or a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the device, as could occur, for example, with a saliva sample. The collected fluid can be placed into a collection well or unit of the device. In some embodiments, there is a user activated lancet and sample collecting capillary within the device.

The volume of bodily fluid to be used with a method or device described herein is generally less than about 500 microliters, further can be between about 1 to 100 microliters. Where desired, a sample of 1 to 50 microliters, 1 to 40 microliters, 1 to 30 microliters, 1 to 10 microliters or even 1 to 3 microliters can be used for detecting an analyte using the subject fluidic device. In an embodiment, the sample is 20 microliters.

In an embodiment, the volume of bodily fluid used for detecting an analyte utilizing the devices, systems, or methods is one drop of fluid. For example, one drop of blood from a pricked finger can provide the sample of bodily fluid to be analyzed with a device, system, or method of the invention.

In some embodiments, the bodily fluids are used directly for detecting the analytes present in the bodily fluid without further processing. Where desired, however, the bodily fluids can be pre-treated before performing the analysis with a device. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions or using nucleic acid binding resins following the accompanying instructions provided by manufacturers. Where the analyte is a molecule present on or within a cell, extraction can be performed using lysing agents including but not limited to anticoagulants such as EDTA or heparin, denaturing detergent such as SDS or non-denaturing detergent such as Thesit, sodium deoxylate, triton X-100, and tween-20.

In an embodiment, the subject collects a sample of bodily fluid with a syringe. The sample can enter the syringe through a capillary tube. In an embodiment measuring an analyte in a blood sample, the subject performs a fingerstick and touches the outer end of the glass capillary to the blood so that blood is drawn by capillary action and fills the capillary with a volume. In some instances, the sample volume is known. In some embodiments, the sample volume is in the range of about 5-20 microliters or other volume ranges as described herein.

In another embodiment, a method and system is provided to obtain a plasma sample substantially free of red blood cells from a blood sample. When conducting an assay, the analytes are often contained in the blood plasma, and the red blood cells can interfere with a reaction.

Often, when measuring a blood sample, the analytes of interest are in the serum or plasma. For clinical purposes, the final reported concentration of multiple blood tests often needs to relate to the concentration of blood serum or blood plasma in a diluted sample. In many cases, blood serum or blood plasma is the test medium of choice in the lab. Two operations may be necessary prior to running an assay, dilution and red blood cell removal. Blood samples vary significantly in the proportion of the sample volume occupied by red cells (the hematocrit which varies from about 20-60%). Furthermore, in a point-of-care environment when assay systems are operated by non-expert personnel, the volume of sample obtained may not be that which is intended. If a change in volume is not recognized, it can lead to error in the reported analyte concentrations.

In related but separate embodiment, the present invention provides a method of retrieving plasma from a blood sample is provided that comprises mixing a blood sample in the presence of magnetizable particles in a sample collection unit, wherein the magnetizable particles comprise an antibody capture surface for binding to non-plasma portions of the blood sample, and applying a magnetic field above a plasma collection area to the mixed blood sample to effect suspension of the non-plasma portions of the blood sample on top of the plasma collection area, thereby retrieving the plasma from a blood sample.

In order to process blood samples, the device or system of the invention may include a magnetic reagent or object which binds to red cells and enables magnetic removal of red cells from plasma. The reagent can be provided in lyophilized form but also can be present as a liquid dispersion. A reagent comprised of magnetizable particles (for example, about 1 micrometer in size) can be coated with an antibody to a red cell antigen or to some adaptor molecule. In some embodiments, the reagent also contains unbound antibodies to red cell surface antigens, which may be unlabeled or labeled with an adaptor moiety (such as biotin, digoxigenin, or fluorescein). In an embodiment analyzing a blood sample, the red blood cells in a diluted sample co-agglutinate with the magnetizable particles aided by a solution phase antibody. Alternatively, a lectin that recognizes a red cell surface carbohydrate can be used as a co-agglutination agent. Sometimes, combinations of red cell agglutinating agents are used. Alternatively, a device of the invention can comprise a blood filter, such as a pad of glass fiber, to aid in the separation of red blood cells from a sample.

When blood is mixed with a magnetic reagent, a co-agglutination can occur in which many, if not all, of the red cells form a mixed agglutinate with the magnetizable particles. The reagent dissolution and mixing process is driven by repeated aspiration using a tip or collection tip of the invention or a pipette-like tip. After the magnetizable mass has formed, the mass can be separated from the blood plasma by use of a magnet to hold the mass in place as plasma is allowed to exit the tip. In an embodiment, the plasma exits the tip by gravity in a vertical orientation, while the magnet holds the mass in place. In another embodiment, the plasma exits the tip by vacuum or pressure means, while the mass is held within the tip. The plasma can be deposited into a well, another collection tip, or assay unit of the invention.

An example of a plasma separation method of the invention is demonstrated in FIGS. 9A through 9E. In FIG. 9A, a whole blood sample 901 has been aspirated into a sample tip 910 as described herein, for example in the amount of about 20 microliters. The whole blood sample 901 is then deposited into a separation well 920 (for example, a well containing magnetic beads or particles) of an example device. FIG. 9B illustrates a method of suspending and mixing a magnetic reagent in the whole blood sample 902 in a separation well (for example, magnetic bead particles and free binding molecules). FIG. 9C demonstrates a 10 microliter air slug 930 that can be used to prevent loss from the tip 910. The mixed whole blood sample and magnetic reagent 902 are incubated for several seconds (for example, 60 to 180 seconds) to allow an agglutination reaction to occur.

FIG. 9D demonstrates the application of a magnetic field 940 to the whole blood cell and magnetic reagent mixture 902. The magnetic field 940 can be applied by a magnetic collar 942 that is incorporated with a system or with any magnetic means known in the art. The magnetic field 940 attracts any particles that have adhered to the magnetic reagent. In this way, the plasma 903, which does not adhere with the magnetic reagent, can be separated from non-plasma portions of a whole blood sample.

FIG. 9E demonstrates a method of distributing a blood plasma sample 903, as separated by the magnetic reagent described herein, into a well or unit 950 of a device as described herein. The blood plasma sample 903 can also be distributed to a collection tip or assay unit, as well as any other sort of assay device as obvious to one skilled in the art. In FIG. 9E, the magnetic field 940 is shown to move with the tip 910 distributing the blood plasma sample 903. In this example, 5 to 8 microliters of plasma have been removed from a 20 microliter whole blood sample 1 to 99% of a whole blood sample can be plasma separated using a method of the invention. In an embodiment, 25 to 60% of the volume of the whole blood sample is plasma that can be separated.

Other exemplary steps of a method as described can be completed. In order to move the blood plasma sample to another well or unit, a capillary plasma collection tip (which can be operated by a robotic system or any other system of the invention) collects the blood plasma sample by capillary and aspiration force. Another step can comprise distributing the plasma sample in a diluent, and the sample can then be diluted by the diluent. The diluted blood plasma sample can then be collected by the collection tip in a predetermined volume. The diluted blood plasma sample can then be mixed and distributed into a well or unit of a device to be distributed to one or a plurality of assay units of a device of the invention. The sample can also be distributed into any other type of device, such as a microtiter plate, as would be obvious to those skilled in the art.

The example process demonstrated in FIGS. 9A through 9E can be used with other devices and systems, other than those disclosed herein. For example, a fluid transfer tip can contain the agglutinated mass and the plasma could be deposited into a microtiter plate. Other devices and systems as would be obvious to those skilled in the art could be utilized to execute the example blood plasma separation as disclosed herein.

The sample of bodily fluid can also be diluted in a variety of other manners, such as using a sample collection device capable of dilution. The housing of the sample collection device can comprise a tube. In the tube, two moveable seals can contain a volume of a diluent. In a preferable embodiment, the volume of the diluent is predetermined, e.g., in about the range of 50 microliters to 1 milliliter, preferably in the range of about 100 microliters to 500 microliters.

In an aspect, a method for automated detection of a plurality of analytes in a bodily fluid sample is provided that comprises: providing the bodily fluid sample to a fluidic device, wherein the fluidic device comprises: a sample collection unit configured to contain the bodily fluid sample; an array of assay units, wherein an individual assay unit of said array of assay units is configured to run a chemical reaction that yields a signal indicative of an individual analyte of said plurality of analytes being detected; and an array of reagent units, wherein an individual reagent unit of said array of reagent units contains a reagent. The method can also comprise engaging the individual assay unit using a fluid transfer device. Continuing the method, bodily fluid sample can be transferred from the sample collection unit to the individual assay unit using the fluid transfer device and the reagent from the individual reagent unit can be transferred to the individual assay unit, thereby reacting the reagent with the bodily fluid sample to yield the signal indicative of the individual analyte of the plurality of analytes being detected. In some embodiments, the fluid transfer device comprises a plurality of heads, wherein an individual head of the plurality of heads is configured to engage the individual assay unit; and wherein said fluid transfer device comprises a programmable processor configured to direct fluid transfer of the bodily fluid sample from the sample collection unit and the reagent from the individual reagent unit into the individual assay unit.

In some instances, instructions are provided to the programmable processor, for example, by a user, a subject, or the manufacturer. Instructions can be provided from an external device, such as a personal electronic device or a server. The instructions can direct the step of transferring the bodily fluid sample to the individual assay unit. For example, the step of transferring the bodily fluid sample can affect a degree of dilution of the bodily fluid sample in the individual assay unit to bring the signal indicative the individual analyte of the plurality of analytes being detected within a detectable range. In some examples, the degree of dilution of the bodily fluid sample brings the signals indicative of the at least two individual analytes within a detectable range as described herein.

Pattern recognition techniques can be used to determine if the detection of an analyte or a plurality of analytes by a method as described herein is within or outside a certain range. For example, detectable signals outside the reportable range can be rejected. The certain range can be established during calibration of a fluidic device the reagent and assay units. For example, the range is established when a device is assembled in a just-in-time fashion.

In some instances, if the detectable signal of an analyte as detected with a lower dilution factor or degree of dilution exceeds that for a higher dilution factor, the lower dilution result can be rejected as invalid. In most instances, concentrations of an analyte in a sample as derived from signals from samples with different degrees of dilution get lower as the degree of dilution becomes greater. If this does happen, an assay result can be verified. The systems, devices, and methods herein provide the flexibility of quality control rules such as those described that many POC devices cannot offer. The systems, devices, and methods provide many of the quality control features as would be expected in a laboratory setting.

In an embodiment, a sample is diluted in a ratio that is satisfactory for both high senstivity and low sensitivity assays. For example, a dilution ratio of sample to diluent can be in the range of about 1:10,000-1:1. The device can enable a sample to be diluted into separate locations or extents. The device can also enable the sample to be subject to serial dilutions. In further instances, serial dilution within the device or system can dilute the sample up to 10,000,000,000:1.

In embodiments, a sample containing an analyte for detection can be moved from a first location to a second location by aspiration-, syringe-, or pipette-type action. The sample can be drawn into the reaction tip by capillary action or reduced atmospheric pressure. In some embodiments, the sample is moved to many locations, including an array of assay units of a device of the invention and different wells in the housing of a device of the invention. The process of moving the sample can be automated by a system of the invention, as described herein.

The assay units and/or collection tips containing the sample can also be moved from a first location to a second location. The process of moving an assay unit or a collection tip can be automated and carried out by a user-defined protocol.

In an embodiment, the assay units are moved to collect reagent from a reagent unit of the invention. In many embodiments, movement of an assay unit is automated. Aspiration-, syringe-, or pipette-type action can be used to collect reagent from a reagent unit into an assay unit.

Once a sample has been added to an assay unit that comprises a capture surface, the entire unit can be incubated for a period of time to allow for a reaction between the sample and the capture surface of the assay unit. The amount of time needed to incubate the reaction is often dependent on the type of assay being run. The process can be automated by a system of the invention. In an embodiment, the incubation time is between 30 seconds and 60 minutes. In another embodiment, the incubation time is 10 minutes.

An assay unit can also be incubated at an elevated temperature. In an embodiment, the assay unit is incubated at temperature in a range of about 20 to 70 degrees Celsius. The assay unit can be inserted into a heating block to elevate the temperature of the assay unit and/or the contents of the assay unit.

In an embodiment of a method of the invention, a conjugate is added to the assay unit after a sample has been added to the unit. The conjugate can contain a molecule for labeling an analyte captured by a capture surface in the assay unit. Examples of conjugates and capture surface are described hereinafter. The conjugate can be a reagent contained within a reagent unit. The conjugate can be distributed to the assay unit by aspiration-, syringe-, or pipette-type action. Once a conjugate has been distributed to an assay unit, the assay unit can be incubated to allow the conjugate to react with an analyte within the assay unit. The incubation time can be determined by the type of assay or the analyte to be detected. The incubation temperature can be any temperature appropriate for the reaction.

In an aspect, a method of calibrating a device for automated detection of an analyte in a bodily fluid sample is provided. A device can comprise an array of addressable assay units configured to run a chemical reaction that yields a detectable signal indicative of the presence or absence of the analyte, and an array of addressable reagent units, each of which is addressed to correspond to one or more addressable assay units in said device, such that individual reagent units are calibrated in reference to the corresponding assay unit(s) before the arrays are assembled on the device. The device is calibrated by calibrating the assay units and reagent units before they are assembled on the device. The device can then be assembled using the calibrated components, making the device, and a method and system that utilize the device, modular components.

Calibration can be pre-established by measuring the performance of assay reagents, such as conjugates, before the assay units and reagent unit are assembled in a device of the invention. Calibration information and algorithms can be stored on a server linked wirelessly to the assay system. Calibration can be performed in advance or retrospectively by assays performed in replicate systems at a separate location or by using information obtained when the assay system is used.

In an aspect, a control material can be used in a device or system to measure or verify the extent of dilution of a bodily fluid sample. For example, another issue of solid-phase based assays such as ELISA is that an assay uses a solid-phase reagent that is difficult to quality control without destruction of its function. The systems and methods herein provide methods to determine the dilution achieved in a POC system using a disposable device with automated mixing and/or dilution.

In an embodiment, a method provides retrospective analysis, for example, by use of a server in real time to analyze data prior to reporting results. For example, an assay can be performed and a control assay can be run in parallel to the assay. The control assay provides a measurement of an expected dilution of the sample. In some examples, the control assay can verify the dilution of the sample and thus, dilution of a sample for the assay or plurality of assays run within the system can be considered accurate.

A method of measuring a volume of a liquid sample can comprise: reacting a known quantity of a control analyte in a liquid sample with a reagent to yield a detectable signal indicative of the control analyte; and comparing an intensity of said detectable signal with an expected intensity of said detectable signal, wherein the expected intensity of said signal is indicative of an expected volume of the liquid sample, and wherein said comparison provides a measurement of said volume of said liquid sample being measured. In many instances, the control analyte is not present in said liquid sample in a detectable amount.

In an embodiment, a method can further comprise verifying the volume of said liquid sample when the measurement of the volume of the sample is within about 50% of the expected volume of the liquid sample.

For example, a method utilized a device or system described herein can further comprise: reacting a bodily fluid sample containing a target analyte with a reagent to yield a detectable signal indicative of the target analyte; and measuring the quantity of the target analyte in the bodily fluid sample using an intensity of said detectable signal indicative of the target analyte and the measurement of said volume of said liquid sample. The liquid sample and the bodily fluid sample can be the same sample. In some embodiments, the control analyte does not react with the target analyte in the bodily fluid sample, therefore providing not interacting with detection of the target analyte.

In some instances, the liquid sample and the bodily fluid sample are different liquid samples. For example, a control liquid, such as water, and a blood sample. Or in another example, a saliva sample and a blood sample.

A control analyte can be, without limitation, fluorescein-labeled albumin, fluorescein labeled IgG, anti-fluorescein, anti-digoxigenin, digoxigenin-labeled albumin, digoxigenin-labeled IgG, biotinylated proteins, non-human IgG. Other exemplary control analytes can be obvious to one skilled in the art. In an embodiment, the control analyte does not occur in a human bodily fluid sample.

In a POC system as described herein configured to detect a plurality of analytes within a sample, the system can have capabilities to dilute and mix liquids. In many instances, an automated system or user can use a control assay to measure the dilution actually achieved and factor that dilution into the system calibration. For example, a control analyte can be never found in the sample of interest and dried into a reagent unit. The quantity of the dried control analyte can be known and mixed with a sample in the reagent unit. The concentration of analyte can be measured to indicate the volume of sample and any dilution performed on the sample.

Examples of control analytes for an immunoassay include, but are not limited to: fluorescein-labeled protein, biotinylated protein, fluorescein-labeled, Axlexa™-labeled, Rhodamine-labeled, Texas Red-labeled, immunoglobulin. For example the labeling can be achieved by having at least two haptens linked per molecule of protein. In some embodiments, 1-20 haptens are linked per molecule of protein. In a further embodiment, 4-10 haptens are linked per molecule of protein. Many proteins have large numbers of free amino groups to which the haptens can be attached. In many instances, hapten-modified proteins are stable and soluble. Also, haptens such as fluorescein and Texas Red are sufficiently large and rigid that antibodies with high affinity can be made (for example, a hapten is large enough to fill the antibody binding site). In some embodiments, haptens can be attached to proteins using reagents, such as fluorescein isothocyanate, and fluorescein carboxylic acid NHS ester to create control analytes in which the part recognized by the assay system is the hapten.

In some embodiments, a method utilizes dried control analyte. In some examples, a dried control analyte avoids dilution of the sample and can make the control analyte more stable. Dried control analyte can be formulated so it dissolves rapidly and/or completely on exposure to a liquid sample. In some embodiments, a control analyte can be an analyte for which antibodies with high affinity. In some instances, a control analyte can be an analyte that has no cross reaction with any endogenous sample component. Additionally, for example, the analyte can be inexpensive and/or easy to make. In some embodiments, the control analyte is stable over the lifetime of the device or system described herein. Exemplary carriers used to create analytes with covalently linked haptens include proteins such as, but not limited to: albumin, IgG, and casein. Exemplary polymer carriers used to create novel analytes with covalently linked haptens include, but are not limited to: Dextran, Poly-vinylpyrolidone. Exemplary excipients used to formulate and stabilize control analytes include, but are not limited to: sucrose, salts, and buffers (such as sodium phosphate and tris chloride).

A control analyte and method as described herein can be used in a variety of ways including the examples described herein. For example, a method can measure a volume of a sample. In some embodiments, a method measures dilution or a dilution factor or a degree of dilution of a sample. In some instances, a method provides a concentration of the control analyte in a sample. In a system or device described herein to detect a plurality of analytes, measurements from a method herein using a control analyte can be used to verify or describe measurements of target analytes. For example, a fluid transfer device with multiple heads may be used to distribute liquid into a plurality of assay units, including a control unit. In some instances, it can be assumed that liquid amount distributed into the plurality of units is the same or similar between the individual units. In some embodiments, a method described herein with a control analyte can be used to verify that the correct volume of sample has been collected or utilized within a device or system. In another embodiment, a method verifies the correct volume of diluent has been provided to the sample. Also, the dilution factor or degree of dilution can also be verified. In yet another embodiment, a method with a control analyte verifies the correct volume of diluted sample has been distributed to the plurality of units.

Figure 10:
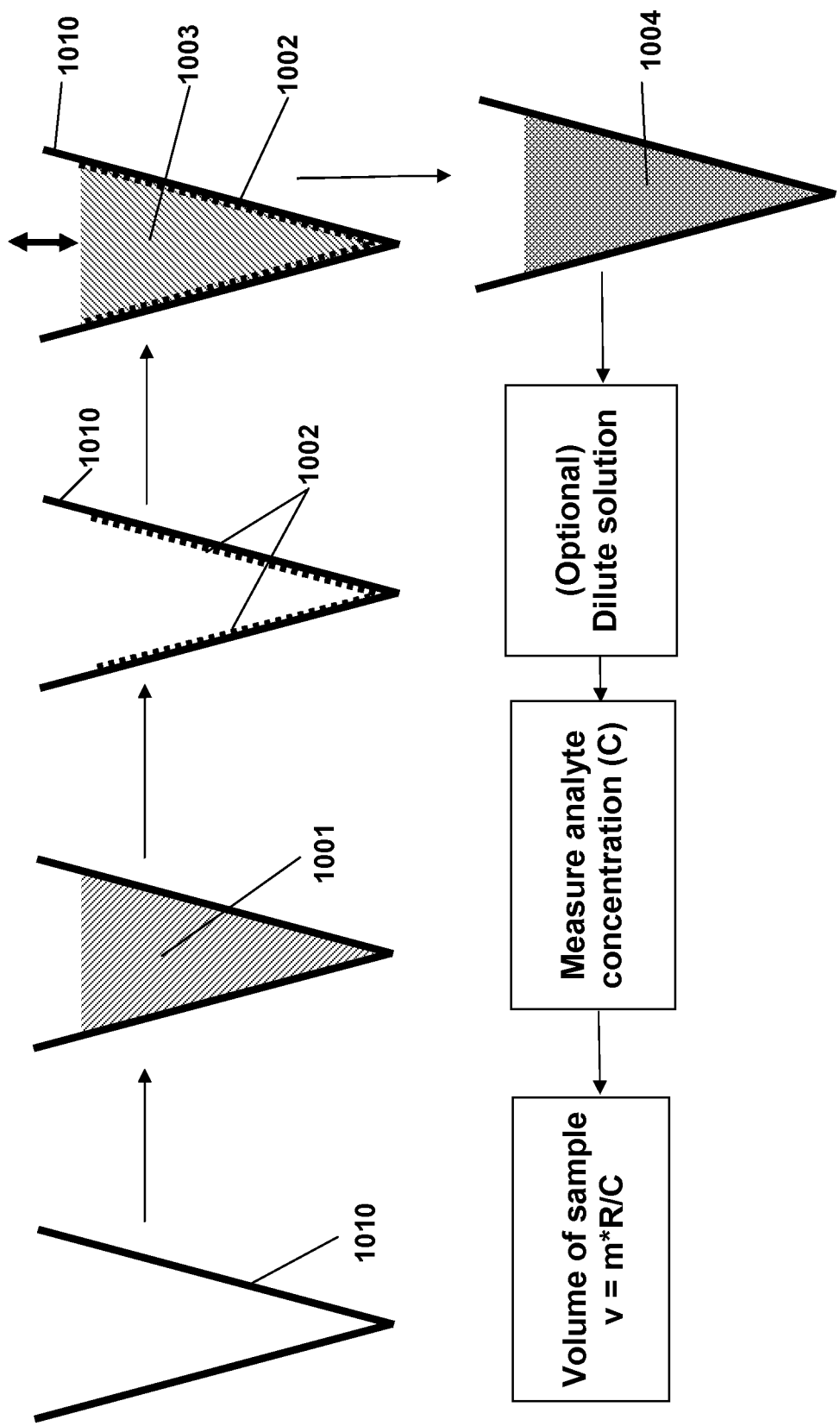
FIG. 10 demonstrates an exemplary method of a control assay as described herein comprising a known quantity of control analyte.

FIG. 10 demonstrates an exemplary method of a control assay as described herein comprising a known quantity of control analyte. A unit 1010 before assembly into a cartridge can be filled with a solution 1001 comprising a known mass of control analyte 1002. The liquid of the solution can be removed and the unit 1010 dried to leave the control analyte 1002 in the unit 1010. The unit 1010 can then be inserted into a device and transported for use. When the unit 1010 is used and receives a sample or diluent 1003, the sample 1003 can be delivered in an expected volume and mixed with the dried control analyte 1002 within the unit 1010 to create a control solution 1004 with an expected concentration. The control solution 1004 can be optionally diluted. In an embodiment, the control analyte 1002 can be detected by the same manners as a target analyte in the device. The control analyte concentration in the control solution 1004 is measured. The measurement of the concentration can be used to calculate the volume of the sample 1003 added to create the control solution 1004. In this manner, a user can compare the measured volume of the sample 1003 with the expected volume of the sample 1003.

In an example, red blood cells can be removed from a blood sample. However, if some red blood cells remain, or red blood cells are not removed from a blood sample, a method with a control analyte can be used to correct for effects from red blood cells in the blood sample. Because hematocrit can vary significantly (for example, from 20-60% of the total volume of a sample), the quantity of an analyte in a fixed or expected volume (v) of blood can be a function of the hematocrit (H expressed here as a decimal fraction). For example, the quantity of analyte with a concentration C in plasma is $C*v*(1-H)$. Thus the quantity for a sample with hematocrit 0.3 is 1.4 times that for a sample with hematocrit 0.5. In an exemplary embodiment, undiluted blood can be dispensed into a device as described and red cells can be removed. A control analyte concentration in the plasma fraction can then be measured to estimate the volume of sample plasma and determine the hematocrit.

In some embodiments, unbound conjugate may need to be washed from a reaction site to prevent unbound conjugates from producing inaccurate detection. The limiting step of many immunoassays is a washing step. The compromise of minimum carryover and high sensitivity is dependent on the wash removal of unbound conjugate. The wash step can be severely limited in a microtiter plate format due to the difficulty of removing the wash liquid from a well (for example, by automatic means). An assay unit device and system of the invention can have a number of advantages in the way liquids are handled. An advantage may be an improvement in the signal to noise ratio of an assay.

Removal of the conjugate can be difficult to if conjugates are sticking to the edges of the assay units of a device if, for example, there is not an excess of a wash solution.

A wash of the conjugate can occur by either pushing the wash solution from above or drawing the wash solution up and expelling the liquid similar to the loading of the sample. The washing can be repeated as many times as necessary.

When using a wash buffer in an assay, the device can store the wash buffer in reagent units and the assay unit can be brought into fluid communication with the wash. In an embodiment, the wash reagent is able to remove unbound reagent from the assay units by about 99, 99.9, or 99.999% by washing. In general, a high washing efficiency resulting in a high degree of reduction of undesired background signals is preferred. Washing efficiency is typically defined by the ratio of signal from a given assay to the total amount of signal generated by an assay with no wash step and can be readily determined by routine experimentation. It can be generally preferred to increase the volume of washing solution and time of incubation but without sacrificing the signals from a given assay. In some embodiments, washing is performed with about 50 ul to about 5000 ul of washing buffer, preferably between about 50 ul to about 500 ul washing buffer, for about 10 to about 300 seconds.

Additionally, it can be advantageous to use several cycles of small volumes of wash solution which are separated by periods of time where no wash solution is used. This sequence allows for diffusive washing, where labeled antibodies diffuse over time into the bulk wash solution from protected parts of the assay unit such as the edges or surfaces where it is loosely bound and can then be removed when the wash solution is moved from the reaction site.

In many embodiments, the last step is to distribute an enzymatic substrate to detect the conjugate by optical or electrical means. Examples of substrates are described hereinafter.

For example, the reagent in the individual reagent unit of a device herein can be an enzyme substrate for an immunoassay. In another embodiment, the step of transferring the substrate reagent from the individual reagent unit can be repeated after a reaction at the capture site. For example, enzymatic substrate is transferred to a reaction site and incubated. After measuring the assay signal produced, used substrate can be removed and replaced with fresh substrate and the assay signal remeasured. A signal indicative of the individual analyte being can be detected using a system as described herein from both the first and the second application of substrate. The second substrate is usually the same as the original substrate. In an embodiment, the second substrate is transferred to a reaction site from a second reagent unit of a device herein. In another embodiment, the second substrate is transferred to a reaction site from the same reagent unit as the original substrate. Transferring a second substrate thereby creates a second reaction to yield a second signal indicative of the individual analyte. The intensity of the original signal and a second intensity of the second signal can be compared to calculate the final intensity of the signal indicative of the individual analyte and whether the assay was properly conducted.

In an embodiment, the intensities of the multiple signals can be used for quality control of an assay. For example, if the signals differ by 20%, 30%, 40%, 50%, 60%, 70%, 80%, 90%, 100% or more, the assay results may be disregarded.

In an embodiment, a method as described herein comprises re-loading sample and or detector-conjugate (enzyme-labeled antibody) and or the enzyme substrate and sample to rectify or confirm an assay signal or to use as an internal control. For example, re-use of an assay tip or unit as described can be provided to verify function and/or to add further sample or control materials obtain a second signal.

In some instances, a method of re-loading a substrate to an enzyme unit is enabled by the ability of a system as described herein to automatically to transfer liquid samples and reagents into the assay units. Some assays do not require the system to deliver a result immediately or on a schedule, therefore, a control method as described offers an opportunity to possibly enhance the reliability of the results. A response observed following iterations of adding an enzyme substrate can be used to verify the initial response or to calculate spike recovery.

Experiments have shown that by adding a second enzyme substrate to an assay unit, the reproducibility of results can be maintained. In some embodiments, a control method provides replicate analyses using an assay unit gave a response significantly lower than that expected.

With any control methods described herein, there are numerous possible errors that can be accounted for or postulated from executing a control method. Exemplary assay errors include, but are not limited to, improper manufacturing of an assay unit or device, improper aspiration of a sample and/or one or more reagents, an assay unit is not positioned properly relative to the photomultiplier during detection, and a missing assay unit in the device or system.

In some embodiments, the present invention provides a method of obtaining pharmacological data useful for assessing efficacy and/or toxicity of a pharmaceutical agent from a test animal utilizing the subject fluidic devices or systems.

When using laboratory animals in preclinical testing of a pharmaceutical agent, it is often necessary to kill the test subject to extract enough blood to perform an assay to detect an analyte of interest. This has both financial and ethical implications, and as such it may be advantageous to be able to draw an amount of blood from a test animal such that the animal does not need to be killed. In addition, this can also allow the same test animal to be tested over several different time points, thus allowing for a more effective evaluation of the effects of an agent on single animals. On average, the total blood volume in a mouse, for example, is 6-8 mL of blood per 100 gram of body weight. A benefit of the current invention is that only a very small volume of blood is required to perform preclinical trials on mice or other small laboratory animals. In some embodiments between about 1 microliter and about 50 microliters are drawn. In an embodiment between about 1 microliter and 10 microliters are drawn. In preferred embodiments about 5 microliters of blood are drawn.

A further advantage of keeping the test animal alive is evident in a preclinical time course study. When multiple mice, for example, are used to monitor the levels of an analyte in a test subject's bodily fluid over time, the added variable of using multiple subjects is introduced into the trial. When, however, a single test animal can be used as its own control over a course of time, a more accurate and beneficial preclinical trial can be performed.

In some embodiments a method of automatically monitoring patient compliance with a medical treatment using the subject devices or systems is provided. The method comprises the steps of allowing a sample of bodily fluid to react with assay reagents in a device to yield a detectable signal indicative of the presence of an analyte in said sample; detecting said signal with said device; comparing said signal with a known profile associated with said medical treatment to determine if said patient is compliant or noncompliant with said medical treatment; and notifying a patient of said compliance or noncompliance.

In another embodiment, the system and methods of the invention provide a means of discovering new biomarkers and/or validating by association of trends in such markers with disease and therapy outcomes.

In another embodiment, the system and methods of the invention can identify trends in biomarker levels and daily patient diary information over time that can be used to adjust a drug dose to an optimal level for particular patients (for example, adaptive dose-ranging).

In some embodiments noncompliance may include taking an improper dose of a pharmaceutical agent including without limitation multiple doses or no dose, or may include inappropriately mixing pharmaceutical agents. In preferred embodiments a patient is notified substantially immediately after the signal is compared with a known profile.

A patient or subject of a clinical trial may forget to take a bodily fluid sample for analysis as described herein. In some embodiments a method of alerting a patient to test a sample of bodily fluid using a device as described herein comprises providing a protocol to be run on said device, said protocol located on an external device, associated with said patient, and comprising a time and date to test said sample of bodily fluid; and notifying patient to test said bodily fluid on said date and time if said sample has not been tested. In some embodiments a patient can be notified wirelessly as described herein. Compliance with therapeutic regimes can be improved by use of prompts on a display and obtaining responses from patients (for example, by way of a touchscreen).

A patient may be provided with a device when procuring a prescription of drugs by any common methods, for example, at a pharmacy. Likewise, a clinical trial subject may be provided with such devices when starting a clinical trial. The patient or subject's contact information, including without limitation cell phone, email address, text messaging address, or other means of wireless communication, may at that time be entered into the external device and associated with the patient or subject as described herein, for example, in a database. Software on the external device may include a script or other program that can detect when a signal generated from a detection device has not yet been sent to the external device, for example at a given time, and the external device can then send an alert notifying the patient to take a bodily fluid sample.

In one embodiment, the system is provided directly to a consumer and is used in lifestyle and/or athletic management. Relevant lifestyle and exercise data can be input and measurements of parameters indicative of muscle damage, anaerobic metabolism (for example, lactic acid) can be measured. In some embodiments, the system can be sufficiently small to be portable.

In another embodiment, the system is particularly suited for measurement of markers in the blood of small animals such as rats and mice that are commonly used in pre-clinical work. Such animals only have a small volume of blood and so assay systems requiring very small volumes of sample are particularly useful, especially in longitudinal studies where several samples from a single animal are needed in rapid succession. These considerations can be especially important when several analytes need to be measured in parallel.

In one embodiment, the system includes a convenient way to package the several elements required for multiple complex assays in a secure form for shipping. For example, assay elements click fit into a housing.

Assays

A variety of assays may be performed on a fluidic device according to the present invention to detect an analyte of interest in a sample. A wide diversity of labels is available in the art that can be employed for conducting the subject assays. In some embodiments labels are detectable by spectroscopic, photochemical, biochemical, electrochemical, immunochemical, or other chemical means. For example, useful nucleic acid labels include the radioisotopes $32P$, $35S$, fluorescent dyes, electron-dense reagents, enzymes. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, bioluminescent labels, or colorimetric labels. Reagents defining assay specificity optionally include, for example, monoclonal antibodies, polyclonal antibodies, proteins, nucleic acid probes or other polymers such as affinity matrices, carbohydrates or lipids. Detection can proceed by any of a variety of known methods, including spectrophotometric or optical tracking of radioactive, fluorescent, or luminescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Thus, a label includes without limitation any composition detectable by spectroscopic, photochemical, biochemical, immunochemical, nucleic acid probe-based, electrical, optical thermal, or other chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non-radioactive labels are often attached by indirect means. Generally, a receptor specific to the analyte is linked to a signal generating moiety. Sometimes the analyte receptor is linked to an adaptor molecule (such as biotin or avidin) and the assay reagent set includes a binding moiety (such as a biotinylated reagent or avidin) that binds to the adaptor and to the analyte. The analyte binds to a specific receptor on the reaction site. A labeled reagent can form a sandwich complex in which the analyte is in the center. The reagent can also compete with the analyte for receptors on the reaction site or bind to vacant receptors on the reaction site not occupied by analyte. The label is either inherently detectable or bound to a signal system, such as a detectable enzyme, a fluorescent compound, a chemiluminescent compound, or a chemiluminogenic entity such as an enzyme with a luminogenic substrate. A number of ligands and anti-ligands can be used. Where a ligand has a natural anti-ligand, for example, biotin, thyroxine, digoxigenin, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl groups, and umbelliferone. Chemiluminescent compounds include dioxetanes, acridinium esters, luciferin, and 2,3-dihydrophthalazinediones, such as luminol.

Methods of detecting labels are well known to those of skilled in the art. Thus, for example, where the label is radioactive, means for detection include scintillation counting or photographic films as in autoradiography. Where the label is fluorescent, it may be detected by exciting the fluorochrome with light of an appropriate wavelength and detecting the resulting fluorescence by, for example, microscopy, visual inspection, via photographic film, by the use of electronic detectors such as digital cameras, charge coupled devices (CCDs) or photomultipliers and phototubes, or other detection device. Similarly, enzymatic labels are detected by providing appropriate substrates for the enzyme and detecting the resulting reaction product Finally, simple colorimetric labels are often detected simply by observing the color associated with the label. For example, conjugated gold often appears pink, while various conjugated beads appear the color of the bead.

In some embodiments the detectable signal may be provided by luminescence sources. Luminescence is the term commonly used to refer to the emission of light from a substance for any reason other than a rise in its temperature. In general, atoms or molecules emit photons of electromagnetic energy (e.g., light) when then move from an excited state to a lower energy state (usually the ground state). If exciting cause is a photon, the luminescence process is referred to as photoluminescence. If the exciting cause is an electron, the luminescence process can be referred to as electroluminescence. More specifically, electroluminescence results from the direct injection and removal of electrons to form an electron-hole pair, and subsequent recombination of the electron-hole pair to emit a photon. Luminescence which results from a chemical reaction is usually referred to as chemiluminescence. Luminescence produced by a living organism is usually referred to as bioluminescence. If photoluminescence is the result of a spin-allowed transition (e.g., a single-singlet transition, triplet-triplet transition), the photoluminescence process is usually referred to as fluorescence. Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as phosphorescence. Typically, phosphorescence emissions persist long after the exciting cause is removed as a result of long-lived excited states which may relax only through such spin-forbidden transitions. A luminescent label may have any one of the above-described properties.

Suitable chemiluminescent sources include a compound which becomes electronically excited by a chemical reaction and may then emit light which serves as the detectable signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinium esters and dioxetanes. Alternatively, luciferins may be used in conjunction with luciferase or lucigenins to provide bioluminescence.

The term analytes as used herein includes without limitation drugs, prodrugs, pharmaceutical agents, drug metabolites, biomarkers such as expressed proteins and cell markers, antibodies, serum proteins, cholesterol and other metabolites, polysaccharides, nucleic acids, biological analytes, biomarkers, genes, proteins, or hormones, or any combination thereof. Analytes can be combinations of polypeptides, glycoproteins, polysaccharides, lipids, and nucleic acids.

Of particular interest are biomarkers are associated with a particular disease or with a specific disease stage. Such analytes include but are not limited to those associated with autoimmune diseases, obesity, hypertension, diabetes, neuronal and/or muscular degenerative diseases, cardiac diseases, endocrine disorders, metabolic disorders, inflammation, cardiovascular diseases, sepsis, angiogenesis, cancers, Alzheimer's disease, athletic complications, and any combinations thereof.

Of also interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are analytes that are indicative of a microorganism, virus, or Chlamydiaceae. Exemplary microorganisms include but are not limited to bacteria, viruses, fungi and protozoa. Analytes that can be detected by the subject method also include blood-born pathogens selected from a non-limiting group that consists of *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*.

Analytes that can be detected by the subject method also encompass a variety of sexually transmitted diseases selected from the following: gonorrhea (*Neisseria gorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional analytes that can be detected by the subject methods encompass a diversity of respiratory pathogens including but not limited to *Pseudomonas aeruginosa*, methicillin-resistant *Staphlococcccus aureus* (MSRA), *Klebsiella pneumoniae, Haemophilus influenzae, Staphylococcus aureus, Stenotrophomonas maltophilia, Haemophilis parainfluenzae, Escherichia coli, Enterococcus faecalis, Serratia marcescens, Haemophilus parahaemolyticus, Enterococcus cloacae, Candida albicans, Moraxiella* catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae, and Mycobacterium tuberculosis.

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alpha-fetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancrease markers include without limitation Amylase, Pancreatitis-Assocoated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx) Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartillage Oligimeric Matrix Protein), Osteocrin Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease conditions include without limitation: Viremia, Bacteremia, Sepsis, and markers: PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyldipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4) Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, amd sTfR (soluble. Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII, Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibodies include those for EGFR, ErbB2, and IGF1R.

Exemplary tyrosine kinase inhibitors include without limitation Ab1, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threoline Kinas Inhibitors include without limitation AKT, Aurora AB/B, CDK, CDK (pan), CDK1-2, VEGFR2, PDGFRb, CDK4/6, MEK1-2, mTOR, and PKC-beta.

GPCR targets include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

In a separate embodiment, a method of monitoring more than one pharmacological parameter useful for assessing efficacy and/or toxicity of a therapeutic agent is provided. For example, a therapeutic agent can include any substances that have therapeutic utility and/or potential Such substances include but are not limited to biological or chemical compounds such as simple or complex organic or inorganic molecules, peptides, proteins (e.g. antibodies) or a polynucleotides (e.g. anti-sense). A vast array of compounds can be synthesized, for example polymers, such as polypeptides and polynucleotides, and synthetic organic compounds based on various core structures, and these can also be included as therapeutic agents. In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. For example, small molecule drugs are often measured by mass-spectrometry which can be imprecise. ELISA (antibody-based) assays can be much more accurate and precise.

Physiological parameters according to the present invention include without limitation parameters such as temperature, heart rate/pulse, blood pressure, and respiratory rate. Pharmacodynamic parameters include concentrations of biomarkers such as proteins, nucleic acids, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the pharmacodynamic (PD) parameters fall outside the desired range during a treatment regime, immediate action may have to be taken as well.

Being able to monitor the rate of change of an analyte concentration or PD or PK parameters over a period of time in a single subject, or performing trend analysis on the concentration, PD, or PK parameters, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

In some embodiments, the present invention provides a business method of assisting a clinician in providing an individualized medical treatment. A business method can comprise post prescription monitoring of drug therapy by monitoring trends in biomarkers over time. The business method can comprise collecting at least one pharmacological parameter from an individual receiving a medication, said collecting step is effected by subjecting a sample of bodily fluid to reactants contained in a fluidic device, which is provided to said individual to yield a detectable signal indicative of said at least one pharmacological parameter; and cross referencing with the aid of a computer medical records of said individual with the at least one pharmacological parameter of said individual, thereby assisting said clinician in providing individualized medical treatment.

The devices, systems, and methods herein allow for automatic quantification of a pharmacological parameter of a patient as well as automatic comparison of the parameter with, for example, the patient's medical records which may include a history of the monitored parameter, or medical records of another group of subjects. Coupling real-time analyte monitoring with an external device which can store data as well as perform any type of data processing or algorithm, for example, provides a device that can assist with typical patient care which can include, for example, comparing current patient data with past patient data. Therefore, also provided herein is a business method which effectively performs at least part of the monitoring of a patient that is currently performed by medical personnel.

Example 1

In this example, a device, method, and system of the invention are used to perform an assay for human VEGFR2. The example demonstrates a type of assay that can be performed at the point of care. The capture surface of an assay unit can be coated onto the assay unit according to the assay, this example a VEGFR2 assay. The inner surface of the assay unit (made from injection molded polystyrene similar to example in FIG. 3A) was exposed to a succession of coating reagents by aspiration and pneumatic ejection. Twenty microliters of each coating reagents were drawn into assay units and incubated at room temperature for 10 minutes. The coating reagents used in this example are, as used in succession, Neutravidin (20 ug/mL) in Carbonate-Bicarbonate buffer (pH 9), biotinylated "capture antibody" (a monoclonal antibody directed to VEGFR2 at 20 ug/mL) in Tris buffered saline, (pH 8), and a "fixative" reagent containing 3% bovine serum albumin in Tris-buffered saline. After the succession of coatings, the assay units were dried by exposure to dry air and stored desiccated.

Samples for analysis are then distributed to the assay unit diluted in a solution of 50 mM tris-buffer (pH 8) containing bovine serum albumin and isotonic sucrose for 20 minutes. In a reagent unit comprising a conjugate, a solution of Alkaline phosphatase (bovine intestine)-labeled monoclonal antibody directed to VEGFR2 (binding to a distinct epitope to the antibody of the capture surface) at 250 ng/mL in a stabilizer reagent from Biostab is provided to the assay unit for 10 minutes. After the conjugate has been allowed to bind with the complex of the analyte bound to the capture surface, the assay unit was washed with a solution contained in a reagent unit (commercially available wash buffer from Assay Designs). The assay unit was washed 5 times. Then the assay unit was moved to collect and mix with another reagent contained in a different reagent, a solution of a commercially available luminogenic substrate for alkaline phosphatase (KPL Phosphaglo), and incubated for 10 minutes. The reaction of the assay in the assay unit was then detected by a detector assembly of the invention.

Figure 12:
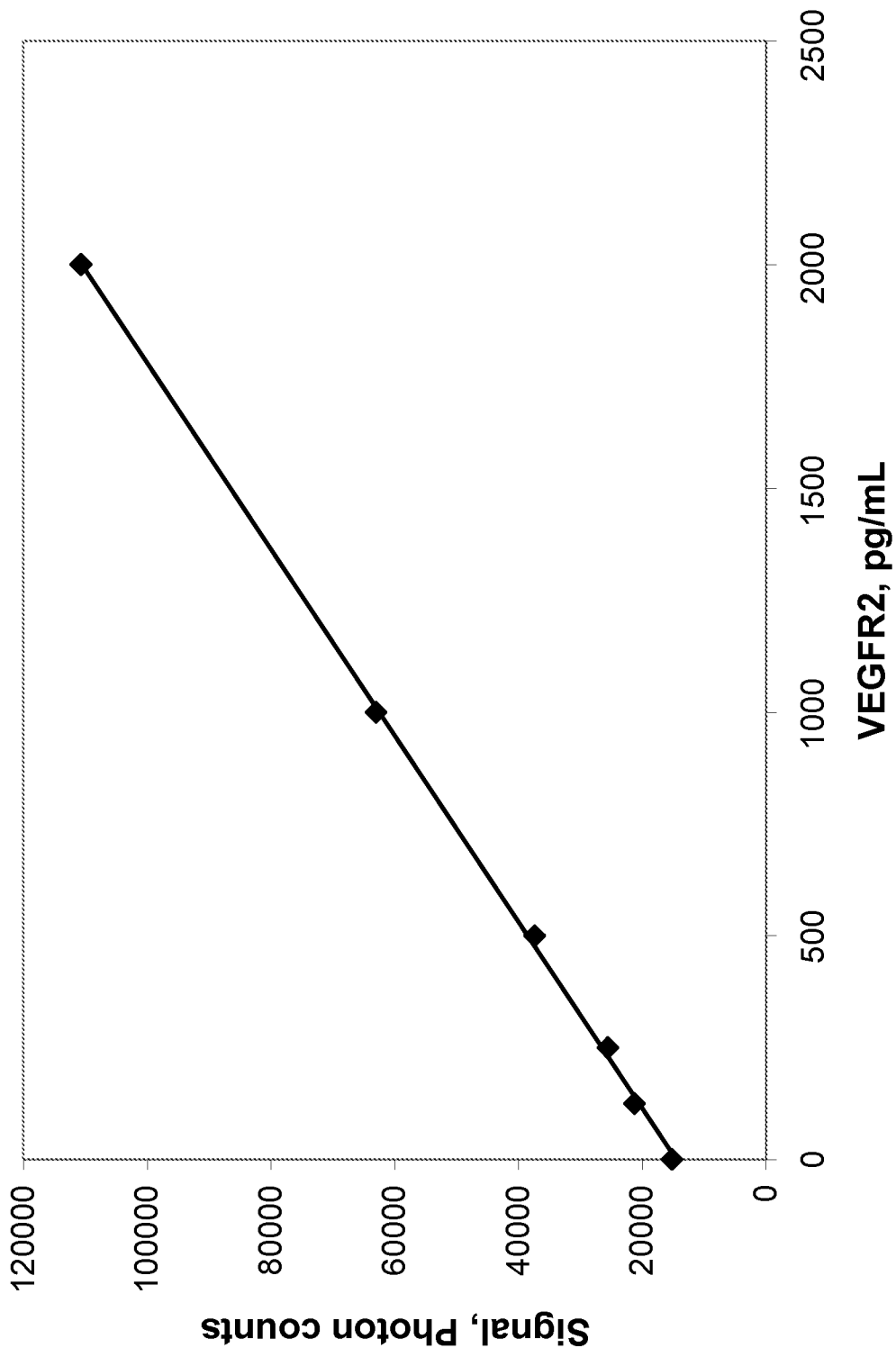
FIG. 12 illustrates a calibration curve correlating an assay unit and a reagent unit for conducting an assay for VEGFR2.

FIG. 12 demonstrates the VEGFR2 assay response using the method of the example. The x axis scale is VEGFR2 concentration (pg/mL); the y scale is relative luminescence (counts). The curve was used to calibrate the modular assay unit and reagent units.

Example 2

Figure 13:
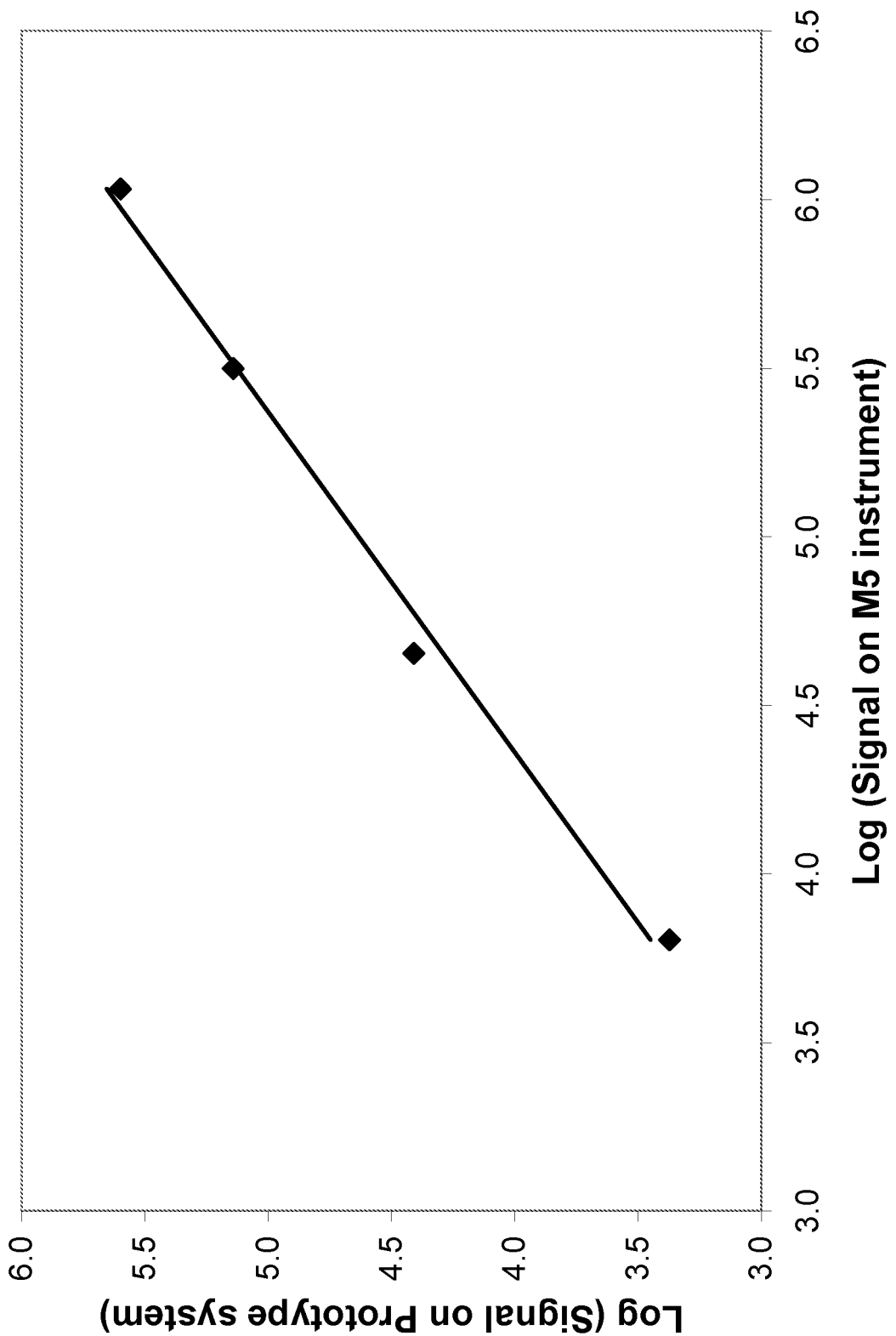
FIG. 13 illustrates a calibration curve correlating results for an assay unit and a reagent unit for conducting an assay for P1GF in a system, as measured with a luminometer.

An assay for human P1GF was performed using the assay units and reagent units of the invention and read in a commercial instrument. In parallel, an assay using the same reagents was done in prototype disposable cartridges (as described below) in a prototype reader. Analyte concentrations were 0, 4, 80 and 400 pg/mL respectively. The measurements illustrated in FIG. 13 were used to calibrate an assay unit and reagent unit necessary for conducting an assay for human P1GF.

Example 3

Magnetizable beads are 1.3 um diameter BioMag magnetic particles from Bangs Laboratories. Beads are coated (by the manufacturer) with anti-Rabbit IgG. Beads are dispersed at 14 mg/mL in tris-buffered sucrose (or, alternatively, tris buffered saline) containing 3% bovine serum albumin and rabbit anti-human red blood cell IgG, from CedarLane at >=1.15 mg/mL. Aliquots (10 uL of this dispersion were dispensed into conical tubes and lyophilized (frozen in liquid N2 and lyophilized for approximately 24 hrs. at −70 C) prior to insertion into a slot in the cartridge housing. The rabbit antibody binds both to the red cells and to the anti-rabbit IgG-coated beads and forms a co-agglutinate of beads and red cells.

The lyophilized magnetizable bead pellet was re-suspended by adding 20 uL of whole blood then aspirating and dispensing at least 8 times (approximately 1.5 min) into a conical tube.

Blood was separated by placing the tip (in a vertical orientation) in a strong, horizontally oriented magnetic field. Typically 8 uL of essentially red cell free plasma with no observable hemolysis was recovered from a 20 ul blood sample (70% yield). Recovery of analytes (compared to plasma not exposed to the magnetic separation) was close to 100% for Protein-C, VEGF, P1GF, Insulin, GIP and GIP-1.

Example 4

Serial dilution of a sample for analyses of an analyte can be carried out in a system as described herein. C-reactive protein (CRP) is an acute-phase marker. Normal levels are in the high ng/mL to low ug/ml range. In any acute disease process, the human liver produces CRP and levels in blood can increase to hundreds of ug/ml. CRP has presented issues for prior art POC analytic systems because of the wide dynamic range of analyte to be measured ($>10^5$-fold).

A system as described herein comprising a fluid transfer device and a cartridge or device with arrays of assay and reagent units was developed. Assay tips having monoclonal anti-CRP bound to their inner surface were mounted in cartridge together with a detector-antibody solution (alkaline phosphatase labeled monoclonal anti-CRP (having a different epitope specificity than that on the tips), a wash solution and a chemiluminogenic alkaline phosphatase (PhosphaGLO™) substrate from KPL.

Figure 14:
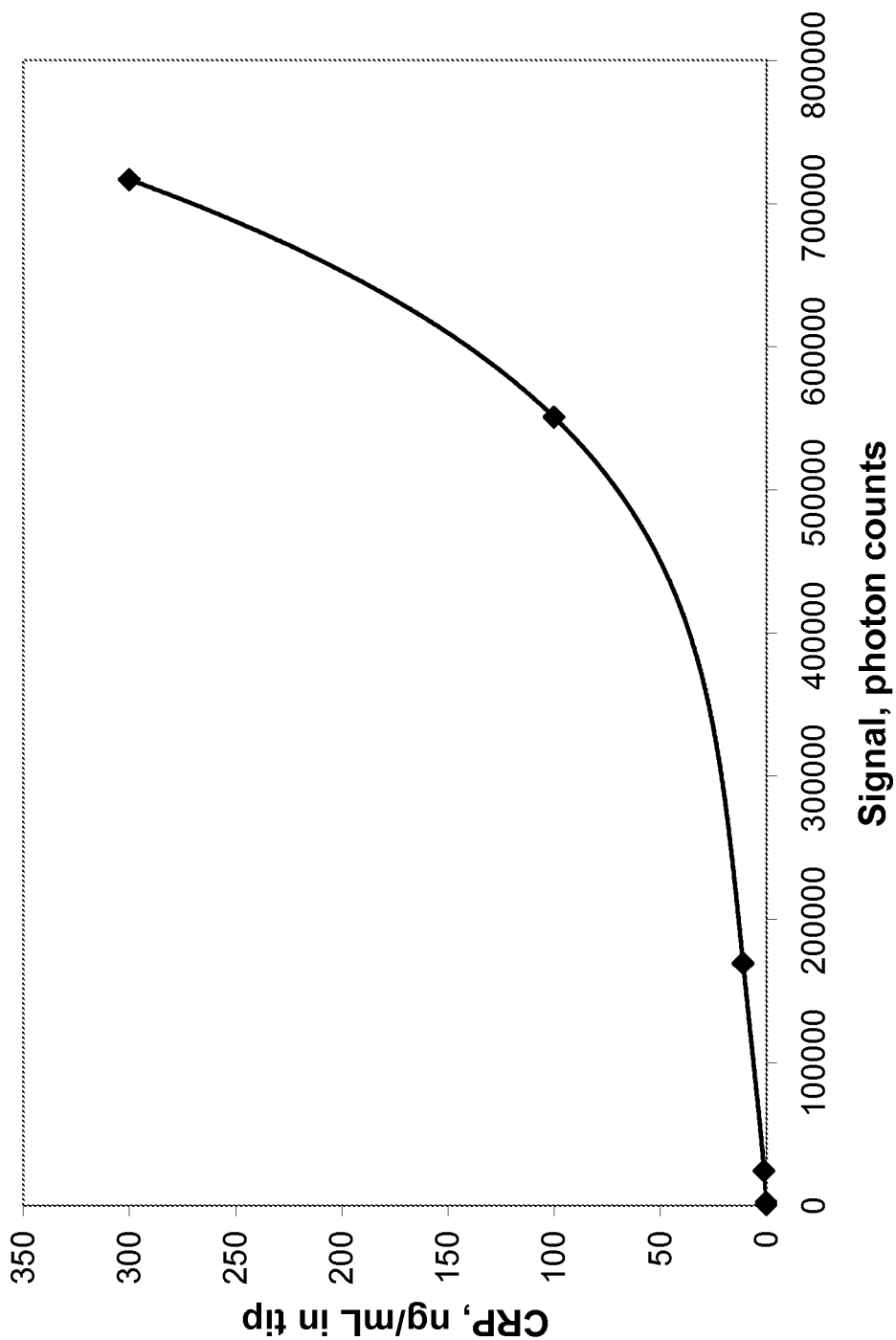
FIG. 14 illustrates CRP concentration plotted against the assay signal (photon counts) and the data fitted to a 5-term polynomial function to generate a calibration function.

To assay CRP, the cartridges were loaded with pre-diluted solutions of CRP used without further dilution. The cartridges were processed by a system. Successively the CRP solution (10 uL), detector antibody (12 uL) were drawn into the tips incubated for 10 min at 34° C. then discarded. The tips were washed by four aspirations of 20 uL wash solution before 15 uL of substrate was aspirated into the tips. After 10 min at 37° C., light emission was measured by the instrument for 5 s. CRP concentration was plotted against the assay signal (photon counts) and the data fitted to a 5-term polynomial function as shown below to generate a calibration function as shown in FIG. 14.

Example 5

An experiment was then executed using serial dilutions of a sample containing highly concentrated analyte to obtain an unambiguous assay response in a system and device as described herein. Solutions of CRP (20 uL) were loaded into cartridges and serially diluted by the instrument (to dilutions of 1:50, 250, 750 and 1500-fold respectively). The diluted solutions were then processed as in Example 4. When the diluted CRP concentration exceeded the calibration range of the assay (300 ng/mL), a downward response was seen (as shown below; data from two instruments).

Figure 15:
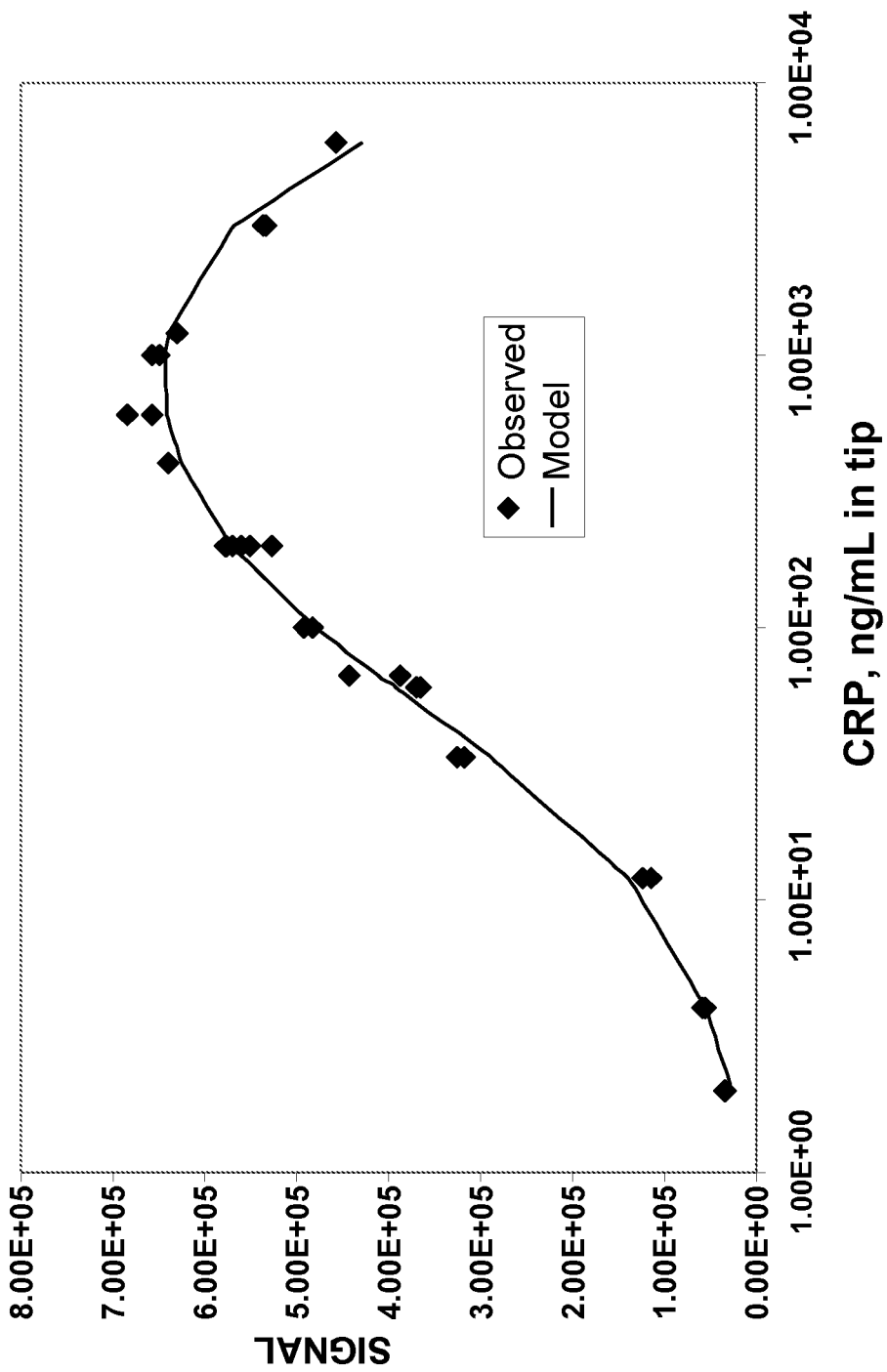
FIG. 15 shows a fit was achieved between a model and the values of the parameters Smax, C0.5 and D as described herein.

The response as shown in FIG. 15 can be modeled using a modification of the Scatchard binding isotherm ($S/S_{max}=C/(C+C0.5)$). The modification assumes that the response of the assay is linearly proportional to the concentration of the detector antibody, as is the case in this example (data not shown). Any carry-over of CRP in the diluted sample into the next reagent (detector antibody) will react rapidly with the reagent rendering it incapable of binding to antigen bound to the solid phase antibody. The reduction in effective concentration is reduced in proportion to the CRP carried-over and can be accounted for with a factor $(D-C*f)/D$.

Therefore, $S=S_{max}*(C/(C+C0.5))*(D-C*f)/D$, wherein S is the assay signal, Smax is the maximum signal (corresponding to zero carry-over), C is the concentration of analyte, C0.5 is the concentration for half-maximal signal (no carry-over), D is the detector antibody concentration, and f is the fractional carryover.

Values used to fit the data, were derived by optimizing each of the four parameters below using the technique of minimization of least square differences between the data and the model fit. As can be seen in FIG. 15, an excellent fit was achieved and the values of the parameters Smax, C0.5 and D (see table 2) are close to the values that can be estimated from the maximum signal reached, the observed C0.5 and the known detector antibody concentration. This model estimated the extent of carry-over as 0.034% (decimal 3.83E-04).

TABLE 1

Best fit parameters to model describing biphasic CRP assay response

| Parameter | Value | Units |
| --- | --- | --- |
| Smax | 7.24E+05 | Counts |
| C0.5 | 5.02E+01 | ng/mL |
| D | 5.72E+00 | ng/mL |
| f | 3.83E-04 | |

Figure 16:
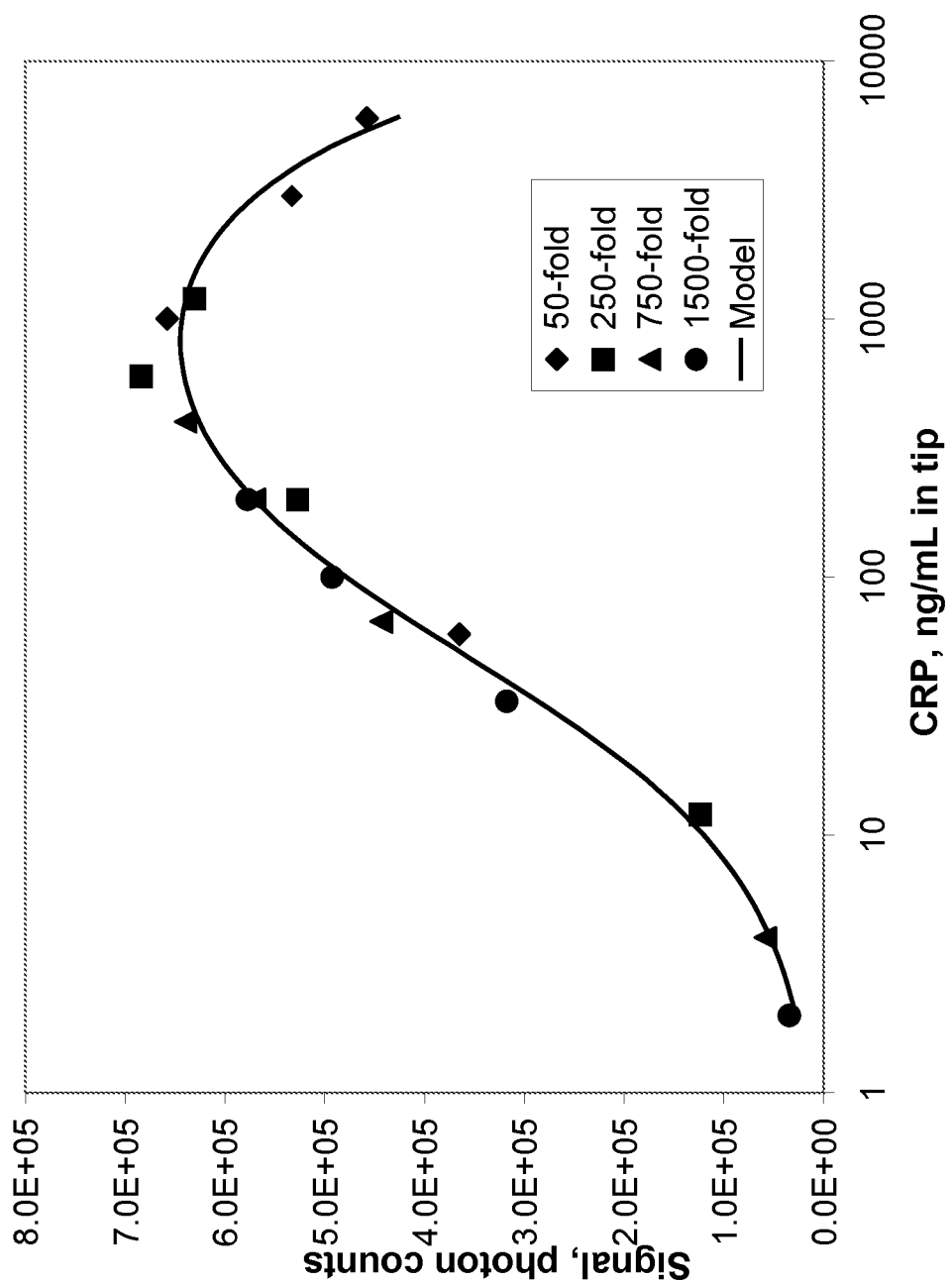
FIG. 16 displays data according to the dilution used to achieve the final concentration in an assay tip.

Data can be then be viewed according to the dilution used to achieve the final concentration in each assay tip, and for each dilution level the responses fit to the same response showing that the dilutions are accurate and precise as shown in FIG. 16.

Figure 17:
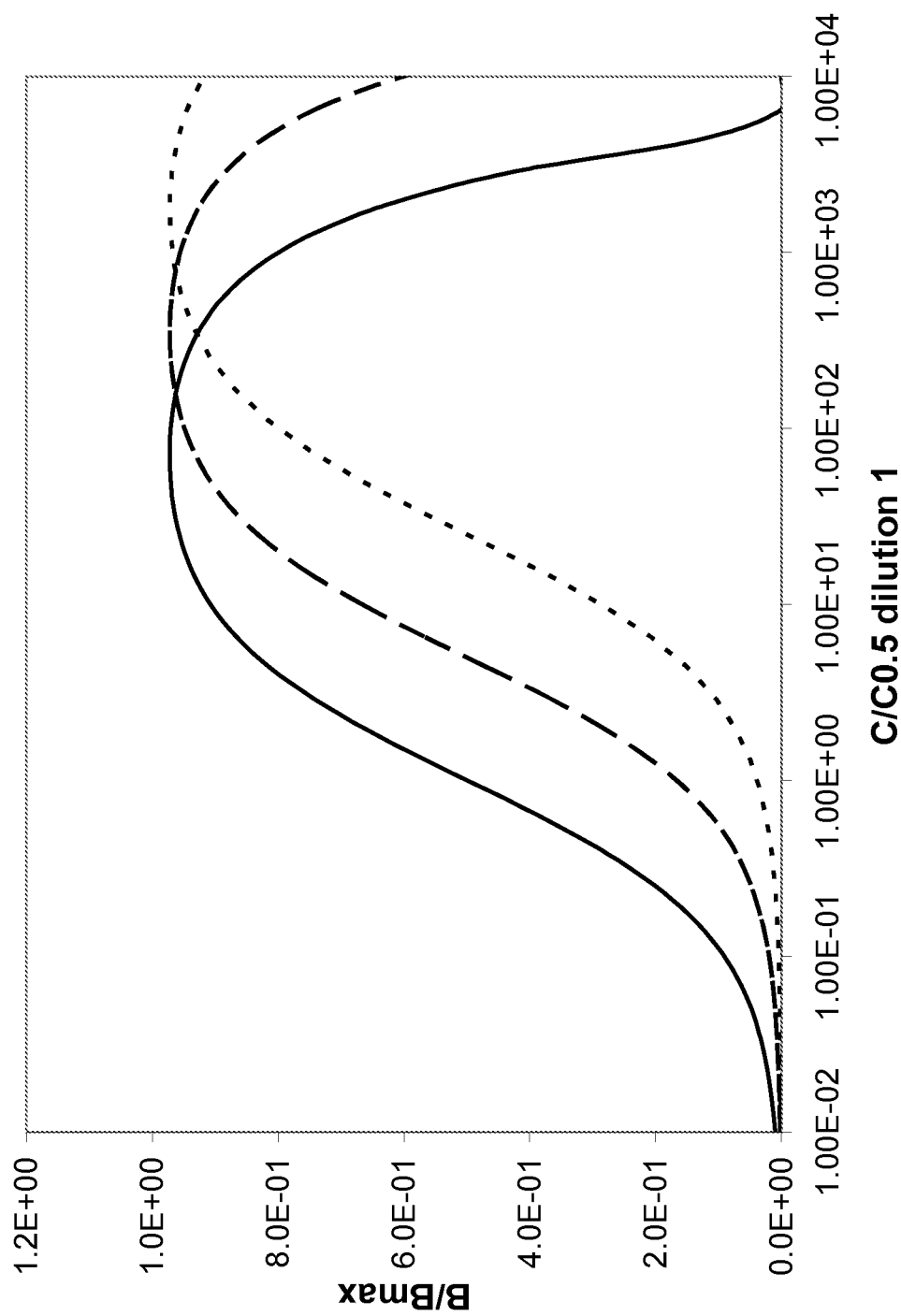
FIG. 17 illustrates the normalized assay response (B/Bmax) is plotted against the log normalized concentration (C/C0.5) for relative dilutions: 1:1 (solid line), 5:1 (dashed line), and 25:1 (dotted line).
Figure 18:
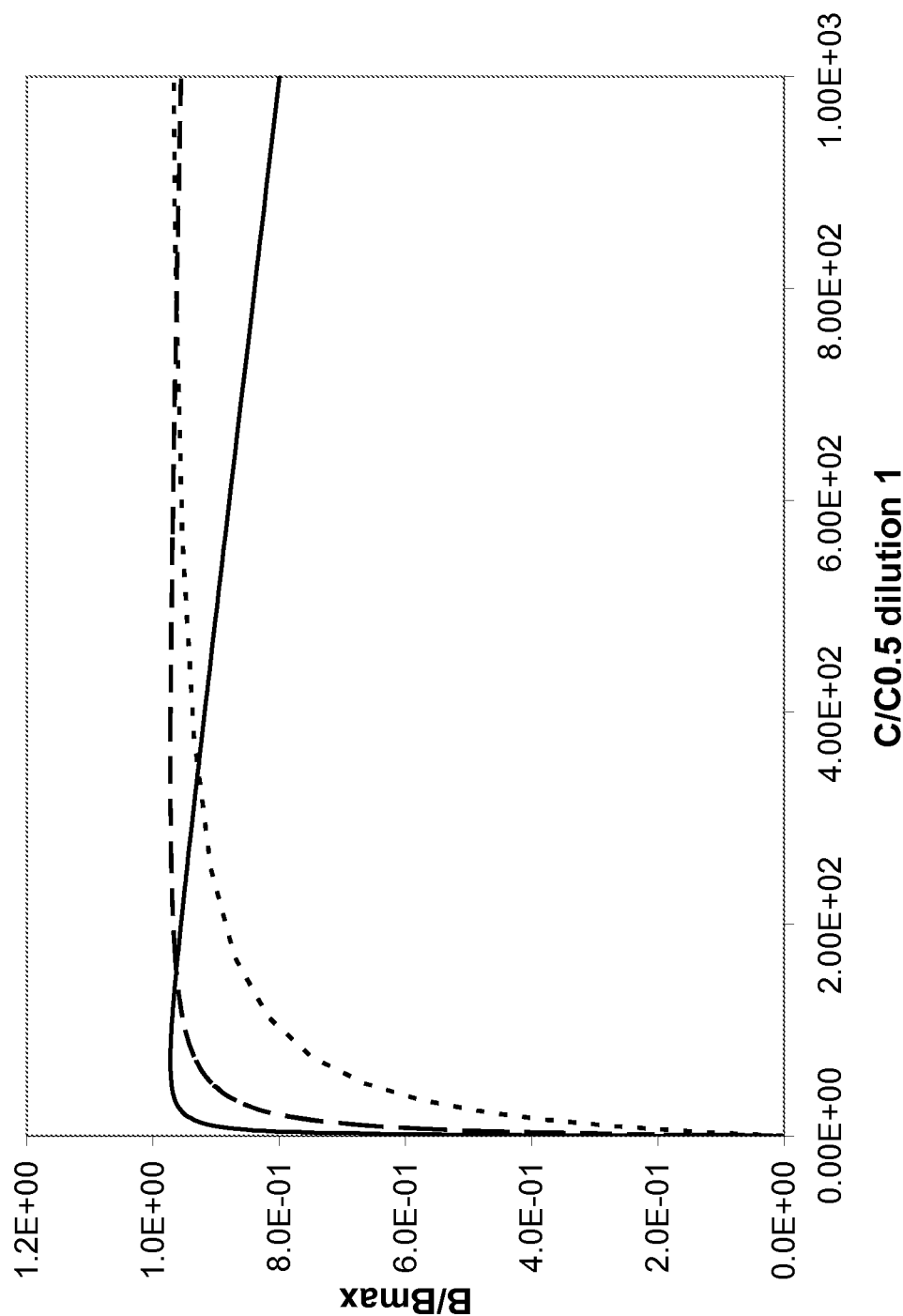
FIGS. 18 and 19 illustrate a similar example as FIG. 17 at different normalized concentrations.
Figure 19:
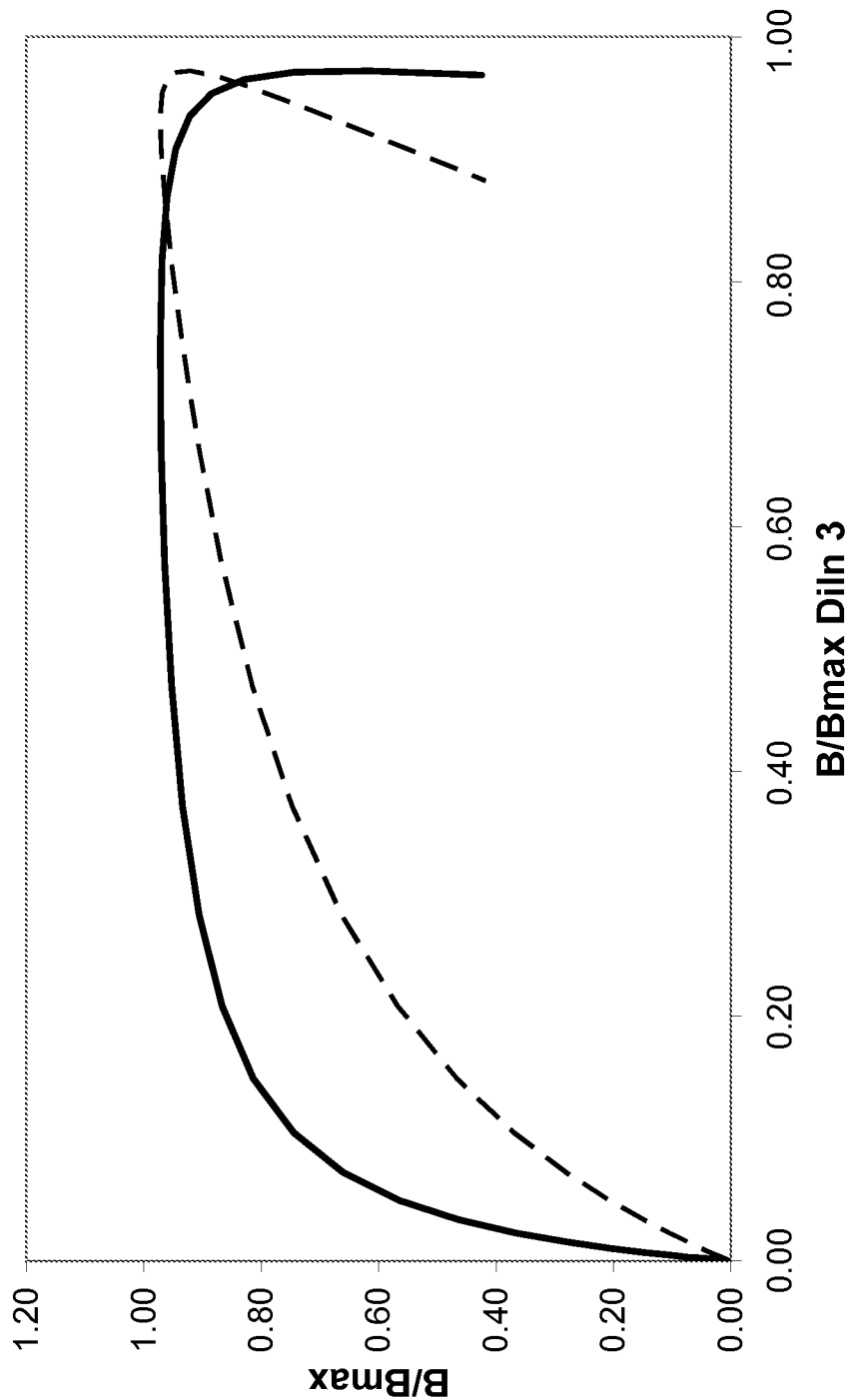

The model as described herein can be used to compute responses for any given dilution and set up algorithms to ensure that the analyte concentration in any tip within the calibration range. Graphic means of representing the data are shown in FIG. 17, wherein the normalized assay response (B/Bmax) is plotted against the log normalized concentration (C/C0.5) for relative dilutions: 1:1 (solid line), 5:1 (dashed line), and 25:1 (dotted line). FIGS. 18 and 19 illustrate a similar example as FIG. 17 at different normalized concentrations. Simple pattern recognition algorithms can be used to identify valid data for high concentration samples. For example, for most of the dose-response, the signal decreases with dilution. When signal for any dilution equal or exceed that of the next higher dilution, the lower dilution result is rejected. In another example, concentrations derived by using the calibration function shown in Example 4, should correspond within some system imprecision with the known dilutions. If the calculated concentration for a low dilution is lower than would correspond with those for higher dilutions, the lower dilution result can be rejected.

When the assay dose-response approaches a maximum, the slope of the concentration ($\Delta C/\Delta S$) versus signal increases. For assays in which the relative variation in signal ($\Delta S/S$) is essentially constant (for example some instances of the system as described) this translates to a bigger variation in the calculated concentration result at higher concentrations. As provided herein, dilution or serial dilution can provide a concentration precision as achieved by immunoassays at signal levels significantly greater (for example, >10-fold) higher than the blank (zero analyte) signal but not close to the maximum signal (for example<0.3*Max. signal). Serial dilution can allow the assay signal to be in this range.

By making several estimates of the analyte concentration from different dilutions, an average value can be obtained. An average value can also be achieved by making replicate measurements at a single dilution level. In some instances, a serial dilution approach as offered by the methods, systems, and device described herein can often eliminate errors due to non-linearity of dilution due to (for example) matrix effects from the sample.

Example 6

Fluorescein is a well-known chemical and high affinity antibodies are known which are specific for the molecule. By attaching several fluorescein moieties to a protein such as albumin, an artificial analyte is created that can be measured by ELISA. The example herein is set up on a microtiter plate to show the feasibility of such an assay and is easily translatable to a device or system of the invention as described herein.

Figure 20:
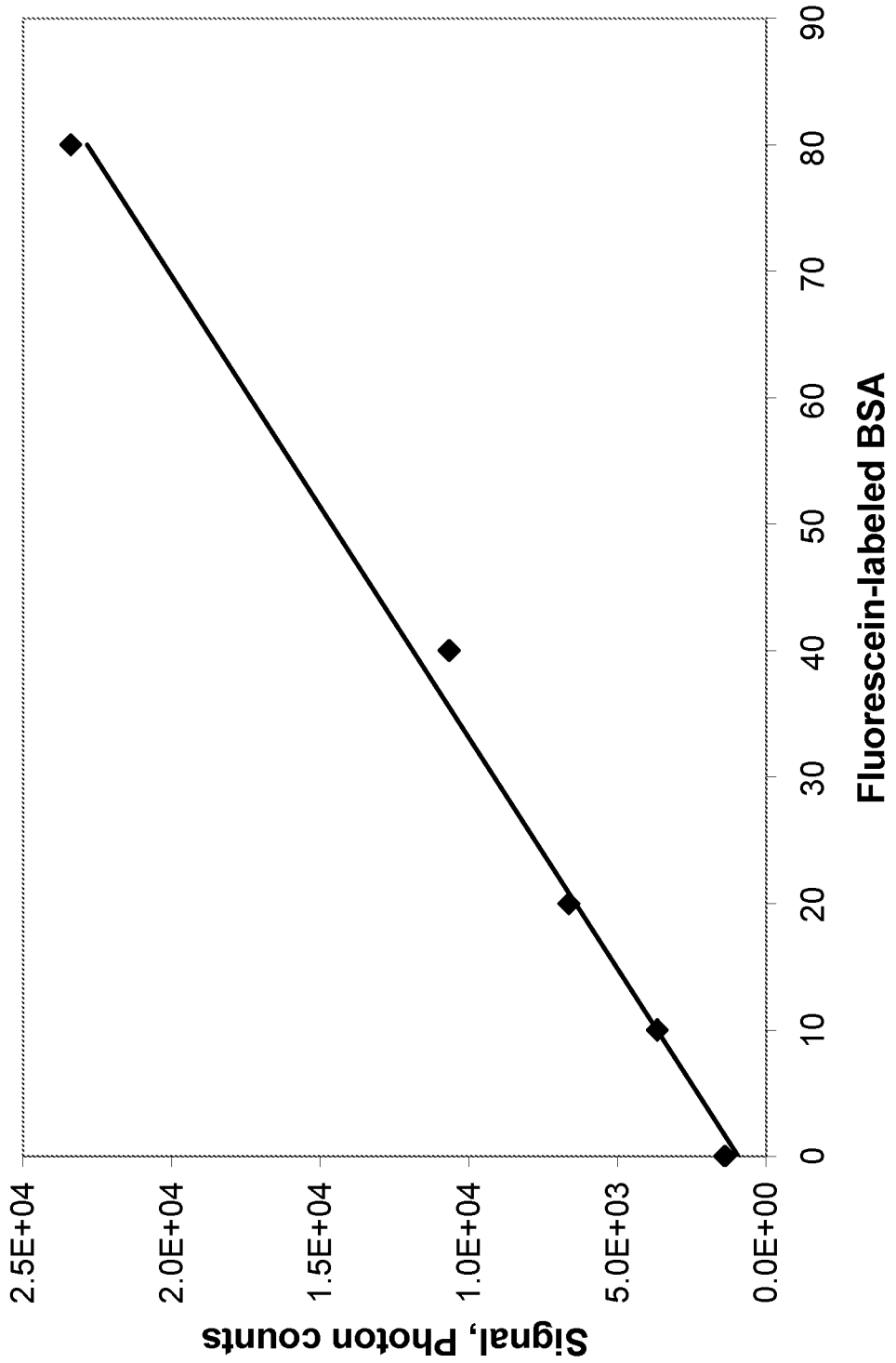
FIG. 20 demonstrates the assay response for a control analyte after the steps of: removal of the detector antibody, washing the assay, and adding a substrate, as read in a spectro-luminometer for 0.5 s.

Anti-fluorescein monoclonal antibody was attached to wells of 384-well microtiter plates to create a capture surface. An assay is performed by adding a series of solutions to the wells and incubating at room temperature for 10 min at each stage when necessary. 30 ul of known concentrations of a commercially available preparation of fluorescein-labeled bovine albumin (sample) with a ratio of about five fluoresceins per molecule were added to the wells. After mechanical removal of the sample, 30 ul of alkaline phosphatase-labeled anti-fluorescein (detector antibody) was added at a concentration of 100 ng/ml. After removal of the detector antibody, the wells were washed three times 40 ul of wash solution ("Wash Buffer" Cat #80-1351 [Assay Designs, Ann Arbor, Mich.] diluted 1:20 before use). PhosphaGLO™ (40 uL) substrate was then added and the assay response was then read in an M5 spectro-luminometer for 0.5 s. The assay response is shown in FIG. 20.

Fluorescein-labeled albumin (5 uL at various concentrations up to 80 ng/mL) dissolved in Tris-buffered saline containing bovine albumin at 3 mg/mL (buffer) was placed in polypropylene tubes and dried by exposure to low humidity air overnight. Complete drying was verified by weighing many tubes before and after drying and verifying the appropriate weight loss and a near-constant final weight was achieved. The analyte was recovered by adding 5 uL water, 20 uL human serum and 180 uL buffer and mixing. Control experiments were made by mixing 5 uL aliquots of analyte solution with 20 uL serum and 180 uL buffer.

Analyte recovery was measured using the assay as described herein. As shown below, the recovery of assay signal (and analyte) is essentially quantitative at all concentrations. It can be desirable to have good recovery (>90%), which is precise (<2% CV in recovery). In some instances, the assay dose-response is linear over the range of interest by having a low concentration of analyte and excess of the reagents. For example, a linear assay dose-response can be achieved by having sufficient capacity for antigen binding on the capture surface such that even at the highest level of analyte only a moderate proportion (for example, <30%) of sites are occupied at the end of the binding reaction. As described herein, for analytes in the ng/mL range and assays with short incubation times (<say 30 m) this condition is achieved with capture surfaces coated as described previously. In another example, sufficient concentration of detector antibody such that the concentration is not significantly depleted during the detector antibody incubation (for example, <30% of the reagent binds to the surface at the highest antigen levels), and this condition can be satisfied by use of detector antibody concentrations in about 5 to 100 ng/mL. In yet another example, a linear assay dose-response can be achieved by having development of a signal less than the linear response of the detector (for example, a PMT with up to about 4 million photons per second). As described herein, systems and methods can fall within this range. In yet another example, a linear assay dose-response can be achieved by development of a signal sufficiently high as to be precisely measured (for example, photon count rates greater than about 1,000 per second).

Figure 21:
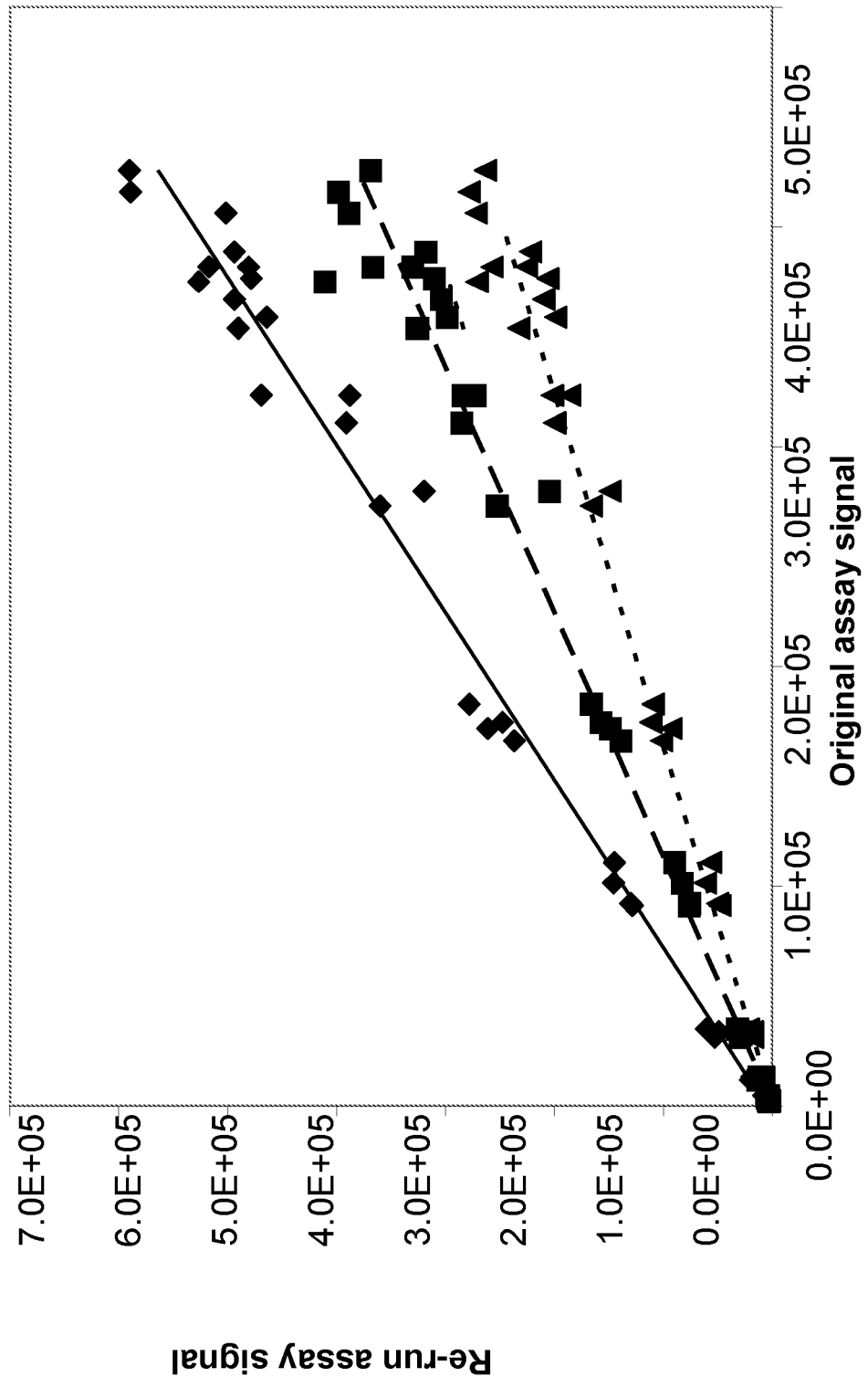
FIG. 21 demonstrates the results of an assay that was evaluated by measuring photons produced over about 10 s in a system herein.

Assay tips (as described herein) were coated by aspiration of the following succession of reagents: 20 uL 5 ug/mL Rabbit anti-fluorescein (Molecular Probes #A6413) in carbonate buffer pH 9, 20 uL 3% bovine albumin in tris-buffered saline pH 8, and 20 uL 2.5 ug/mL bovine albumin labeled with fluorescein (Sigma-Aldrich A9771), each followed by incubation for 10 m and ejection of liquid. The tips were then washed three times by aspiration of bovine albumin in tris-buffered saline pH 8 followed by incubation 3% bovine albumin in tris-buffered saline pH 8. Tips were then dried as described herein. These tips were used to assay samples containing goat anti-fluorescein by incubation of 20 uL aliquots of the following solutions in sequence: goat anti-fluorescein (sample) in tris-buffered saline pH 8 containing 3% BSA, alkaline phosphatase labeled Rabbit-anti-goat fluorescein at 100 ng/mL in Stabilzyme™ (a commercially available solvent), washing four times with Wash Buffer, and PhosphaGLO™ alkaline phosphatase chemiluminogenic substrate, each with an incubation at room temperature for 10 min. The assay was evaluated by measuring photons produced over about 10 s in the instrument using a photomultiplier tube in Molecular Devices M5 luminometer by placing each tip in a custom-modified frame which fits the instrument microtiter plate stage and the results are demonstrated in FIG. 21. In this example, FIG. 21 shows a linear response similar to that in FIG. 20.

0.5 second read time were detected. In this example, the glow level on tips one and two on instrument three gave clearly different results as shown in Table 3. The instrument was then used to wash the tips and to introduce fresh PhosphaGLO™ substrate (aspiration 2). Results are presented as ratios of glow rate for each tip to the average for

TABLE 2

Configurations of assays for candidate control analytes

| Capture surface reagent 1 | Capture surface reagent 2 | Analyte | Detector: APase-labeled |
|---|---|---|---|
| Anti-fluorescein | | Fluorescein-labeled albumin | Anti-fluorescein |
| Anti-fluorescein | Fluorescein-labeled albumin | Anti-fluorescein (species X) | Anti X-Ig |
| Avidin | | Biotinylated-species X-IgG | Anti X-Ig |
| Anti-biotin | Biotin-labeled albumin | | Anti-biotin or Streptavidin |
| Anti-digoxin | Digoxin-labeled albumin | | Anti-digoxin |
| Fluorescein-labeled albumin | | Anti-fluorescein (species X) | Anti-X-Ig |
| Anti-biotin | Biotinylated anti-fluorescein | Anti-fluorescein (species X) | Anti-X-Ig |

Example 7

This example illustrates the predictability of response from an immunoassay for CRP using assay tips as described herein following initial addition of reagents, removal of the reaction product, washing the tips then reintroduction of some or all assay components. The assay sequence was: tips were incubated in prototype instruments at 34 C for 10 min in succession with (1) sample (CRP 0.3, 3, 30, 150 and 300 ug/mL), diluted by the instrument 500 then 2000-fold (2) alkaline phosphatase labeled rabbit anti-goat IgG ["Dab"] (5 ng/mL) then washed three times and (3) with Phospha-GLO™ alkaline phosphatase chemiluminogenic substrate ["Substrate"]. The experiment was performed on several instruments which also read the proton production rate over 10 seconds after step 3. Final (in tip) CRP concentrations were 0.15, 0.6, 1.5, 6, 15, 60, 75, 300 and 600 ng/mL and glow levels ranged from 2,000 to 600,000 counts/0.5 sec. In some experiments, after step (3) in the assay, the reaction product was discarded and variously steps 3 (diamonds and solid line), steps 2+3 (squares and dashed line), or steps 1+2+3 (triangles and dotted line) were repeated and the results are presented as re-processed assay signal versus original assay signal as shown in FIG. 22.

The re-processed assay signals were linearly related (proportional) to the original assay signal. The second substrate addition gave a higher signal relative to the original whereas reprocessed assays in which Dab and substrate were both introduced or those where sample, Dab and substrate were all reintroduced gave lower signals than the original. In an example using this method, all steps in an assay sequence can be examined for quality control to understand if they went as expected according to the expected relationship between the first and subsequent iterations of assay steps.

For example as described herein, if an assay step has not happened properly, then the assay result can either be rejected as incorrect or the later iterations of the assay result can be used as the appropriate assay response.

An immunoassay for C-reactive protein was preformed in a system as described herein. Six equivalent assay tips were incubated in succession with sample (200 ng/mL CRP), alkaline phosphatase labeled rabbit anti-goat IgG then washed and incubated with PhosphaGLO™ alkaline phosphatase chemiluminogenic substrate. Incubations were for 10 min at 34 C. The experiment was performed on three instruments which also read the proton production rate over 10 seconds. On average about 40,000 counts (photons) per the six tips on each respective instrument. After the second aspiration, tips one and two gave results in line with the other four in instrument three indicating that whatever problem had been responsible for low signal in tips one and two had been rectified.

TABLE 3

Recovery of appropriate signal from malfunctioning tips

| | Signal, Ratio to average Instrument # | | | |
|---|---|---|---|---|
| | 1 | 2 | 3 | 3 |
| | Aspiration # | | | |
| Tip # | 1 | 1 | 1 | 2 |
| 1 | 1.002 | 0.988 | 0.460 | 1.043 |
| 2 | 0.848 | 1.045 | 0.917 | 0.929 |
| 3 | 0.959 | 0.893 | 1.141 | 1.035 |
| 4 | 1.062 | 1.067 | 1.103 | 1.028 |
| 5 | 1.049 | 0.981 | 1.171 | 1.022 |
| 6 | 1.079 | 1.025 | 1.207 | 0.942 |
| CV, % | 8.6 | 6.2 | 28.3 | 5.0 |

What is claimed is:

1. A method of detecting at least two analytes in a biological sample using a reader assembly, the method comprising:
   receiving into the reader assembly a cartridge comprising a sample unit containing the biological sample and an array of reagent units, wherein a reagent unit of the array of reagent units comprises a diluent; forming a diluted biological sample by combining the diluent with the biological sample;
   inserting a tip of a first assay unit directly coupled to a fluid transfer device of the reader assembly into the sample unit such that the first assay unit and the sample unit are in fluid communication via the tip;
   drawing, by means of a fluid transfer device in the reader assembly, at least a portion of said diluted biological sample from said sample unit to the first assay unit to provide a first sample portion in the first assay unit;
   inserting a tip of a second assay unit directly coupled to the fluid transfer device into the sample unit such that the second assay unit and the sample unit are in fluid communication via the tip of the second assay unit;
   drawing, by means of the fluid transfer device in the reader assembly, a second portion of said diluted biological sample from said sample unit into the second assay unit to provide a second sample portion in the second assay unit, wherein said second sample portion is not in fluid communication with said first sample portion;

performing a first assay for detecting a presence of a first analyte in said first sample portion in the first assay unit; and performing a second assay for detecting a presence of a second analyte in said second sample portion.

2. The method of claim 1, further comprising providing a protocol for directing the fluid transfer device to perform the first assay to detect a presence of the first analyte and to perform the second assay to detect the presence of the second analyte.

3. The method of claim 1, wherein the at least two analytes are present at concentrations that differ by at least 2 orders of magnitude.

4. The method of claim 1, wherein performing said first or said second assay comprises:

transferring a reagent from an individual reagent unit to the individual assay unit containing the first sample portion or the second sample portion using said fluid transfer device.

5. The method of claim 1, comprising providing said cartridge containing reagents for performing the first assay and the second assay at a point-of-care (POC) location.

6. The method of claim 1, further comprising detecting signals produced by said first and second assays indicative of said at least two analytes.

7. The method of claim 1, wherein a signal indicative of a presence of said first analyte or a signal indicative of a presence of said second analyte, or both, comprises an optical signal.

8. The method of claim 1, wherein said first assay or said second assay comprises a quantitative assay.

9. The method of claim 1, wherein said biological sample is of a bodily fluid selected from blood, serum, saliva, urine, gastric and digestive fluid, tears, stool, semen, vaginal fluid, interstitial fluids derived from tumorous tissue, and cerebrospinal fluid.

10. The method of claim 1, wherein each of said at least two analytes comprise an analyte selected from polypeptides, glycoproteins, polysaccharides, lipids, nucleic acids, biomarkers, genes, proteins, drugs, prodrugs, pharmaceutical agents, drug metabolites, expressed proteins, cell markers, antibodies, hormones, cholesterol and other metabolites, and combinations thereof.

11. The method of claim 1, wherein said biological sample is a fingerstick blood sample.

12. The method of claim 1, wherein performing a first assay or performing a second assay comprises performing an assay for detection of an analyte indicative of a microorganism or virus.

13. The method of claim 1, wherein performing a first assay or performing a second assay comprises performing an assay for detection of an analyte indicative of an infectious disease.

14. The method of claim 1, wherein performing a first assay or performing a second assay comprises performing an assay for detection of an analyte indicative of an infectious disease condition.

15. The method of claim 2, wherein the first assay is different than the second assay.

16. The method of claim 2, further comprising:

detecting an identifier of the cartridge by an identifier detector; and selecting automatically the protocol from a plurality of protocols based on the identifier.

17. The method of claim 16, further comprising:

communicating by a communication assembly of the reader assembly the identifier detected to an external device that is remote from the reader assembly and that stores the plurality of protocols, and remotely selecting the protocol to be run on the fluid transfer device from the plurality of protocols based on the identifier.

18. The method of claim 17, wherein said selected protocol is electronically received by the reader assembly.

19. The method of claim 18, wherein said first assay and said second assay are performed at a point-of-care (POC) location according to said selected protocol.

20. A method of detecting at least two analytes in a biological sample using a reader assembly, the method comprising:

receiving a cartridge comprising a frame holding an array of individual, addressable reagent units and a sample unit in the reader assembly, wherein the sample unit contains the biological sample;

forming a diluted biological sample by combining the biological sample with a diluent;

moving the cartridge into fluid communication with a first assay unit via a tip of the first assay unit;

drawing, by means of a fluid transfer device of the reader assembly that is directly coupled to the first assay unit, at least a portion of the diluted biological sample from the sample unit of the cartridge to the first assay unit to provide a first sample portion in the first assay unit;

moving the cartridge into fluid communication with a second assay unit via a tip of the second assay unit;

drawing, by means of the fluid transfer device of the reader assembly that is directly coupled to the second assay unit, at least a portion of the diluted biological sample from the sample unit of the cartridge to the second assay unit to provide a second sample portion in the second assay unit, wherein drawing the diluted biological sample into the first assay unit and drawing the diluted biological sample into the second assay unit occurs simultaneously;

performing a first assay for detecting a presence of a first analyte in the first sample portion in the first assay unit; and performing a second assay for detecting a presence of a second analyte in the second sample portion in the second assay unit.

21. The method of claim 20, wherein forming the diluted biological sample comprises:

diluting, by at least 3-fold, the biological sample with the diluent.

22. The method of claim 20, wherein a detectable range of signals indicative of the at least two analytes is about 1,000 to about 1,000,000 counts per second using a photomultiplier as a detector.

23. The method of claim 20, further comprising:

diluting the first sample portion in the first assay unit with the diluent to achieve a further degree of dilution of the biological sample.

24. The method of claim 20, wherein performing the first assay and performing the second assay are carried out simultaneously.

25. The method of claim 24, wherein the first analyte is a drug, prodrug, or drug metabolite, and wherein the second analyte is a drug, prodrug, or drug metabolite that is different from the first analyte, and further comprising detecting drug-drug interactions based on detection of the presence of the first analyte and of the second analyte.

26. A method of detecting at least two analytes in a biological sample using a reader assembly, the method comprising:
- receiving a cartridge comprising an array of individual, addressable reagent units and a sample unit in the reader assembly, wherein the sample unit contains the biological sample;
- placing a first assay unit in fluid communication with the cartridge, wherein the first assay unit comprises an interior reaction site comprising an immobilized reagent;
- drawing, by means of a fluid transfer device of the reader assembly, a portion of the biological sample from the sample unit of the cartridge to the first assay unit such that a first analyte binds to the immobilized reagent, wherein the first assay unit is directly coupled to the fluid transfer device:
- placing the first assay unit into fluid communication with a first reagent unit of the array of reagent units;
- drawing a cartridge reagent from the first reagent unit into the first assay unit such that the cartridge reagent reacts with the bound first analyte to produce a signal indicative of a presence of the first analyte;
- placing a second assay unit in fluid communication with the cartridge, wherein the second assay unit comprises a second interior reaction site comprising a second immobilized reagent;
- drawing, by means of the fluid transfer device of the reader assembly, a portion of the biological sample from the sample unit of the cartridge to the second assay unit such that a second analyte in the biological sample binds to the second immobilized reagent, wherein the second assay unit is directly coupled to the fluid transfer device;
- placing the second assay unit in fluid communication with a second reagent unit of the array of reagent units;
- drawing a second cartridge reagent from the second reagent unit into the second assay unit such that the second cartridge reagent reacts with the bound second analyte to produce a signal indicative of a presence of the second analyte; and
- detecting a signal indicative of the presence of the first analyte and a signal indicative of the second analyte by a detection device.

27. The method of claim 26, wherein the first assay unit comprises a tubular tip.

* * * * *